(12) United States Patent
Liotta et al.

(10) Patent No.: US 11,981,652 B2
(45) Date of Patent: May 14, 2024

(54) GLUN2C/D SUBUNIT SELECTIVE ANTAGONISTS OF THE N-METHYL-D-ASPARTATE RECEPTOR

(71) Applicant: Emory University, Atlanta, GA (US)

(72) Inventors: Dennis Liotta, Atlanta, GA (US); Stephen Traynelis, Decatur, GA (US); Yao Jing, Dunwoody, GA (US)

(73) Assignee: Emory University, Atlanta, GA (US)

( * ) Notice: Subject to any disclaimer, the term of this patent is extended or adjusted under 35 U.S.C. 154(b) by 64 days.

(21) Appl. No.: 17/042,726

(22) PCT Filed: Mar. 28, 2019

(86) PCT No.: PCT/US2019/024578
§ 371 (c)(1),
(2) Date: Sep. 28, 2020

(87) PCT Pub. No.: WO2019/191424
PCT Pub. Date: Oct. 3, 2019

(65) Prior Publication Data
US 2021/0017149 A1    Jan. 21, 2021

Related U.S. Application Data

(60) Provisional application No. 62/649,112, filed on Mar. 28, 2018.

(51) Int. Cl.
*C07D 401/04* (2006.01)
*A61K 31/415* (2006.01)
(Continued)

(52) U.S. Cl.
CPC .......... *C07D 401/04* (2013.01); *A61K 31/415* (2013.01); *A61K 31/4155* (2013.01);
(Continued)

(58) Field of Classification Search
None
See application file for complete search history.

(56) References Cited

U.S. PATENT DOCUMENTS

| 5,252,584 A | 10/1993 | Carling |
| 8,178,667 B2 | 5/2012 | Lindsley |

(Continued)

FOREIGN PATENT DOCUMENTS

| CN | 106568976 | 5/2018 |
| WO | 2009006437 | 1/2009 |

(Continued)

OTHER PUBLICATIONS

Acker ("Structure-Activity Relationships and Pharmacophore Model of a Noncompetitive Pyrazoline Containing Class of GluN2C/GluN2D Selective Antagonists" J. Med. Chem. 2013, 56, Supporting Information (SI), pp. S1-S45). (Year: 2013).*

(Continued)

*Primary Examiner* — Amy C Bonaparte
(74) *Attorney, Agent, or Firm* — Emory Patent Group

(57) ABSTRACT

A compound according to Formula (I) or salts or prodrugs thereof and pharmaceutical formulations comprising the compound are provided herein for the treatment of neurological disorders. The disorders may include providing neuroprotection, preventing neurodegeneration, treating neuro- (Continued)

pathic pain or treating schizophrenia, psychoses or depression. Furthermore, the compounds may be used in combination with another active ingredient.

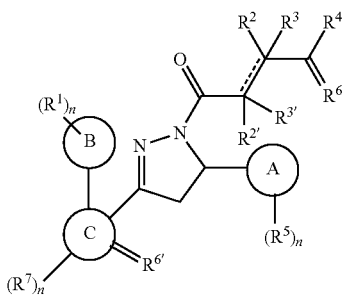

(I)

20 Claims, 1 Drawing Sheet

(51) Int. Cl.
| | |
|---|---|
| *A61K 31/4155* | (2006.01) |
| *A61K 31/4709* | (2006.01) |
| *A61K 31/497* | (2006.01) |
| *A61K 45/06* | (2006.01) |
| *A61P 25/00* | (2006.01) |
| *A61P 25/18* | (2006.01) |
| *A61P 25/24* | (2006.01) |
| *A61P 25/28* | (2006.01) |
| *C07D 231/06* | (2006.01) |
| *C07D 401/14* | (2006.01) |
| *C07D 405/04* | (2006.01) |
| *C07D 409/04* | (2006.01) |
| *C07D 409/14* | (2006.01) |

(52) U.S. Cl.
CPC ........ *A61K 31/4709* (2013.01); *A61K 31/497* (2013.01); *A61P 25/00* (2018.01); *A61P 25/18* (2018.01); *A61P 25/24* (2018.01); *A61P 25/28* (2018.01); *C07D 231/06* (2013.01); *C07D 405/04* (2013.01); *C07D 409/04* (2013.01); *C07D 409/14* (2013.01); *A61K 45/06* (2013.01); *C07D 401/14* (2013.01)

(56) References Cited

U.S. PATENT DOCUMENTS

| | | | |
|---|---|---|---|
| 11,117,882 | B2 | 9/2021 | Acker |
| 2015/0344501 | A1* | 12/2015 | Kiessling ............. C07D 417/04 548/194 |

FOREIGN PATENT DOCUMENTS

| | | |
|---|---|---|
| WO | 2009137843 | 11/2009 |
| WO | 2010088408 | 8/2010 |
| WO | 2010088414 | 8/2010 |

OTHER PUBLICATIONS

Dou ("Discovery of new GSK-3-inhibitors through structure-based virtual screening" Bioorganic and Medicinal Chemistry Letters 28, 2018, p. 160-166, first published online Nov. 24, 2017) (Year: 2017).*
STN CAS® registry (RN) file for compound 1311990-28-9, first entered in STN on Jul. 7, 2011 (Year: 2011).*
STN CAS® registry (RN) file for compound 1785763-13-4, first entered in STN on Jun. 22, 2015 (Year: 2015).*
Acker, T. et al., "Mechanism for noncompetitive inhibition by novel GluN2C/D N-methyl-D-aspartate receptor subunit-selective modulators", Molecular Pharmacology, 2011, vol. 80, No. 5, pp. 782-795.
Acker et al., "Structure-Activity Relationships and Pharmacophore Model of a Noncompetive Pyrazoline Containing Class of GluN2C/GluN2D Selective Antagonists", Journal of Medicinal Chemistry, 2013, vol. 56, No. 16, pp. 6434-6456.
Chen, L. et al., "Discovering severe acute respiratory syndrome coronavirus 3CL protease inhibitors: cirtual screening, surface plasmon resonance, and fluororescence resonance energy transfer assays", Journal of Biomolecular Screening, 2006, vol. 11, No. 8, pp. 915-921.
Desos, P. et al., "Structure-activity relationships in a series of 2(1H)-quinolones bearing different acidic function in the 3-position: 6,7-dicholor-2(1H)-oxoquinoline-3-phosphonic acid, a new potent and selective AMPA/Kainate antagonist with neuroprotective properties", Journal of Medicinal Chemistry, 1996, vol. 39, No. 1, pp. 197-206.
Kadieva M.G. et al., "Antagonists of AMPA/KA and NMDA (glycine site) glutamate receptors", Pharmaceutical Chemistry Journal, 2008, vol. 42, No. 2, pp. 72-80.
Podvinec, M., et al., "Novel inhibitors of dengue virus methyltransferase: discovery by in vitro-driven virtual screening on a desktop computer grid", Journal of Medicinal Chemistry, 2010, vol. 53, No. 4, pp. 1483-1495 and supporting information.

* cited by examiner

GLUN2C/D SUBUNIT SELECTIVE ANTAGONISTS OF THE N-METHYL-D-ASPARTATE RECEPTOR

CROSS-REFERENCE TO RELATED APPLICATIONS

This application is the National Stage of International Application No. PCT/US2019/024578 filed Mar. 28, 2019, which claims the benefit of U.S. Provisional Application No. 62/649,112 filed Mar. 28, 2018. The entirety of each of these applications is hereby incorporated by reference for all purposes.

STATEMENT REGARDING FEDERALLY SPONSORED RESEARCH OR DEVELOPMENT

This invention was made with government support under NS065371 awarded by the National Institutes of Health. The government has certain rights in the invention.

TECHNICAL FIELD

The present disclosure relates to N-methyl-D-aspartic acid receptor (NMDAR) modulators and, in particular, to subunit specific allosteric modulators of NMDARs for the treatment of a wide range of neurological disorders and conditions, such as Alzheimer's disease, Parkinson's disease, schizophrenia, epilepsy, depression, stroke, psychosis and the like. It also relates to pharmaceutical compositions and methods of treatment of such neurological disorders involving NMDAreceptors.

BACKGROUND

The N-methyl-D-aspartate (NMDA) receptors are ligand-gated ion channels which belong to the ionotropic glutamate receptor (iGluR) family. Because of its high permeability of $Ca^{2+}$, $Na^+$, $K^+$ and a voltage-dependent $Mg^{2+}$ block, the NMDA receptor contributes to synaptic plasticity and excitatory neuronal transmission in the central nervous system (CNS). The functional NMDA receptors are heterotetramers and are assembled from two glycine-binding GluN1 subunits with either two glutamate-binding GluN2 (A-D) subunits or a combination of one GluN2 and one GluN3. The GluN2 subunits are critical in determining biophysical and pharmacological properties of the NMDA receptor. GluN2D subunits have been reported to regulate synaptic transmission in basal ganglia, which regulate movement and are imbalanced in movement disorders such as Parkinson's disease. Since GluN2D is located at basal ganglia, GluN2D subunits have been treated as potential targets for neuropathological diseases. GluN2D subunits are also present in interneurons, and could alter circuit function by influencing the balance of excitatory to inhibitory activity in a given network.

Each subunit folds into four semiautonomous domains, including an amino-terminal domain (ATD), a ligand-binding domain (LBD), a transmembrane domain (MD) and an intracellular carboxyl-terminal domain (CTD) [1,8].

ATD domains are extracellular domains that have multiple binding sites for allosteric modulators, which affect different subunits. The ATD of the NMDA receptor controls significant pharmacological properties, such as channel opening probability, deactivation time course, and agonist $EC_{50}$ [1,10-12]. The X-ray crystal structure of GluN1-GluN2B ATD has been resolved, which revealed the ATD as a clamshell-like structure with two parts R1 and R2 [9,13,14]. Because the ATD of the NMDAreceptor has lower sequence homology compared to non-NMDA glutamate receptors, it can regulate receptor function. $Zn^{2+}$ binds to the GluN2B ATD clamshell and the GluN2A ATD clamshell and partially inhibits both GluN2A and GluN2B subunits at physiological concentrations [1,15,16]. The GluN2B-selective inhibitor ifenprodil binds within the interface between the GluN1 and GluN2B ATD heterodimer, which is a different binding site than $Zn^{2+}$ ions [14].

The extracellular LBD, which consists of two stretches of amino acids (S1 and S2), has a clamshell-like conformation [11]. One half of the clamshell is formed by S1, which is located on the amino-terminal side of membrane helix M1, while the other half of the clamshell is assembled primarily from S2, which is located between the membrane helices M3 and M4 [1]. Between these two lobes, the glutamate receptor is activated by the binding of the glutamate agonist within this cleft. Once the agonist binds, the LBD undergoes a conformational change and transfers the signal to the TMD. Although the LBD of the NMDA receptor and the LBD of non-NMDA glutamate receptors have high sequence homology, the NMDA and AMPA receptors have different channel opening patterns because of the respective conformational changes [11,17].

The glutamate receptor TMD, which is linked to the LBD, forms a transmembrane pore that has a similar structure to an inverted $K^+$ channel pore. The TMD has three transmembrane helices, M1, M3 and M4, and a re-entrant M2 loop connecting M1 and M3 in the pore [1,9]. Voltage-dependent $Mg^{2+}$ blockage of the NMDA receptor and uncompetitive antagonists take place within the channel pore [18]. The linker region between the LBD and TMD impact the ligand binding that further modulates receptor function [19].

The glutamate receptor CTDs are different in sequence and length. The CTD affects stabilization, membrane targeting and post-translational modifications [1,19]. However, a lack of a CTD for glutamate receptor subunits could change regulation of membrane trafficking and receptor function because of deletion of sites for phosphorylation or other post-translational modification, as well as binding sites for intracellular proteins [1].

The four GluN2 subunits possess different properties, such as channel opening probability, deactivation time course and agonist sensitivity. Compared to other GluN2-containing receptors, GluN2A subunits are less sensitive to both glycine and glutamate and have a higher open probability and faster deactivation time course following rapid removal of glutamate, as occurs within the synaptic cleft. The GluN2 subunits are critical in determining biophysical and pharmacological properties of the NMDA receptor.

Experiments have shown that the expression of functional NMDA receptors in rats' brains is controlled throughout development both spatially and temporally [20]. The experiments start at postnatal day one. The intensity of the expression of the GluN1 mRNA gradually increases in all neuronal cells in the rats' brains. GluN2B and GluN2D are observed at low levels in the forebrain (cortex and hippocampus) and lower brain-stem region (thalamus, hypothalamus, and brain stem), respectively. The expressions of GluN2B and GluN2D mRNAs are markedly decreased after the second week of birth. GluN2A and GluN2C mRNAs appear later than the other subunit mRNAs and continue to express in forebrain and the cerebellum through adulthood, respectively [20,21]

The crystal structure of agonist-bound GluN1/GluN2 LBD heterodimers shows that the agonists bind at the cleft between the D1 and D2 regions of LBD. Agonists such as glycine, L/D-serine, and L/D-alanine bind to the GluN1 subunit of the NMDA receptor, while endogenous agonists including glutamate, D/L-aspartate, homocysteate, and cysteinesulfinate bind to the GluN2 subunit [1,22-24]. Although GluN3 binds glycine like GluN1, the affinity of glycine that binds to GluN3 is 600-fold higher than that with which it binds to GluN1 [25].

Competitive antagonists bind at the agonist binding site but do not activate the NMDA receptor. NMDA competitive antagonists were pursued as a therapeutic approach in the early 1990s. Numerous competitive antagonists of the GluN1 and GluN2 subunits have been identified. For example, 7-chlorokynurenic acid and its analog 5,7-dichlorokynurenic acid (5,7-DCKA) are competitive antagonists of the GluN1 subunit [26,27], while (R)-2-amino-5-phosphonopentanoate and its analogs are used as competitive antagonists of the GluN2 subunit to distinguish the activity of NMDA receptors from the other glutamate non-NMDA receptors [1]. Due to high homology among GluN2 LBDs, the GluN2 competitive antagonists are not GluN2 selective [28]

Compounds that bind deep in the ion channel pore, such as adamantine and memantine, act as uncompetitive antagonists [29,30]. Uncompetitive antagonists, also known as channel blockers, require activation of the NMDA receptor before binding because the blockade of the channel pore is voltage- and use-dependent [31]. Due to this fact, the channel blockers can produce a slow onset of inhibition that depends on the degree of channel activity, and these inhibitors produce more rapid block when the channel opening probability increases. The channel blockers show low subunit selectivity because of the highly conserved ion channel region across GluN2 subunits [32]. Memantine and adamantine have been approved by the FDA for the treatment of Alzheimer's disease and Parkinson's disease, respectively [33]. Other channel blockers, including ketamine, MK-801, phencyclidine (PCP), dextromethorphan, and dextrorphan, share similar binding sites within the pore [31,34-39].

The first noncompetitive, subunit-selective NMDA antagonist identified was the phenylethanolamine ifenprodil. Ifenprodil is GluN2B-selective and is approximately 200-fold more potent at NMDA receptors that contain GluN2B than NMDA receptors that contain GluN2A, GluN2C, or GluN2D subunits [40,41]. Both ifenprodil and its analogs, such as CP-101,606 and Ro 25-6981, bind at the GluN1-GluN2B ATD interface [13,41,42]. Noncompetitive negative allosteric modulator 3-chloro-4-fluoro-N-[(4-[(2-(phenylcarbonyl)hydrazine)carbonyl]phenyl) methyl]-benzenesulfonamide (TCN-201) has been identified as a GluN2A-selective inhibitor and resides in the GluN1-GluN2A heterodimer LBD [17,43,44]. A series of naphthalene and phenanthrene (UBP) derivatives that bind in the LBD region have been identified as potentiators and antagonists of the NMDA receptors. For example, UBP618 inhibits all GluN2 subunits with no selectivity, while UBP714 slightly potentiates the receptor with a modest selectivity for GluN2A and GluN2B subunits over GluN2D subunit [45]. UBP608 and UBP512 are antagonists and potentiators for the GluN2A-containing receptor, respectively [46,47]. Recently, a class of GluN2C- and GluN2D-selective potentiators (3-chlorophenyl)(6,7-dimethoxy-1-((4-methoxyphenoxy)methyl)3,4-dihydroisoquinolin-2(1H)-yl)methanone (CIQ) has been developed with $EC_{50}$ values of 3-6 μM [48,49]. CIQ has structural determinants of activity that reside within the pre-M1-M1 region [50]. This pre-M1-M1 region is not identified with other modulators in the glutamate receptor family [51]. A class of pyrrolidinone (PYD) has been discovered as GluN2C potentiators. For example, PYD-106 exhibit potentiation at GluN2C subunit with an $EC_{50}$ value of 13 μM. Studies suggest that PYD derivatives bind at the interface between the LBD and ATD [52,53]. A series of GluN2C- or GluN2D-selective antagonists such as (E)-4-(6-methoxy-2-(3-nitrostyryl)-4-oxoquinazolin-3(4H)-yl)-benzoic acid (QNZ46) have been reported to act in a noncompetitive, voltage-independent and use-dependent manner. Studies revealed that QNZ46 shows more potent inhibition in the presence of glutamate [43]. A class of dihydroquinoline-pyrazoline (DQP) was first developed by Acker et al. as GluN2C- and GluN2D-containing receptor antagonists [2]. Based on site-directed mutagenesis, DQP has been proposed to bind in a manner dependent on the S2 region of the LBD of the NMDA receptor [32].

Although various promising candidates have been studied in clinical trials, no treatments have been reported to be neuroprotective in Parkinson's disease (PD). For instance, L-dihydroxyphenylalanine (L-DOPA, levodopa), known as the biosynthetic precursor of dopamine, is an effective symptomatic treatment via replacement of dopaminergic stimulation [54]. However, after a period of treatment, most of the patients show motor complications such as dyskinesias and abnormal involuntary choreiform movements. To reduce dyskinesia, the NMDA antagonist amantadine acts as a potent adjunct to L-DOPA therapy [55-57]. Although dopaminergic neurons are the most prominent features, addressing only the dopaminergic deficit in PD cannot avoid non-motor symptoms such as dementia and impairment of autonomic nervous system function. These non-motor symptoms are more important than motor complications [58,59]. Therefore, the neuroprotective treatments need to be developed.

GluN2D subunits have been reported to regulate synaptic transmission in basal ganglia, especially in the striatum, thalamus, subthalamic nucleus (STN), globus pallidus (GPi), and substantia nigra [60-63]. The basal ganglia are a group of subcortical nuclei, which regulate movement and their function becomes imbalanced in movement disorders such as Parkinson's disease [64-66]. Since GluN2D is located in multiple regions of basal ganglia, GluN2D subunits have been considered as potential targets for neuropathological diseases [62]. Models of basal ganglia circuits were built and within the parallel re-entrant circuits, the balance of activity in the parallel pathways plays a key role in regulating movement [67]. Because both excitatory glutamatergic input from the cortex and dopaminergic input from the substantia nigra pars compacta (SNpc) are received by the striatum, the striatum is a critical component and interactions between dopamine receptors and NMDA receptors are essential for healthy brain and diseased brain [68-71]. In the healthy brain, the normal dopaminergic neuronal output from the striatum overall inhibits glutamatergic output from the STN to the GPi [72]. In Parkinson's brain, overstimulation of the GPi is due to an imbalance in the direct (D) and indirect (I) pathways. Excessive inhibitory input from GPi to the motor thalamus (Thal) diminishes thalamic stimulation of the supplementary motor areas, which are indispensable for the normal spontaneous movements [73,74]. Blockade of GluN2D could rectify circuit imbalance that develops with loss of dopaminergic neurons. These studies suggest that GluN2D subunits have crucial roles in brain circuits and movements. Thus, more selective and drug-like GluN2D-selective NIDA receptor modulators are important to develop.

Compound 4-(5-(4-bromophenyl)-3-(6-methyl-2-oxo-4-phenyl-1,2-dihydro-quinolin-3-yl)-4,5-dihydro-1H-pyrazol-1-yl)-4-oxobutanoic acid (DQP-1105) was selected from a $Ca^{2+}$-based screen of ChemDiv and Asinex diversity libraries as GluN2C/D-selective antagonists [75,76] and exhibited inhibition at GluN2C- and GluN2D-containing receptors with an $IC_{50}$ value of 7.0 μM and 2.7 μM, respectively [77]. The actions of DQP-1105 against current responses have been evaluated from recombinant NMDA receptors expressed in *X. laevis* oocytes. When the concentration of DQP-1105 increased, the current response of GluN2C and GluN2D significantly decreased. When the concentration of DQP-1105 increased to 2.7 μM, the current response dropped to 50% of maximum [2]. Studies reported that the $IC_{50}$ values evaluated at recombinant human NMDA receptors were similar to the values tested at recombinant rat NMDA receptors [2]. DQP-1105 has a favorable combination of inhibition activity and selectivity for GluN2D subunit over GluN2A and GluN2B subunits [77]. Therefore, substitutions on the DQP scaffold play a significant role in potency and selectivity.

Researchers have developed the mean current-voltage relationship of GluN1/GuN2D receptors in the presence and absence of DQP-1105. The level of inhibition by DQP-1105 remains the same at all voltages [2] and DQP-1105 has been suggested as noncompetitive and voltage-independent antagonist of the NMDA receptors.

The substitutions on the DQP scaffold play a crucial role in the activity of inhibition and selectivity at GluN2D subunit over other glutamate receptor subunits and several candidate scaffolds performed inhibition with $IC_{50}$ values in the 100-500 nM range and showed a 50- to 200-fold selectivity at the GluN2D-containing receptor over GluN2A and GluN2B subunits [77]. The blood-brain barrier (BBB) penetration of these three compounds was evaluated via the MDR1-MDCK permeability assay [78]. Since the topological polar surface area (TPSA) of some compounds were outside the optimal range for BBB penetration, and the efflux ratio of these compounds are high, they were suggested as being poorly brain penetrable. The compound with lower TPSA and efflux ratio, identified to have a high potential for BBB penetration [77], was evaluated for plasma stability over a two-hour time course assay. Selected compounds were stable in human, rat, and mouse plasma and metabolic stability was also reported via the human liver microsomes assay. The half-life of a carboxylic acid, alcohol, and mono fluorine scaffold was evaluated to be over 60 min, 13 min, and 35 min, respectively. According to this assay, the carboxylic acid derivative exhibited the minimal degradation [77]. Modifications of the substitutions on these rings retained or lowered the activity and selectivity at GluN2C/D-containing receptors. Potent compounds with improved selectivity showed a low potential for BBB penetration. Thus, it is desirable to develop more potent and selective compounds with brain penetration.

SUMMARY

In accordance with an embodiment of the present disclosure there is provided a compound of Formula (I) or salt thereof,

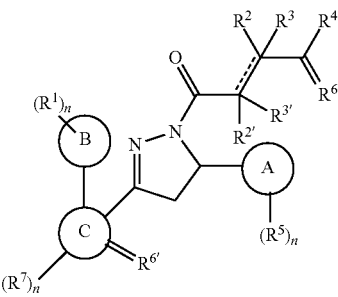

Formula (I)

wherein $R^1$, $R^5$ and $R^7$ are individually and independently selected from the group consisting of a C1 to C3 alkyl, alkoxy, halogen, and trifluoroalkyl;

$R^2$, $R^3$, $R^{2'}$ and $R^{3'}$ are individually and independently selected from H or a halogen;

$R^4$ is selected from the group consisting of an amino, hydroxyl or C1 to C3 alkoxy;

$R^6$ and $R^{6'}$ are individually and independently S, O or absent;

Ring A and Ring B are individually and independently a 5 or 6 membered aryl or heteroaryl or is absent;

Ring C is a monocyclic or bicyclic aryl or heteroaryl ring;

the dashed bond represented by ==== can be a single bond or a double bond; and n is 0, 1, 2 or 3 and $R^1$, $R^2$, $R^3$, $R^{2'}$, $R^{3'}$, $R^4$, $R^5$, $R^6$, $R^{6'}$ and $R^7$ are optionally substituted with $R^{10}$ which is a halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl Further features provide for $R^1$, $R^5$ and $R^7$ to be individually and independently selected from the group consisting of a methyl, ethyl, methoxy, ethoxy, fluoro, chloro, bromo, or $CF_3$; for $R^2$, $R^3$, $R^{2'}$ and $R^{3'}$ to be individually and independently selected from H or a fluoro; for $R^4$ to be selected from an $NH_2$, OH, OMe or OEt; and for $R^{6'}$ to be a S or O when ring C is a bicyclic ring or is absent when Ring C is a monocyclic ring.

Still further features provide for $R^1$ and $R^5$ to be chloro or fluoro substituents, preferably in the para position; and for each of $R^2$ and $R^3$ to be a fluoro when each of $R^{2'}$ and $R^{3'}$ are H or for each of $R^2$ and $R^3$ to be a H when each of $R^{2'}$ and $R^{3'}$ are fluoro and for Rings A and B to be a phenyl, pyridine, pyrazine or a thiophene and Ring C to be a phenyl or a quinolinone or a quinoline-thione ring system.

In one embodiment, Ring A and Ring B are individually and independently selected from:

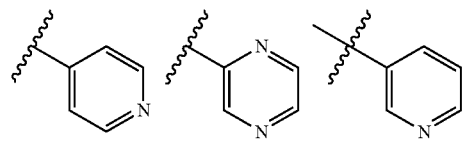

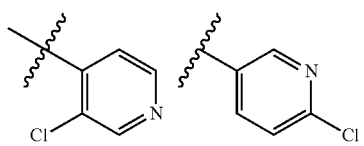
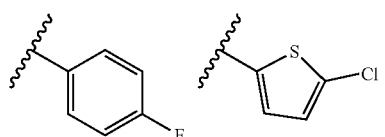
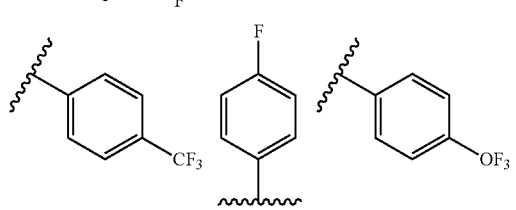
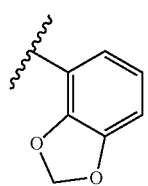
The compounds of Formula (I) can be selected from compounds of Formula (IA), (IB), (IC), (ID), (IE), or (IF), or salts thereof;
Formula (IA)
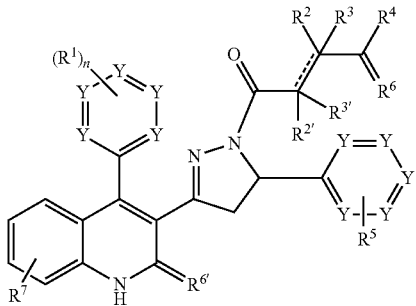
Formula (IB)
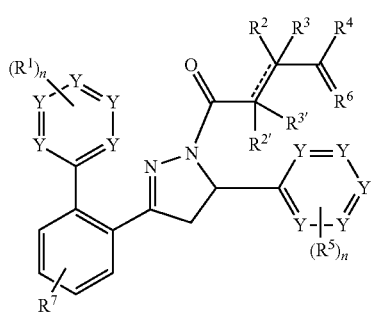
Formula (IC)
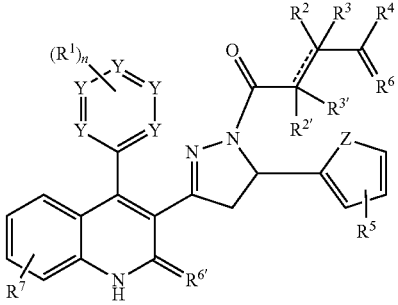
Formula (ID)
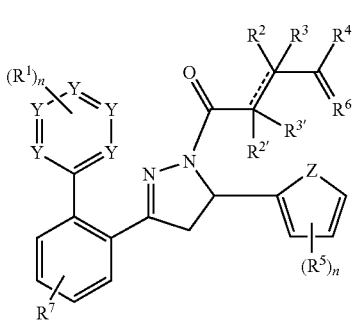
Formula (IE)
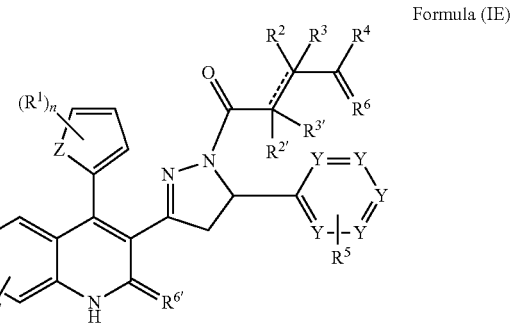
Formula (IF)
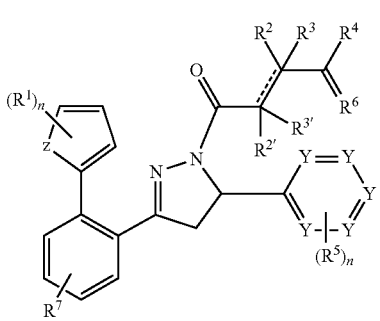
wherein $R^1$, $R^2$, $R^3$, $R^{2'}$, $R^{3'}$, $R^4$, $R^5$, $R^6$, $R^{6'}$, $R^7$ and n are as defined above; and Y is N $CR^5$ or CH and Z is S or O.

Exemplary compounds of Formula (I) include:
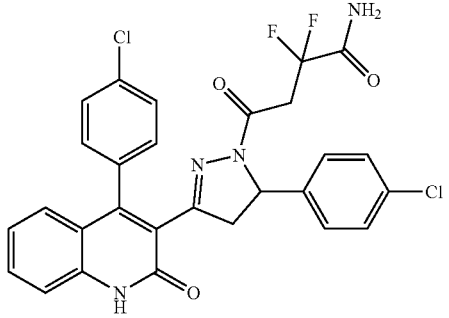
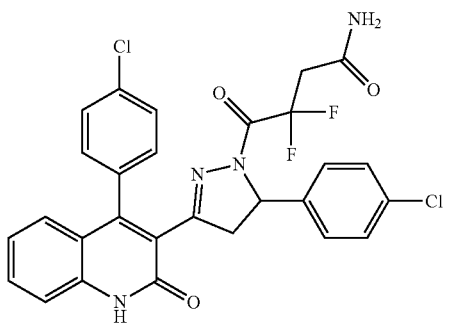
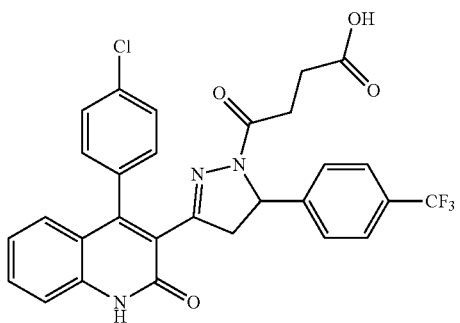
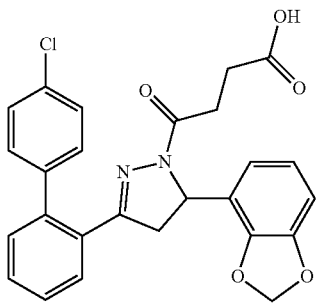
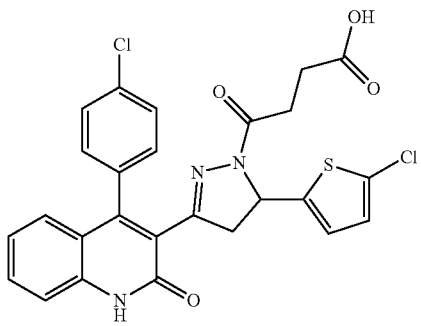
-continued
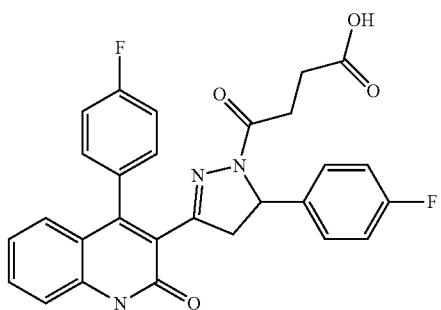
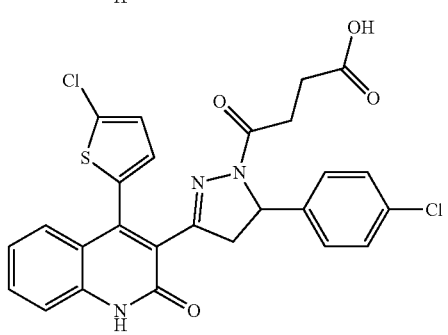
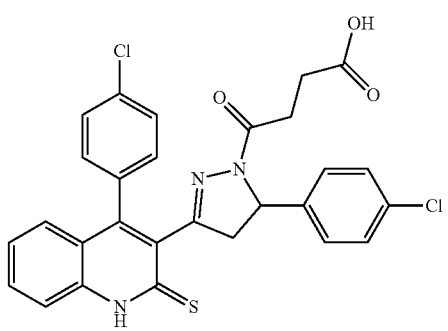
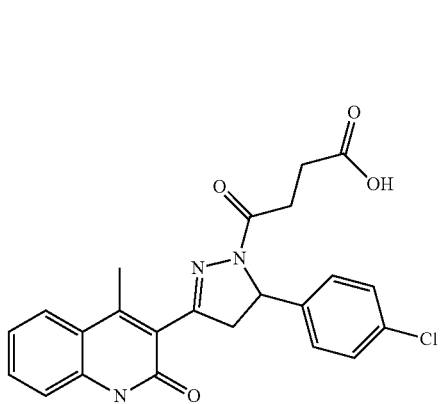
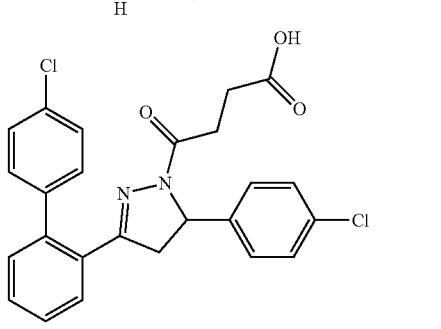

11
-continued
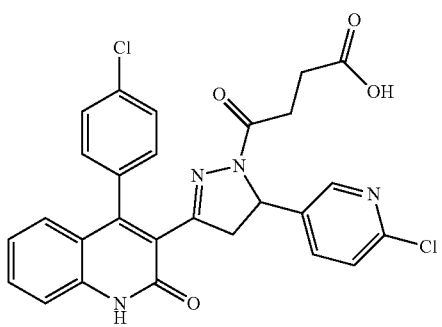
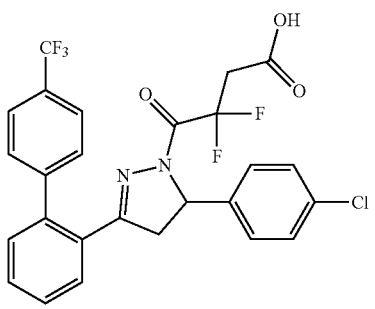
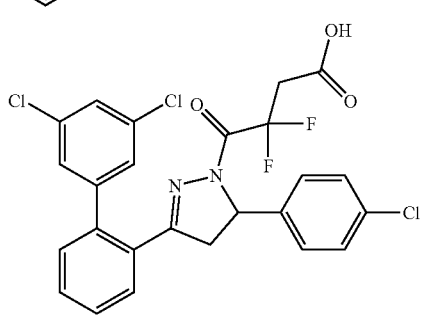
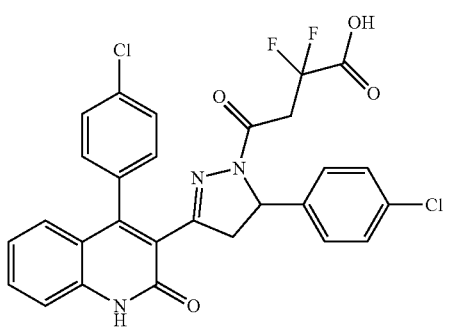
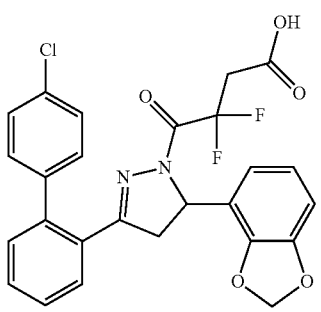
12
-continued
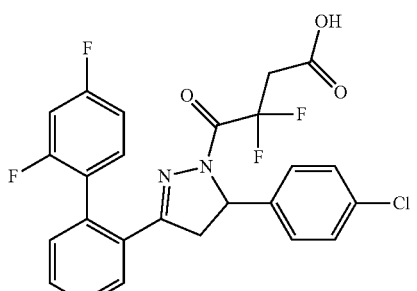
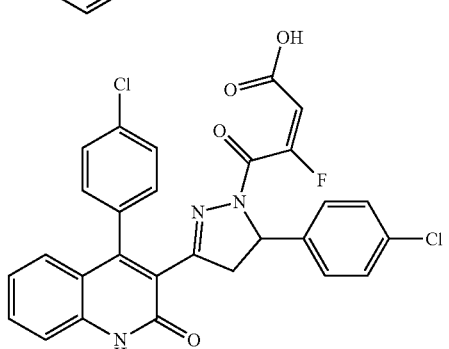
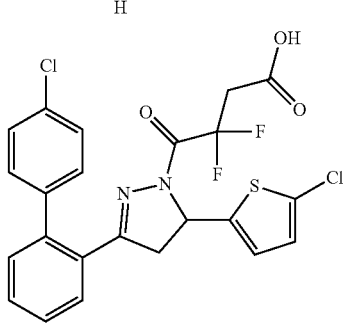
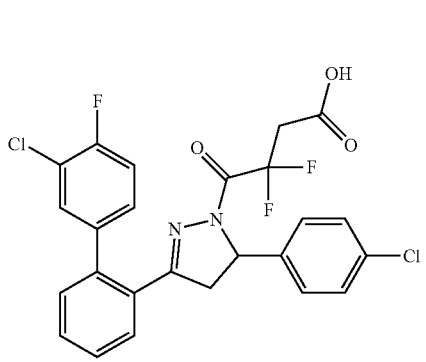
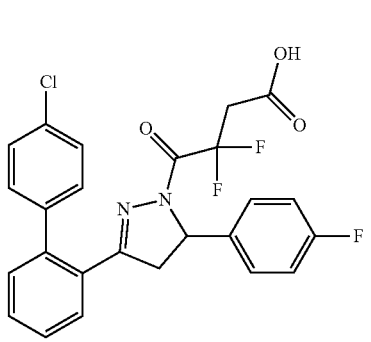

-continued
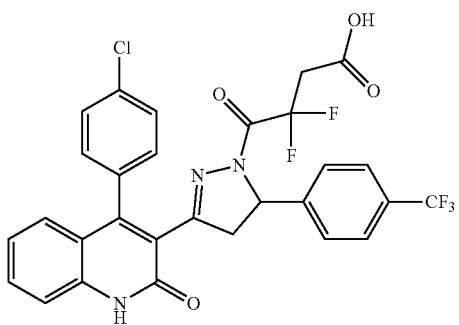
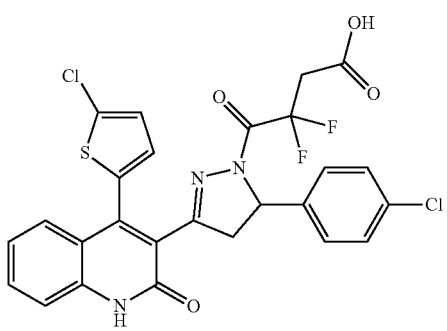
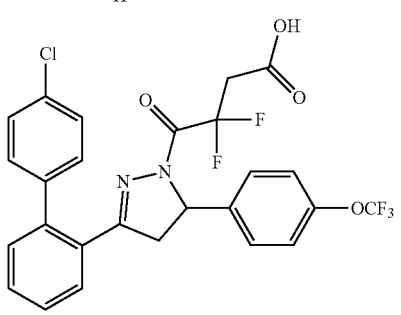
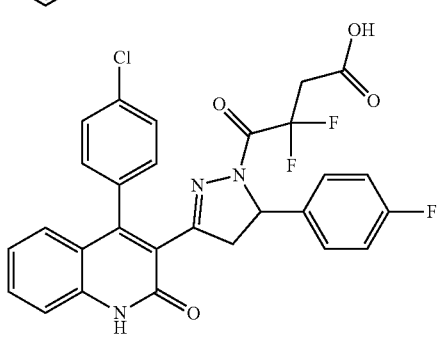
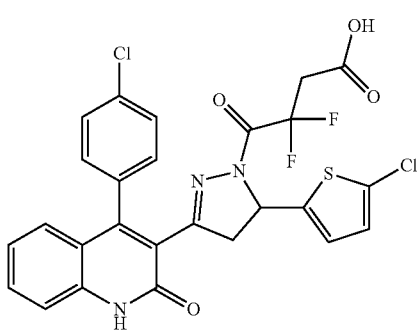
-continued
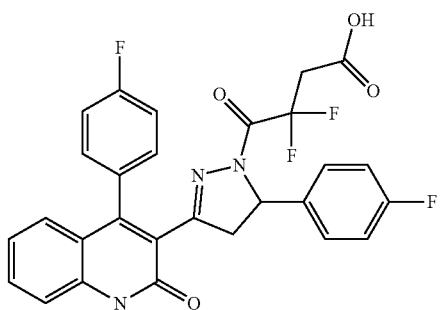
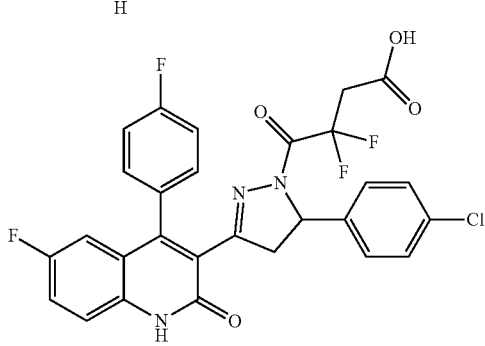
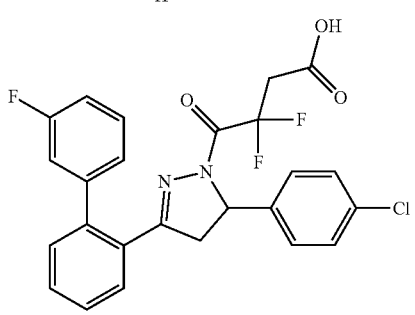
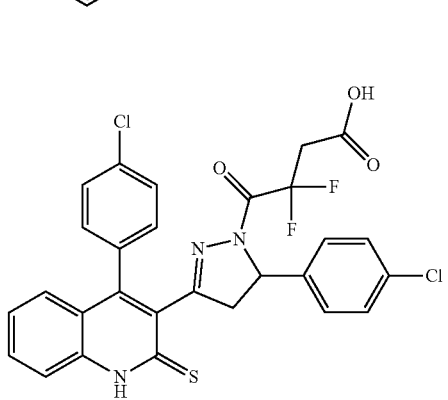
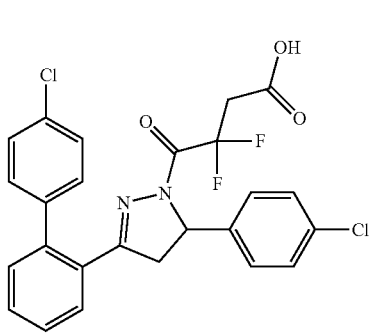

-continued

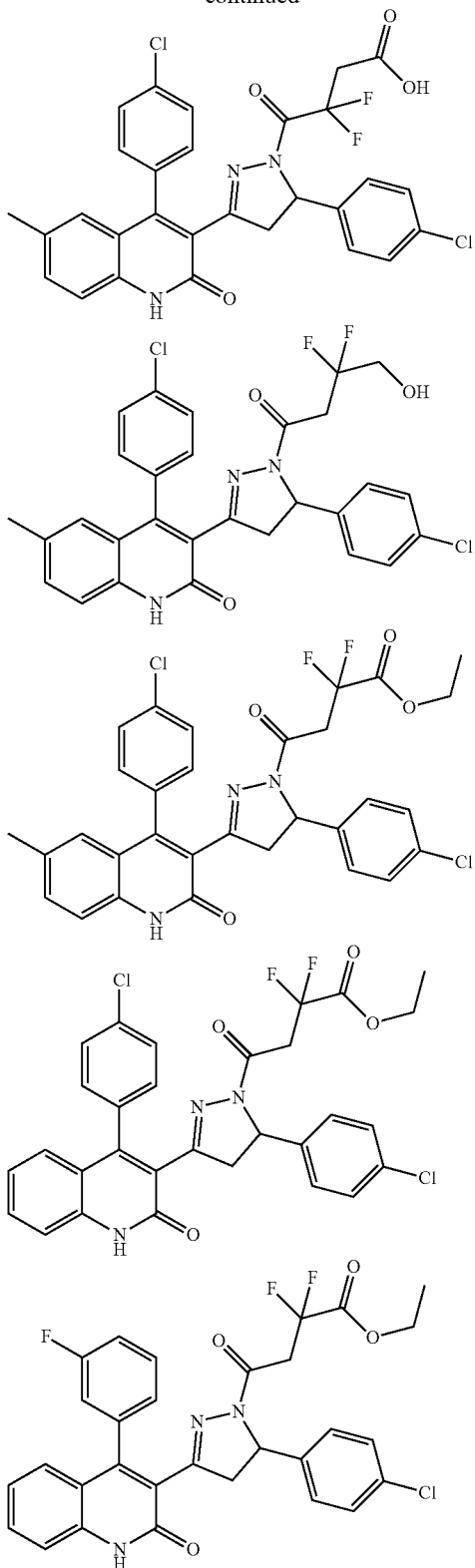

In another embodiment there is provided a method of treating a variety of neurological disorders in a subject in need thereof, the method comprising administering an effective amount of the compound of Formula (I) or salts thereof to the subject.

Treatment of neurological disorders include providing neuroprotection, preventing neurodegeneration, treating neuropathic pain, treating schizophrenia, psychoses, depression and the like.

In certain embodiments, the disclosure contemplates derivatives of compounds disclosed herein such as those containing one or more, the same or different, substituents.

In still another embodiment there is provided a pharmaceutical composition comprising a compound of Formula (I) or salts thereof and a pharmaceutically acceptable excipient. In certain embodiments, the pharmaceutical composition is in the form of a tablet, capsule, pill, gel, granules, aerosol, or aqueous buffer, such as a saline or phosphate buffer, or a nanoparticle formulation, emulsion, liposome, etc. The pharmaceutical composition may also include one or more further active agents or may be administered in combination with one or more such active agent.

In a yet further embodiment there is provided methods for preparing the compounds of Formula (I) or salts thereof comprising mixing one or more starting materials with reagents under conditions such that the products are formed.

DETAILED DESCRIPTION

Terms

Figure 1:
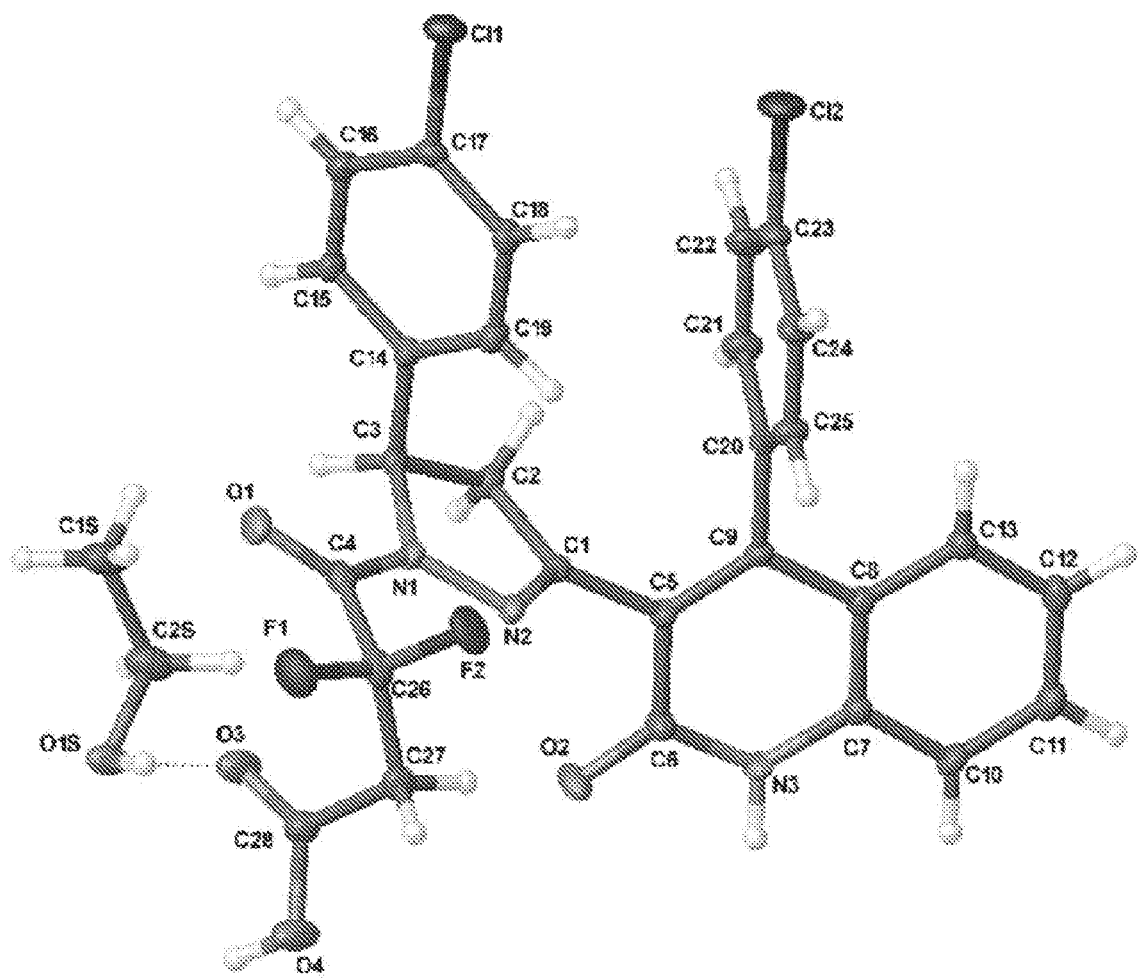
FIG. 1 shows a crystallographic structure of the R configuration of 997-74.

Before the present disclosure is described in greater detail, it is to be understood that this disclosure is not limited to embodiments described, and as such may, of course, vary. It is also to be understood that the terminology used herein is for the purpose of describing particular embodiments only and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

To the extent that any chemical formulas reported herein contain one or more chiral centers, the formulas are intended to encompass all stable stereoisomers, enantiomers, and diastereomers. It is also understood that formulas encompass all tautomeric forms.

It must be noted that, as used in the specification and the appended claims, the singular forms "a", "an", and "the" include plural referents unless the context clearly dictates otherwise.

"Subject" refers any animal, preferably a human patient, livestock, mouse model or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, "alkyl" means a noncyclic straight chain or branched, unsaturated or saturated hydrocarbon such as those containing from 1 to 20 carbon atoms. In certain embodiments, any "alkyl" disclosed herein may be a lower alkyl and a higher alkyl or any of the specific alkyl groups reported in this section. A "lower alkyl" refers to unsaturated or saturated hydrocarbons having 1 to 6 carbon atoms or 1 to 4 carbon atoms and a "higher alkyl" refers to unsaturated or saturated hydrocarbon having 6 or more carbon atoms. A "$C_8$-$C_{18}$" refers to an alkyl containing 8 to 18 carbon atoms. Likewise, a "$C_6$-$C_{22}$" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, hexadecyl, dodecyl, tetradecyl, isononyl, octadecyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like. Carbocyclyls include cycloalkyls and cycloalkenyls.

"Heterocarbocycles" or "heterocarbocyclyl" groups are carbocycles which contain from 1 to 4 heteroatoms independently selected from nitrogen, phosphorous, oxygen and sulphur which may be saturated or unsaturated (but not aromatic), monocyclic or polycyclic, and wherein the nitrogen and sulphur heteroatoms may be optionally oxidized (e.g. —S(O)—, —SO$_2$—, —N(O)—), and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

The terms "cycloalkyl" and "cycloalkenyl" refer to mono-, bi-, or tri homocyclic ring groups of 3 to 15 carbon atoms which are, respectively, fully saturated and partially unsaturated.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

The term "substituted" refers to a molecule wherein at least one hydrogen atom is replaced with a substituent. When substituted, one or more of the groups are "substituents". The molecule may be multiply substituted. In the case of an oxo substituent (=O), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted", as used herein, means that substitution is optional and therefore it is possible for the designated atom to be unsubstituted.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, adding a hydroxyl group, replacing an oxygen atom with a sulfur atom, or replacing an amino group with a hydroxyl group, oxidizing a hydroxyl group to a carbonyl group, reducing a carbonyl group to a hydroxyl group, and reducing a carbon-to-carbon double bond to an alkyl group or oxidizing a carbon-to-carbon single bond to a double bond. A derivative optionally has one or more, the same or different, substitutions. Derivatives may be prepared by any variety of synthetic methods or appropriate adaptations presented in synthetic or organic chemistry text books, such as those provided in "March's Advanced Organic Chemistry: Reactions, Mechanisms, and Structure", Wiley, 6th Edition (2007) Michael B. Smith or "Domino Reactions in Organic Synthesis", Wiley (2006) Lutz F. Tietze, hereby incorporated by reference.

Pharmaceutical Compositions Including the Compounds

Mammals, and specifically humans, suffering from schizophrenia, Parkinson's disease, depression, obsessive-compulsive disorders, neuropathic pain, stroke, traumatic brain injury, epilepsy, and other neurologic events or neurodegeneration involving NMDA receptor activation, or any of the above-described conditions, and in particular suffering from neuropathic pain, can be treated by either targeted or systemic administration, via oral, inhalation, topical, trans- or sub-mucosal, subcutaneous, parenteral, intramuscular, intravenous or transdermal administration of a composition comprising an effective amount of the compounds described herein or a pharmaceutically acceptable salt, ester or prodrug thereof, optionally in a pharmaceutically acceptable carrier. The compounds or composition is typically administered by oral administration. Alternatively, compounds can be administered by inhalation. In another embodiment, the compound is administered transdermally (for example via a slow release patch), or topically. In yet another embodiment, the compound is administered subcutaneously, intravenously, intraperitoneally, intramuscularly, parenterally, or submucosally. In any of these embodiments, the compound is administered in an effective dosage range to treat the target condition.

In one embodiment, compounds of the present invention are administered orally. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

When the compound is administered orally in the form of a dosage, tablets, pills, capsules, troches and the like, these can contain any of the following ingredients, or compounds of a similar nature: a binder (such as microcrystalline cellulose, gum tragacanth or gelatin); an excipient (such as starch or lactose), a disintegrating agent (such as alginic acid, Primogel, or corn starch); a lubricant (such as magnesium stearate or Sterotes); a glidant (such as colloidal silicon dioxide); a sweetening agent (such as sucrose or saccharin); and/or a flavoring agent (such as peppermint, methyl salicylate, or orange flavoring). When the dosage unit form is a capsule, it can contain, in addition to material of the above type, a liquid carrier (such as a fatty oil). In addition, dosage unit forms can contain various other materials which modify the physical form of the dosage unit, for example, coatings of sugar, shellac, or other enteric agents. The compound or its salts can also be administered orally as a component of an elixir, suspension, syrup, wafer, chewing gum or the like. A syrup may contain, in addition to the active compounds, a sweetening agent (such as sucrose, saccharine, etc.) and preservatives, dyes and colorings and flavors.

The compounds of the invention may also be administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate. In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or as pressure such as the dry-powder inhaler.

A parenteral preparation can be enclosed in ampoules, disposable syringes or multiple dose vials made of glass or plastic.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

If administered intravenously, carriers can be physiological saline, bacteriostatic water, Cremophor ELm (BASF, Parsippany, NJ) or phosphate buffered saline (PBS). In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Dosing

The compound is administered for a sufficient time period to alleviate the undesired symptoms and the clinical signs associated with the condition being treated. In one embodiment, the compounds are administered less than three times daily. In one embodiment, the compounds are administered in one or two doses daily. In one embodiment, the compounds are administered once daily. In some embodiments, the compounds are administered in a single oral dosage once a day. The active compound is included in the pharmaceutically acceptable carrier or diluent in an amount sufficient to deliver to a patient a therapeutic amount of compound in vivo in the absence of serious toxic effects. An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

Typical systemic dosages for the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as single daily doses. In one embodiment, the daily dose is between 10 and 500 mg/day. In another embodiment, the dose is between about 10 and 400 mg/day, or between about 10 and 300 mg/day, or between about 20 and 300 mg/day, or between about 30 and 300 mg/day, or between about 40 and 300 mg/day, or between about 50 and 300 mg/day, or between about 60 and 300 mg/day, or between about 70 and 300 mg/day, or between about 80 and 300 mg/day, or between about 90 and 300 mg/day, or between about 100 and 300 mg/day, or about 200 mg/day. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Combination Treatment

The compound can also be mixed with other active materials which do not impair the desired action, or with materials that supplement the desired action. The active compounds can be administered in conjunction, i.e. combination or alternation, with other medications used in the treatment or prevention of schizophrenia, Parkinson's disease, depression, neuropathic pain, stroke, traumatic brain injury, epilepsy, and other neurologic events or neurodegeneration involving NMDA receptor activation. In another embodiment, the compounds can be administered in conjunction (combination or alternation) with other medications used in treatment or prophylaxis of inflammatory conditions. In certain embodiments, the combination can be synergistic although in other embodiments the combination is not synergistic.

Methods of Treatment Using the Compounds

In one embodiment, the compounds are used in a method of treatment or prophylaxis of schizophrenia, Parkinson's disease, bipolar disorder, depression, anxiety, neuropsychiatric or mood disorders, obsessive-compulsive disorder, motor dysfunction, neuropathic pain, ischemic and hemorrhagic stroke, subarachnoid hemorrhage, cerebral vasospasm, ischemia, hypoxia, Alzheimer's disease, presenile dementia, amyotrophic lateral sclerosis (ALS), Huntington's chorea, traumatic brain injury, epilepsy, and other neurologic events, neurocognitive disorders, tardive dyskinesia, motor disorders, mood disorders or neurodegeneration involving NMDA receptor activation comprising administering to a host in need thereof an effective amount of a compound described herein, optionally in a pharmaceutically acceptable carrier. The compounds can be administered, alone or in a pharmaceutically acceptable carrier, to a patient suffering from, or at risk of developing the various disorders, to treat, prevent, or reduce the symptoms of or cognitive deficits associated with the various disorders.

The compounds described herein can also generally be used to treat neurologic events and neurodegeneration, whether or not such neurologic event or neurodegeneration is associated with NMDA receptor activation.

In some embodiments, the compounds are used to treat or prevent stroke or stroke damage, and can be administered under emergency care for a stroke, for maintenance treatment of stroke, and/or for rehabilitation of stroke.

In other embodiments, the compounds are used to provide cognitive enhancement, in normal or cognitively deficient individuals.

In one embodiment, methods are provided to treat patients with ischemic injury or hypoxia, or prevent or treat the neuronal toxicity associated with ischemic injury or hypoxia, by administering a compound or composition described herein. In one aspect of this embodiment, the ischemic injury is vasospasm after subarachnoid hemorrhage.

A subarachnoid hemorrhage refers to an abnormal condition in which blood collects beneath the arachnoid mater, a membrane that covers the brain. This area, called the subarachnoid space, normally contains cerebrospinal fluid. The accumulation of blood in the subarachnoid space, and the vasospasm of the vessels which results from it, can lead to stroke, seizures, and other complications. The methods and compounds described herein can be used to treat patients experiencing a subarachnoid hemorrhage. In one embodiment, the methods and compounds described herein can be used to limit the toxic effects of hemorrhage, including, for example, stroke and/or ischemia that can result from the subarachnoid hemorrhage. In a particular embodiment, the methods and compounds described herein can be used to treat patients with traumatic subarachnoid hemorrhage. On one embodiment, the traumatic subarachnoid hemorrhage can be due to a head injury. In another embodiment, the patients can have a spontaneous subarachnoid hemorrhage.

In other embodiments, the ischemic injury is selected from, but not limited to, one of the following: traumatic brain injury, cognitive deficit after bypass surgery, cognitive deficit after carotid angioplasty; and/or neonatal ischemia following hypothermic circulatory arrest.

In another embodiment, methods are provided to treat patients with brain tumors, such as gliomas, by administering a compound selected according to the methods or processes described herein.

Further, compounds selected according to the methods or processes described herein can be used prophylactically to prevent or protect against such diseases or neurological conditions, such as those described herein. In one embodiment, patients with a predisposition for an ischemic event, such as a genetic predisposition, can be treated prophylactically with the methods and compounds described herein. In another embodiment, patients that exhibit vasospasms can be treated prophylactically with the methods and compounds described herein. In a further embodiment, patients that have undergone cardiac bypass surgery can be treated prophylactically with the methods and compounds described herein.

In one embodiment, methods are provided to treat patients with ischemic injury or hypoxia, or prevent or treat the neuronal toxicity associated with ischemic injury or hypoxia, by administering a compound selected according to the methods described herein.

In another embodiment, methods are provided to treat patients with neuropathic pain or related disorders by administering a compound selected according to the methods or processes described herein. In certain embodiments, the neuropathic pain or related disorder can be selected from the group including, but not limited to: peripheral diabetic neuropathy, postherpetic neuralgia, complex regional pain syndromes, peripheral neuropathies, chemotherapy-induced neuropathic pain, cancer neuropathic pain, neuropathic low back pain, HIV neuropathic pain, trigeminal neuralgia and/or central post-stroke pain.

Neuropathic pain can be associated with signals generated ectopically and often in the absence of ongoing noxious events by pathologic processes in the peripheral or central nervous system. Further, the compounds and methods described herein can be used to treat neuropathic pain resulting from peripheral or central nervous system pathologic events, including, but not limited to trauma, ischemia; infections or from ongoing metabolic or toxic diseases, infections or endocrinologic disorders, including, but not limited to, diabetes mellitus, diabetic neuropathy, amyloidosis, amyloid polyneuropathy (primary and familial), neuropathies with monoclonal proteins, vasculitic neuropathy, HIV infection, herpes zoster shingles and/or postherpetic neuralgia; neuropathy associated with Guillain-Barre syndrome; neuropathy associated with Fabry's disease; entrapment due to anatomic abnormalities; trigeminal and other CNS neuralgias; malignancies; inflammatory conditions or autoimmune disorders, including, but not limited to, demyelinating inflammatory disorders, rheumatoid arthritis, systemic lupus erythematosus, Sjogren's syndrome; and cryptogenic causes, including, but not limited to idiopathic distal small-fiber neuropathy. Other causes of neuropathic pain that can be treated according to the methods and compositions described herein include, but are not limited to, exposure to toxins or drugs (such as arsenic, thallium, alcohol, vincristine, cisplatin and dideoxynucleosides), dietary or absorption abnormalities, immuno-globulinemias, hereditary abnormalities and amputations (including mastectomy). Neuropathic pain can also result from compression of nerve fibers, such as radiculopathies and carpal tunnel syndrome.

The compounds can also be used to treat the following diseases or neurological conditions, including, but not limited to: chronic nerve injury, chronic pain syndromes, such as, but not limited to ischemia following transient or permanent vessel occlusion, seizures, spreading depression, restless leg syndrome, hypocapnia, hypercapnia, diabetic ketoacidosis, fetal asphyxia, spinal cord injury, status epilepticus, concussion, migraine, hypocapnia, hyperventilation, lactic acidosis, fetal asphyxia during parturition, and/or retinopathies by administering a compound selected according to the methods or processes described herein.

In one embodiment, the use of the compounds of the invention reduces symptoms of neuropathic pain, stroke, traumatic brain injury, epilepsy, and other neurologic events or neurodegeneration resulting from NMDA receptor activation.

In all of these embodiments, the methods involve administering a compound of Formula (I) or a pharmaceutically acceptable salt, ester, or derivative thereof, or a pharmaceutical composition thereof.

EXAMPLES

The present disclosure will now be described in more detail with reference to the following non-limiting examples. It should be noted that the particular assays used in the examples section are designed to provide an indication of activity.

The present disclosure began with the synthesis of dihydroquinolone pyrazoline scaffolds having a carboxylic acid or alcohol group as a terminal moiety, with an additional fluorine group on an acyl chain. The general synthetic procedures of target compounds are shown in the following schemes.

Commercially available isatoic anhydride 1 was reacted with dimethylhydroxylamine to give the Weinreb amide 2 in high yield. Then a 1:1 mixture of compound 2 and an appropriate bromobenzene was treated with two equivalents of n-butyllithium via a lithium-halogen exchange reaction to yield benzophenone 3 [79]. Benzophenone 3 was condensed with ethyl acetoacetate to yield quinolone derivative 4 [80]. The resultant methyl ketone 4 was treated with 4-chlorobenzaldehyde via a base-catalyzed condensation to yield the α,β-unsaturated ketone 5 [81]. Utilizing microwave irradiation, the ketone 5 was treated with hydrazine monohydrate to yield the pyrazoline amine 6 (Scheme 1) [77].

Scheme 1. Synthesis of dihydroquinolone pyrazoline amines

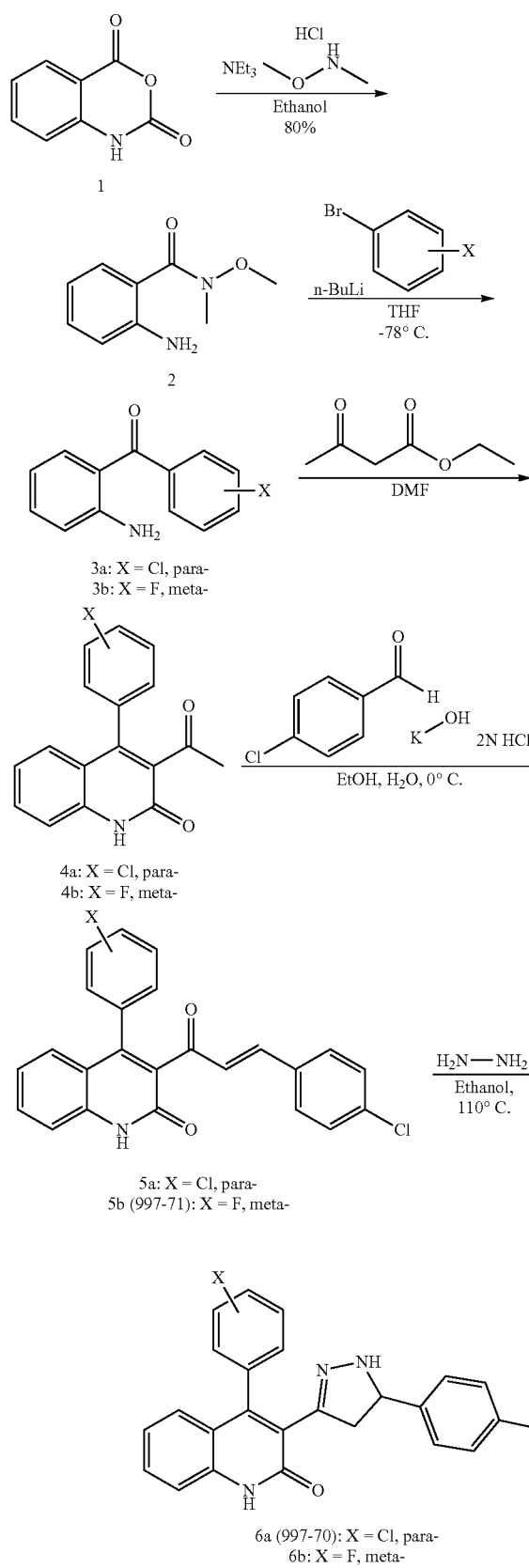

5a: X = Cl, para-
5b (997-71): X = F, meta- 6a (997-70): X = Cl, para-
6b: X = F, meta- The acyl chain component can be synthesized separately. Commercially available 2,2-difluorosuccinic acid 7 and trifluoroacetic anhydride (TFAA) were refluxed in isopropyl acetate (i-PrOAc) to yield 2,2-difluorosuccinic anhydride compound 8 [82]. The anhydride 8 was reacted with absolute ethanol overnight and then treated with oxalyl chloride to yield acetyl chloride 10 after kugelrohr distillation [83,84] (Scheme 2).

Scheme 2. Synthesis of acyl chains

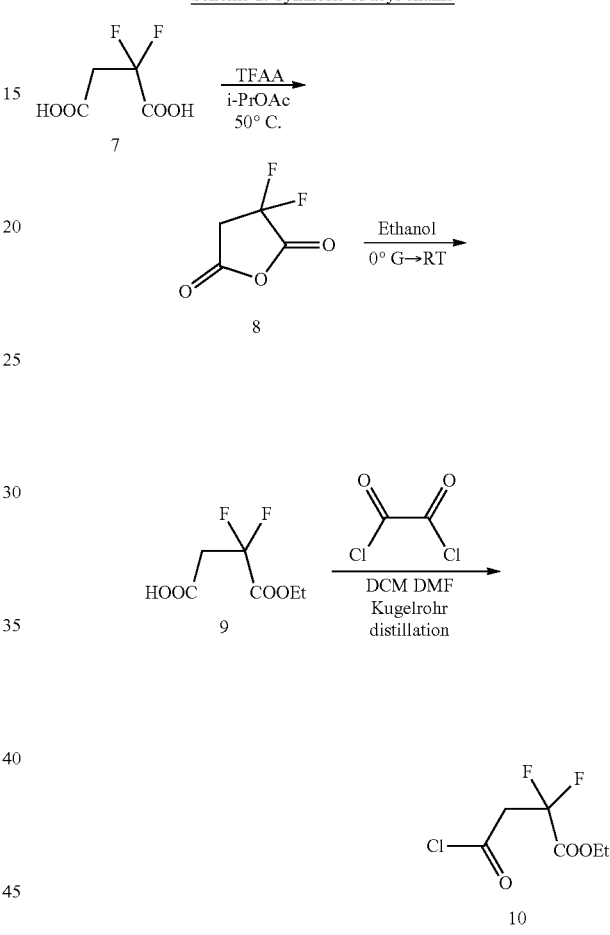

After synthesis of pyrazoline amine 6 and acyl chain precursors 8 and 10, the pyrazoline amine 6 selectively attacks the more electrophilic carboxyl group of 10 to yield 997-65 and 997-66, respectively [77]. Esters 997-65 and 997-66 were further reduced with sodium borohydride to yield 2,2-difluoro-substituted alcohols 997-67 and 997-68 [85]. Esters 997-65 and 997-66 were also reduced with trimethyltin hydroxide to give 2,2-difluoro-substituted carboxylic acids 997-69 and 997-114 [86]. Alternative pyrazoline amine 6 reacts directly with 2,2-difluorosuccinic anhydride 8 at room temperature giving 3,3-difluoro-substituted carboxylic acid 997-74. Then, 997-74 was further reduced by borane dimethyl sulfide, to yield 3,3-difluoro-substituted alcohol 997-75 [77] (Scheme 3).

Scheme 3. Synthesis of acylated quinolone pyrazoline products

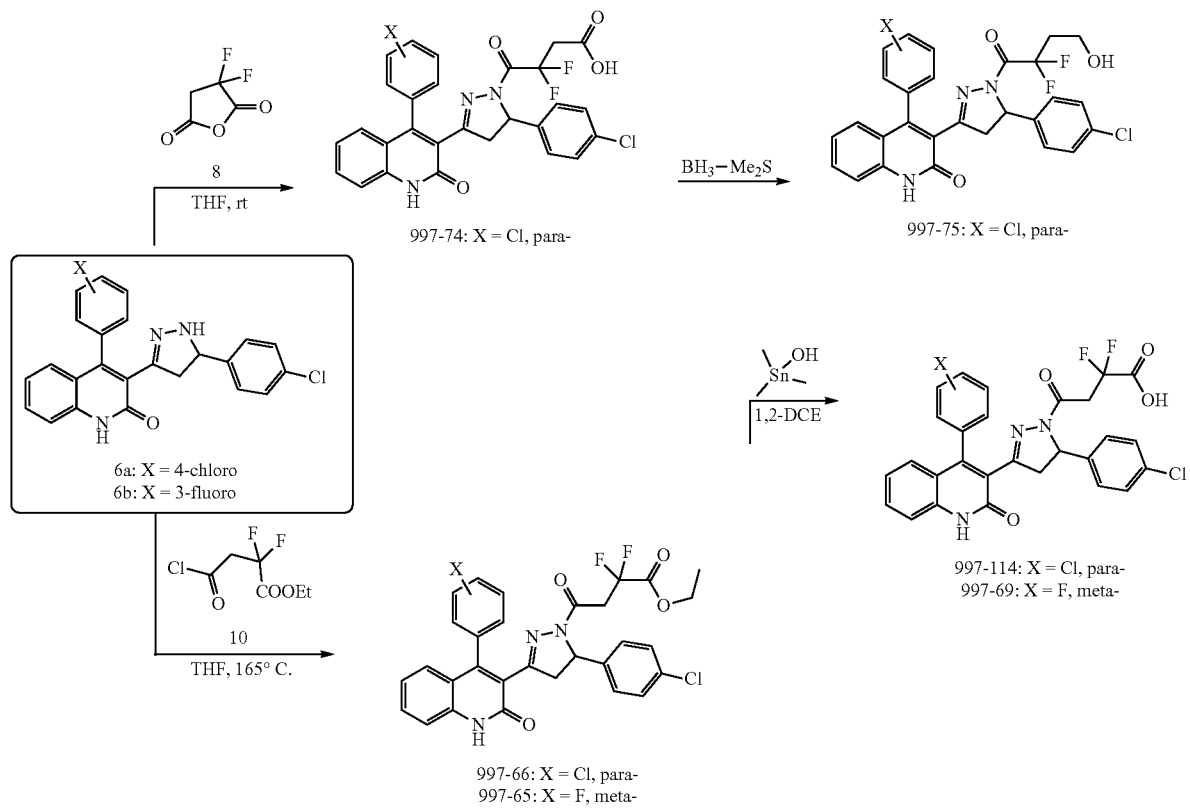

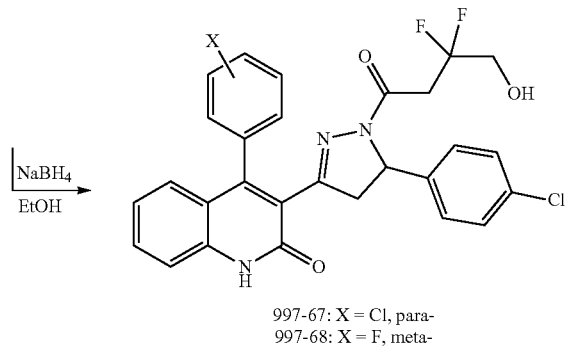

Instead of adding two fluorines on the acyl chain, monofluorine substituted compound 997-101 was synthesized to evaluate the activity and selectivity at the GluN2D-containing receptor. The acyl chain component was synthesized through two steps. Starting with commercially available 2,2-difluorosuccinic acid 7, 2-fluoromaleic acid 11 was synthesized via elimination with sodium hydroxide. Then compound 11 was refluxed with trifluoroacetic anhydride in isopropyl acetate to yield fluoromaleic anhydride 12 [82]. The intermediate pyrazoline amine 6 was reacted with anhydride 12 to yield 997-101 [77] (Scheme 4).

Scheme 4. Synthesis of 997-101

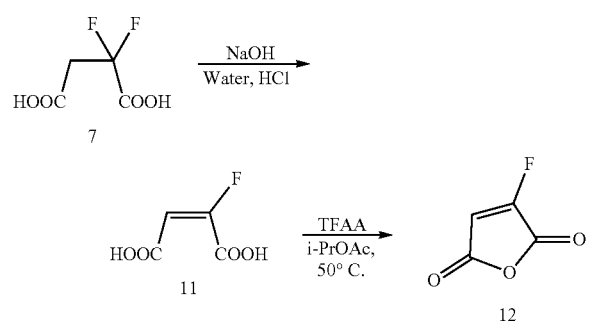

-continued

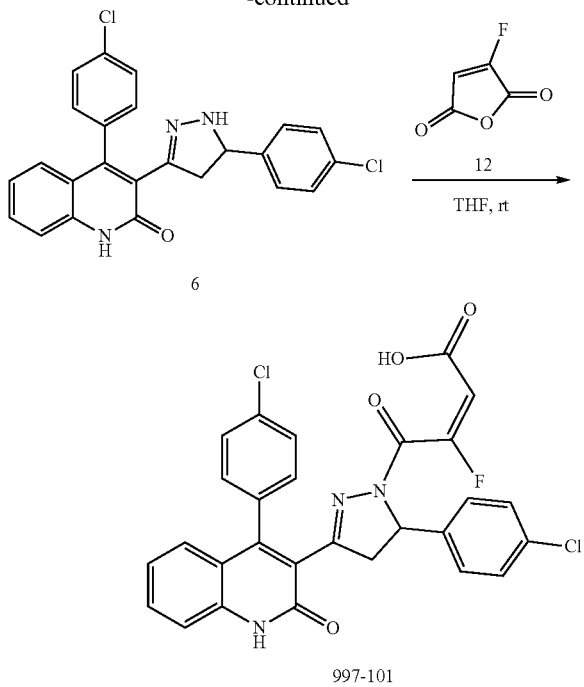

997-101

Amides 997-96 and 997-115, which are regarded as the bio-isosteres of carboxylic acids, were also synthesized via two steps. Carboxylic acids 997-74 and 997-114 were activated by oxalyl chloride to yield acetyl chlorides and then reacted with ammonia solution to yield 997-96 and 997-115 (Scheme 5).

Scheme 5. Synthesis of amides 997-96 and 997-115

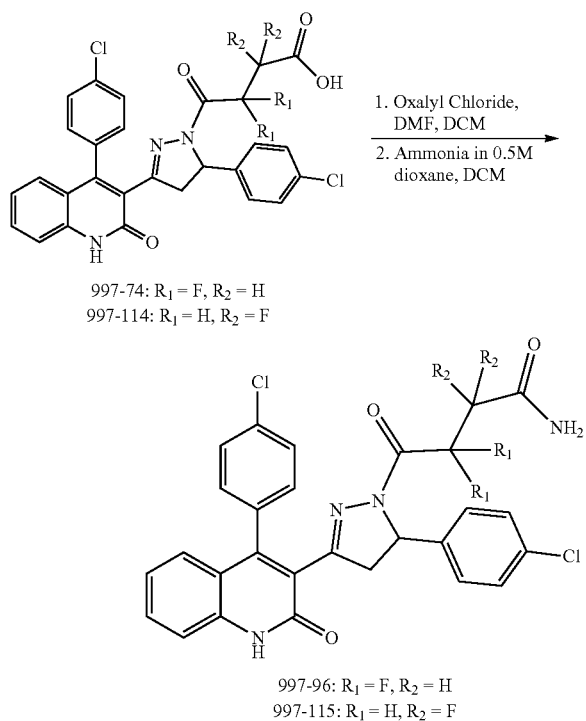

997-74: $R_1 = F, R_2 = H$
997-114: $R_1 = H, R_2 = F$ 997-96: $R_1 = F, R_2 = H$
997-115: $R_1 = H, R_2 = F$

All target compounds were evaluated for activity by the Traynelis laboratory at Emory University using two-electrode voltage-clamp recordings performed in *Xenopus laevis* oocytes expressing recombinant GluN2A-D subunits [77] (Table 1). The intermediates pyrazoline amine 997-70 and α,β-unsaturated ketone 997-71 were inactive at all receptors. Two ester compounds 997-65 and 997-66 also performed no inhibition at GluN2A to GluN2D receptors. With di-fluorine substitution, alcohol compounds 997-67,-68 and -75 showed activity only at GluN2C and GluN2D receptors with $IC_{50}$ values ranging from 0.8 μM to 2.0 μM. Based on the $IC_{50}$ value, compound 997-67 with a para-chloro substitution on the top ring was more potent at GluN2C/D subunits in comparison to meta-fluoro substituted 997-68. Compound 997-75 with the difluoro-substitution near the amide group showed much poorer potency than 997-67 and 997-68. Notably, in the early project, the potency at GluN2C/D-containing receptors was mostly 3-10 μM. Consequently, for the compounds that Acker et al. already published, it was necessary to increase the concentration to 100 μM when collecting data for a concentration effect curve. As the project moved positively, the potency of compounds that were synthesized in this disclosure were often under 1 μM. As the potency increased, it was less demanding to test compounds at concentration over 30 μM. Therefore, under this condition, we can only conclude that compound 997-67 remained potent at GluN2C/D-containing receptors, but its selectivity over GluN2A- and GluN2B-containing receptors could not be compared to 997-57. Compound 2,2-difluoro-substituted carboxylic acid 997-69 with a meta-fluoro substitution on the top ring exhibited similar activity and selectivity at GluN2C/D subunits. Compound 997-114, with a para-chloro substitution on the top ring and 2,2-difluoro-substituted carboxylic acid, performed better inhibition with an $IC_{50}$ value of 170 nM but poorer selectivity at GluN2D over GluN2A/B-containing receptors in comparison to no fluoro substitution compound 997-23. Surprisingly, compound 997-74, with difluoro-substitution adjacent to the amide group, exhibited an improvement of potency at GluN2C- and GluN2D-containing receptors with $IC_{50}$ values of 390 nM and 50 nM respectively, and was selective approximately 220-fold at the GluN2D- over the GluN2A-containing receptor. Although compound 997-101, which is the cis-configuration of mono-fluoro maleic acid, retained activity at the GluN2D receptor ($IC_{50}$=60 nM) in comparison to 997-74, the potency of GluN2A- and GluN2C-containing receptors were both increased, which consequently decreased the selectivity at GluN2D over GluN2A from 220-fold to 50-fold. Finally, replacing the carboxylic acid to the bio-isostere amide yielded compounds 997-96 and 997-115, which dropped the potency 2- to 4-fold in comparison to their corresponding acids 997-74 and 997-114.

TABLE 1

Acyl chain modifications.

| 997- | 2A $IC_{50}$ 2D $IC_{50}$ | 2B $IC_{50}$ 2D $IC_{50}$ | GluN2A $IC_{50}$ (μM) | GluN2B $IC_{50}$ (μM) | GluN2C $IC_{50}$ (μM) | GluN2D $IC_{50}$ (μM) |
|---|---|---|---|---|---|---|
| 65 | — | — | NE | NE | NE | NE |
| 66 | — | — | NE | NE | NE | NE |
| 67 | — | — | NE | NE | 1.6 | 0.8 |
| 68 | — | — | NE | NE | 4.3 | 1.4 |
| 69 | 56 | 96 | 28 | 48 | 0.6 | 0.5 |
| 70 | — | — | NE | NE | NE | NE |

TABLE 1-continued

Acyl chain modifications.

| 997- | 2A IC$_{50}$ 2D IC$_{50}$ | 2B IC$_{50}$ 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|
| 71 | — | — | NE | NE | NE | NE |
| 74 | 220 | 138 | 11 | 6.9 | 0.39 | 0.05 |
| 75 | — | — | NE | NE | 17 | 2 |
| 96 | 150 | 14 | 30 | 2.8 | 0.5 | 0.2 |
| 101 | 50 | 183 | 3 | 11 | 0.07 | 0.06 |
| 114 | 33 | 48 | 5.67 | 8.15 | 0.338 | 0.17 |
| 115 | — | — | NE | NE | 1.44 | 0.343 |

IC$_{50}$ values were obtained by fitting the Hill equation to the average composite concentration-effect curves.
Data were from 4-13 oocytes between 1-2 frogs.
NE indicates less than 50% inhibition at 30 μM.

Based on the above SAR results, three potent racemic compounds 997-67, 997-74, and 997-90 were selected to separate their enantiomers via reverse phase chiral chromatography by using an OD-RH column [77] (Scheme 6).

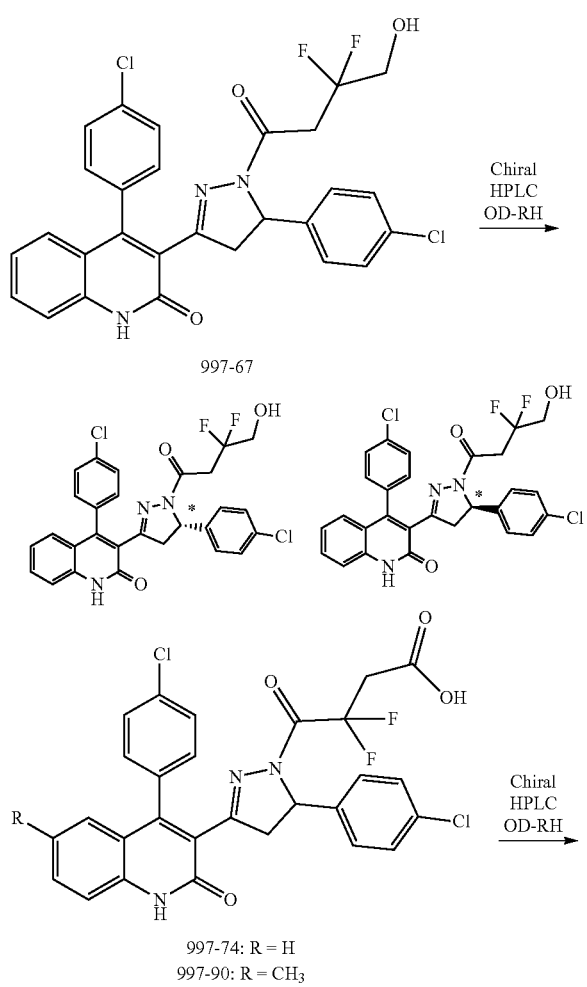

Scheme 6. Enantiomer separation 997-67

997-74: R = H
997-90: R = CH$_3$

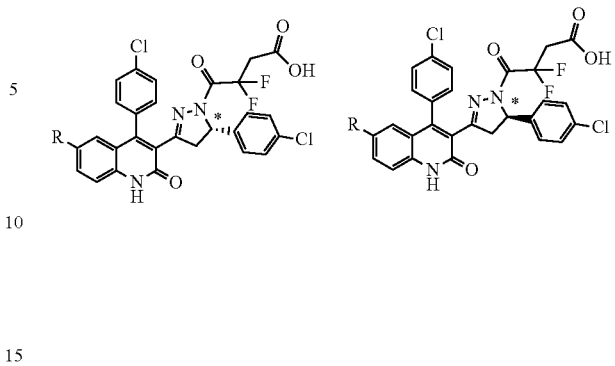

Evaluation of the purified enantiomers indicated that all three (−)-enantiomers slightly increased the selectivity and activity at GluN2C- and GluN2D-containing receptors over racemic compounds. (−)-997-67 is 6-fold more potent than (+)-997-67 at the GluN2D subunit, while (−)-997-74 is 85-fold more active than (+)-997-74 at the GluN2D receptors (Table 2).

TABLE 2

Stereoselectivity for the purified enantiomers.

| 997- | GluN2A IC$_{50}$ (μM) | GluN2B IC$_{50}$ (μM) | GluN2C IC$_{50}$ (μM) | GluN2D IC$_{50}$ (μM) |
|---|---|---|---|---|
| 67 | NE | NE | 1.6 | 0.8 |
| (−)-67 | NE | NE | 1.4 | 0.62 |
| (+)-67 | NE | NE | 8.5 | 3.6 |
| 74 | 11 | 6.9 | 0.39 | 0.05 |
| (−)-74 | NE | NE | 0.094 | 0.046 |
| (+)-74 | NE | NE | 3.4 | 3.9 |
| 90 | 3 | 3 | 0.4 | 0.2 |
| (−)-90 | 1.9 | 1.9 | 0.2 | 0.13 |
| (+)-90 | 4.1 | 1.8 | 2.1 | <1 |

The absolute stereochemistry of (+) 997-74 was assigned via X-ray crystallography as the R configuration (FIG. 1). According to this information, we can conclude that S enantiomers of the 997-series were more potent than corresponding R enantiomers and racemic compounds. (S)-997-74 was the most active compound thus far with an IC$_{50}$ value of 46 nM.

A-Phenyl Ring Modification

After exploring the effect of different acyl chains, the A-phenyl ring was modified next. Eleven compounds were synthesized by keeping the B-phenyl ring and C-quinolone ring constant. The acyl chains of these compounds were either a carboxylic acid or a difluoro-substituted carboxylic acid. The synthetic route was similar to that shown above. Starting with isatoic anhydride, quinolone derivative 4a was formed via three steps [79,80]. The resultant methyl ketones 4a were treated with appropriate carbaldehyde via a base-catalyzed condensation to yield the α,β-unsaturated ketones [81]. Utilizing microwave irradiation, the ketones were reacted with hydrazine monohydrate to yield the pyrazoline amines. The pyrazoline amines were then functionalized with succinic anhydride or 2,2-difluorosuccinic anhydride to yield compounds 997-79, -80, -83, -88, -92, -104, -110, -111, -112 and -113 [77] (Scheme 7).

Scheme 7. Synthesis of 997-series with different A ring modifications

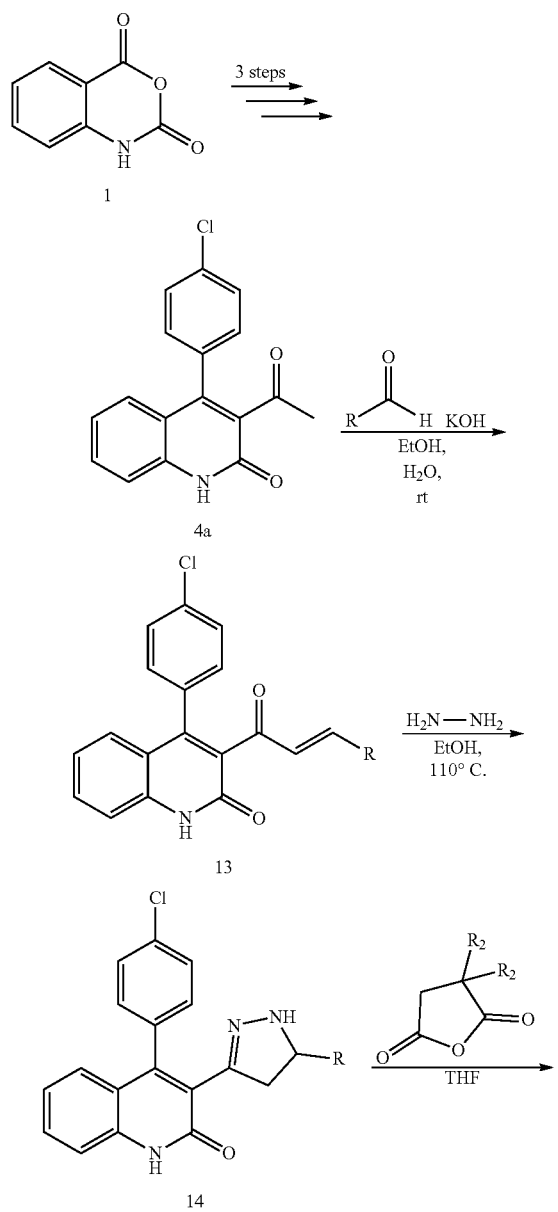

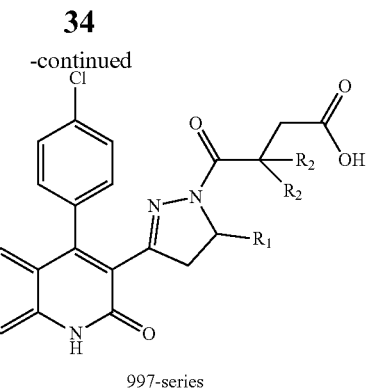

997-series

All target compounds were evaluated for activity by the Traynelis laboratory (Emory) using two-electrode voltage-clamp recordings. Compared with the pyrazoline amine 997-70, which was inactive at the receptors, the pyrazoline amine 997-78 showed weak potency at GluN2B-, GluN2C-, and GluN2D-containing receptors (Table 3). However, compound 997-79 was inactive at all receptors after adding the acyl chain to 997-78. Compounds 997-80, 997-83, and 997-88 were also inactive at all receptors, while compound 997-92 with a para-chloro substitution showed weak activity at the GluN2C- and GluN2D-containing receptors. Compound 997-104 with a smaller halogen substitution, fluorine, decreased the potency 16-fold at the GluN2D-containing receptor as well as lowered the selectivity over the GluN2B-containing receptor in comparison to 997-74. 2-Chloro substituted thiophenes, 997-110 and 997-111, were synthesized and evaluated. Compound 997-110 with a difluoro-substitution on the acyl chain performed with an $IC_{50}$ value of 160 nM, which is 3-fold less potent than 997-74. However, 2-chlorothiophene improved the GluN2D-containing receptor selectivity over GluN2B-containing receptor to 625-fold. Compounds 997-112 and 997-113 with a trifluoromethyl substitution, which showed better hydrophobicity and electron-withdrawing properties than chlorine, were synthesized with and without difluoro substitution on the acyl chain. Compound 997-112 without a difluoro substitution performed with better activity and selectivity at GluN2D-containing receptor in comparison to 997-23, while compound 997-113 with difluoro-substitution resulted in a lower inhibition and selectivity at GluN2D-containing receptor than compound 997-74 (Table 3). Therefore, the halogen substitution on the para position of the A ring may be an important functionality to increase the potency at the GluN2C/D-containing receptors, and the thiophene ring may play a crucial role on improving the selectivity at GluN2D-containing receptors over GluN2B-containing receptors.

TABLE 3

A ring modifications.

| 997- | $R_1$ | $R_2$ | 2B $IC_{50}$ 2D $IC_{50}$ | GluN2A $IC_{50}$ (µM) | GluN2B $IC_{50}$ (µM) | GluN2C $IC_{50}$ (µM) | GluN2D $IC_{50}$ (µM) |
|---|---|---|---|---|---|---|---|
| 78 | 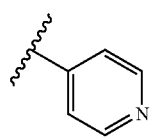 [SMILES: *c1ccncc1] | — | 3 | NE | 54 | 20 | 19 |

TABLE 3-continued

A ring modifications.

| 997- | R₁ | R₂ | 2B IC$_{50}$ 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|
| 79 | 4-pyridyl | H | — | NE | NE | NE | NE |
| 80 | 2-pyrazinyl | H | — | NE | NE | NE | NE |
| 83 | 3-pyridyl | H | — | NE | NE | NE | NE |
| 88 | 3-Cl-4-pyridyl | H | — | NE | NE | NE | NE |
| 92 | 6-Cl-3-pyridyl | H | — | NE | NE | 8 | 8 |
| 104 | 4-F-phenyl | F | 37 | 20 | 30 | 1.6 | 0.81 |
| 110 | 5-Cl-2-thienyl | F | 625 | 30 | 100 | 0.43 | 0.16 |
| 111 | 5-Cl-2-thienyl | H | 43 | 21 | 34 | 1.3 | 0.8 |
| 112 | 4-CF₃-phenyl | H | 100 | 13 | 20 | 0.35 | 0.2 |

TABLE 3-continued

A ring modifications.

| 997- | $R_1$ | $R_2$ | 2B IC$_{50}$ 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|
| 113 | 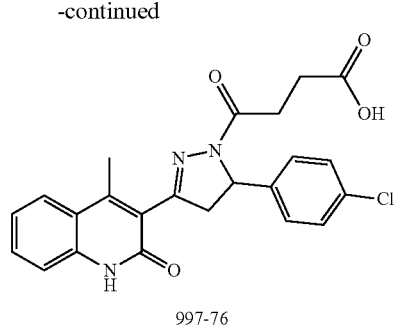 | F | 36 | 2.3 | 2.9 | 0.17 | 0.08 |

Data were from 4-13 oocytes between 1-2 frogs.
NE indicates less than 50% inhibition at 30 μM.

B-Phenyl Ring Modification

To explore the necessity of the top B-phenyl ring, compound 997-76 was synthesized first. Commercially available 2-aminoacetophenone was treated with ethyl acetoacetate, utilizing microwave irradiation, to yield the quinolone derivative [80]. The resultant methyl ketone was treated with 4-chlorobenzaldehyde via abase-catalyzed condensation to yield the α,β-unsaturated ketones. Utilizing microwave irradiation, the unsaturated ketone was reacted with hydrazine monohydrate to yield compound 997-77. The pyrazoline amine 997-77 was treated with succinic anhydride to yield the final compound 997-76 [77] (Scheme 8). This compound was inactive at all receptors (Table 4).

Scheme 8. Synthesis of 997-76 and 997-77

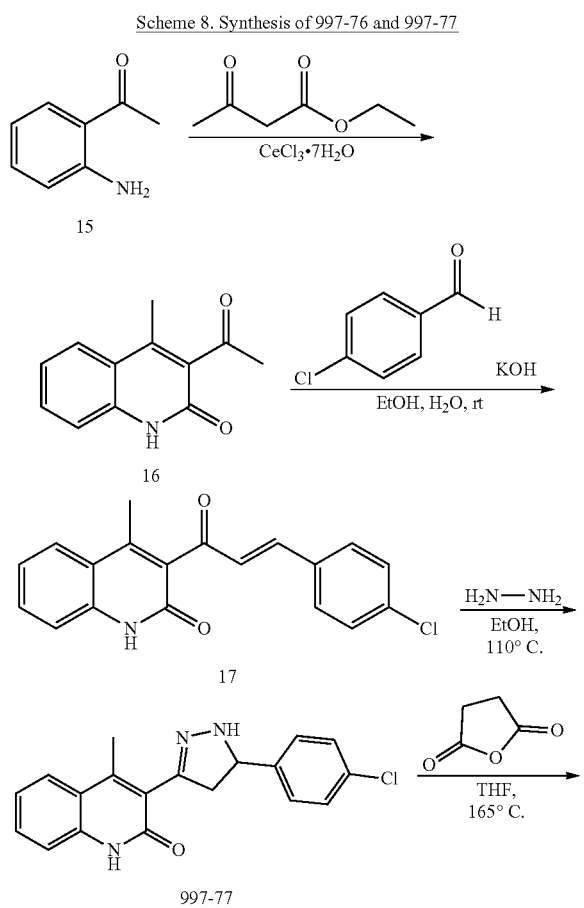

997-76

By following the same procedures as shown below, the top ring was also modified with pyridine, 2-chlorothiophen, and para-fluorophenyl analogs. Commercially available 4-bromopyridine, 2-bromo-5-chlorothiophene, and 1-bromo-4-fluorobenzene were used in the second step (Scheme 9). All these compounds were evaluated for activity using two-electrode voltage-clamp recordings. In comparison to compound 997-23, compound 997-82 showed poor activity at GluN2C- and GluN2D-containing receptors with IC$_{50}$ values of 15 μM and 8.1 μM respectively, while compound 997-108 with a thiophene retained or slightly increased its activity and selectivity at GluN2D- over GluN2A/B-containing receptors (Table 4). Difluoro substituted compound 997-109 improved the IC$_{50}$ value to 100 nM at the GluN2D-containing receptor but decreased the selectivity over the GluN2A- and GluN2B-containing receptors. Compounds 997-103 and 997-105 with a fluoro substitution on both A-phenyl ring and B-phenyl ring dropped the inhibition potency to 3-5 μM regardless of whether there was difluoro substitution on the acyl chain or not. These results confirmed the conclusion to that para-chloro and chlorothiophene are two favorable substitutions on the top ring for improving the potency at the GluN2D subunit.

Scheme 9. Synthesis of 997-series with top B-phenyl ring modifications

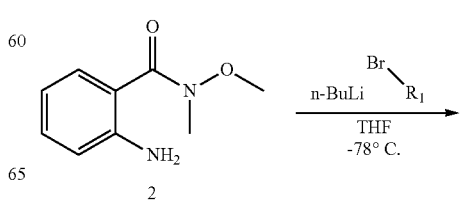

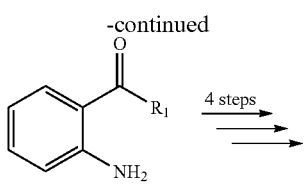

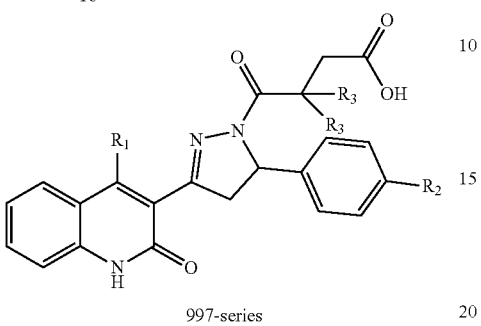

997-series

TABLE 4

B-phenyl ring modifications.

| 997- | R1 | R2 | R3 | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|
| 76 | — | — | — | NE | NE | NE | NE |
| 77 | — | — | — | NE | NE | NE | NE |
| 82 | (4-pyridyl) | Cl | H | NE | NE | 15 | 8.1 |
| 103 | (4-fluorophenyl) | F | F | NE | NE | 7 | 3.1 |

TABLE 4-continued

B-phenyl ring modifications.

| 997- | R1 | R2 | R3 | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|
| 105 | (4-fluorophenyl) | F | H | NE | NE | 6.7 | 5.1 |
| 108 | (5-chlorothien-2-yl) | Cl | H | 13 | 23 | 0.67 | 0.4 |
| 109 | (5-chlorothien-2-yl) | Cl | F | 2.6 | 4 | 0.28 | 0.1 |

Data were from 4-13 oocytes between 1-2 frogs.
NE indicates less than 50% inhibition at 30 μM.

Quinolone Ring Modification

Two compounds with a methyl group were synthesized to improve the selectivity. Starting with 2-amino-5-methylbenzoic acid, triphosgene was added to form anhydride b [77]. Then 1b underwent 6 or 7 steps to give 997-90 and 997-91 (Scheme 10). Unexpectedly, for the difluoro-substituted compounds, the methyl group did not increase selectivity but instead decreased it. Compound 997-102 with a fluoro substitution on the quinolone ring performed with moderate potency at the GluN2D-containing receptor with an IC$_{50}$ value of 400 nM and poor selectivity over the GluN2A- and GluN2B-containing receptors (see Table 5). Based on these results, substitutions on the quinolone ring did not improve either the activity or selectivity at the GluN2D-containing receptor.

Scheme 10. Synthesis of 997-90, 997-91, and 997-102

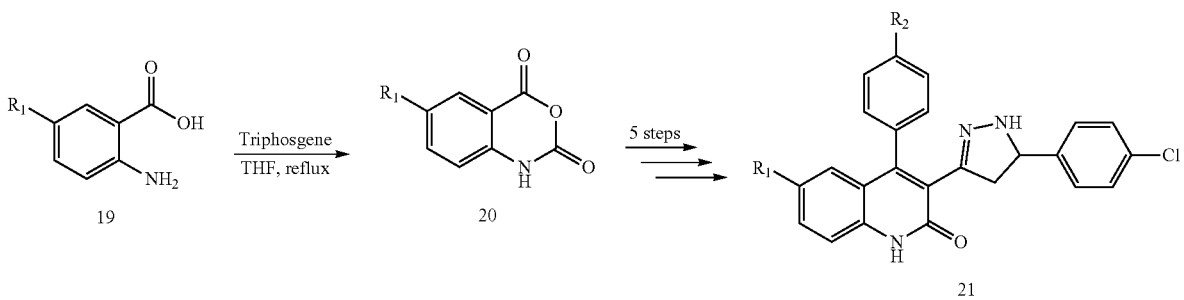

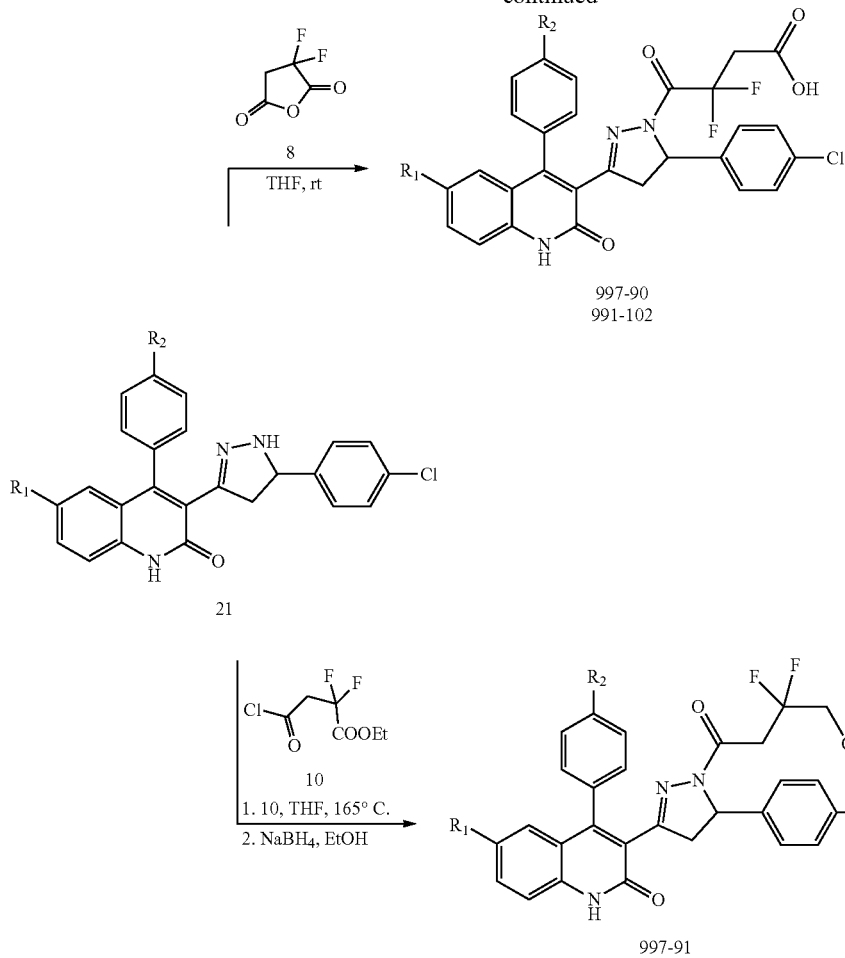

997-90
991-102

21

997-91

TABLE 5

Quinolone ring modification (1)

| 997- | R1 | R2 | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|
| 90 | Me | Cl | 3 | 3 | 0.4 | 0.2 |
| 91 | Me | Cl | NE | NE | 7.1 | 4.4 |
| 102 | F | F | 5.9 | 7.3 | 1 | 0.4 |

Data were from 4-13 oocytes between 1-2 frogs.
NE indicates less than 50% inhibition at 30 μM.

Compounds 997-97 and 997-98 with thioamide were synthesized to explore the functionality of amide group in the quinolone ring. Pyrazoline amine 6 was converted to thioamide-containing compound 22 with Lawesson's reagent in toluene via microwave irradiation [90]. Then the compound 22 was forwarded to the final compound 997-97 and 997-98 (Scheme 11). Both the activity and selectivity were improved by adding the difluoro substitution. Compound 997-98 showed to be less potent at the GluN2D subunit with an IC$_{50}$ value of 140 nM in comparison to the most active compound 997-74, with an IC$_{50}$ value of 50 nM. However, compound 997-98 was inactive at the GluN2A- and GluN2B-containing receptors, which resulted in better selectivity (Table 6).

Scheme 11.
Synthesis of thioamide-containing compound 997-97 and 997-98

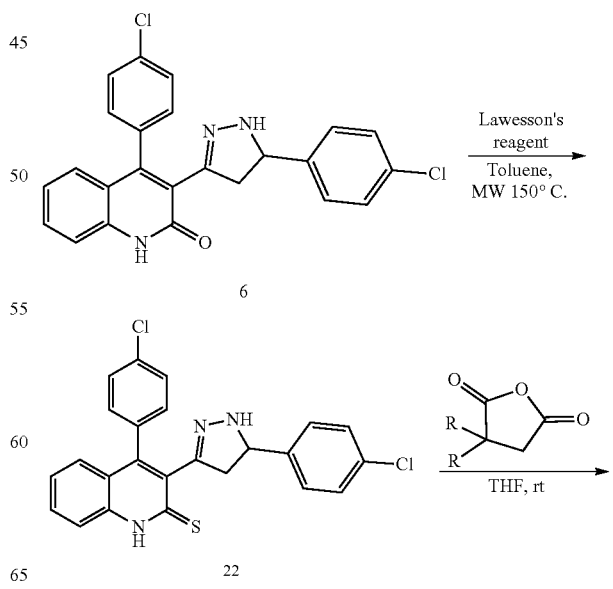

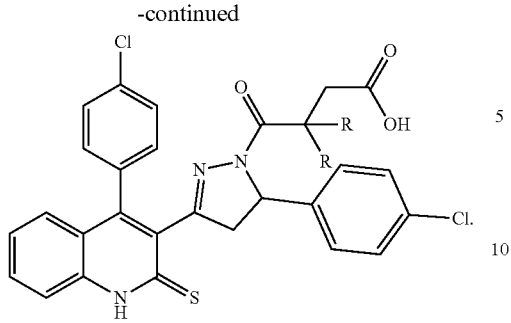

997-97: R = H;
997-98: R = F

TABLE 6

Quinolone ring modification (2)

| 997- | R | 2A IC$_{50}$ 2D IC$_{50}$ | 2B IC$_{50}$ 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|
| 97 | H | 46 | 86 | 16 | 30 | 0.48 | 0.35 |
| 98 | F | — | — | NE | NE | 0.44 | 0.14 |

Data were from 4-13 oocytes between 1-2 frogs.
NE indicates less than 50% inhibition at 30 μM.

SAR Results of 997-Series with 997-95 Scaffold and Development of 997-95 Scaffold Generally, as a CNS drug, a large molecular weight can lower the capacity to cross the BBB. Therefore, to provide for BBB penetration, the size of the 997-series was diminished. One direct way to minimizing the size is simply cut one ring off. 997-95 with a phenyl group instead of a quinolone moiety was synthesized first. 2'-Bromoacetophenone and 4-chlorophenylboronic acid were refluxed via Suzuki-Miyaura cross-coupling to yield a methyl ketone. The resultant methyl ketone were treated with 4-chlorobenzaldehyde via a base-catalyzed condensation to yield the α,β-unsaturated ketone [81]. Utilizing microwave irradiation, the ketone was treated with hydrazine monohydrate to yield the pyrazoline amine. The pyrazoline amine was then functionalized with succinic anhydride or 2,2-difluorosuccinic anhydride to yield compounds 997-95 and 997-99 [77] (Scheme 12).

Scheme 12. Synthesis of 997-95 and 997-99

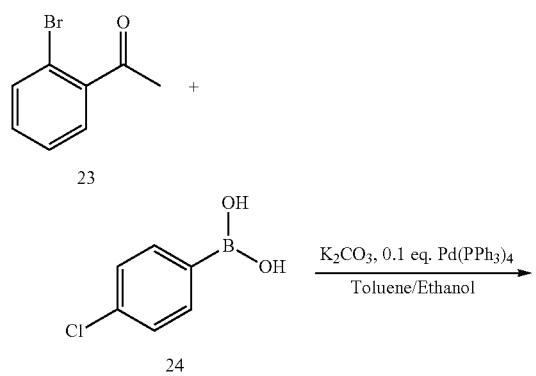

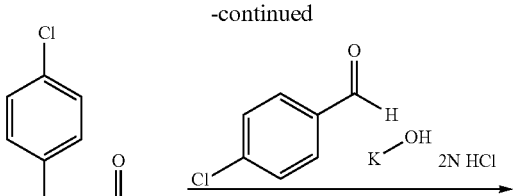

997-95: R = F
997-99: R = H

All target compounds were evaluated for activity using two-electrode voltage-clamp recordings. Compound 997-95 with a phenyl group instead of a quinolone moiety showed an IC$_{50}$ value equal to 4.8 μM and 6.2 μM at GuN2C- and GuN2D-containing receptors, respectively (Table 7). Although 997-95 was less potent than 997-74, it was still active and had a lower molecular weight (from 570 g/mol to 503 g/mol). Therefore, 997-95 was treated as a novel scaffold for further optimization. Compound 997-99 without a difluoro-substitution dropped the activity to 16 μM and 12 μM at the GluN2C- and GluN2D-containing receptors, as well as killed the activity at GluN2A- and GluN2B-containing receptors.

TABLE 7

SAR study of 997-95 and 997-99

| 997- | R | 2A IC$_{50}$ 2D IC$_{50}$ | 2B IC$_{50}$ 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|
| 95 | F | 5 | 1 | 30 | 6.4 | 4.8 | 6.2 |
| 99 | H | — | — | NE | NE | 16 | 12 |

Data were from 4-13 oocytes between 1-2 frogs.
NE indicates less than 50% inhibition at 30 μM.

A-Phenyl Ring Modification

To explore the favorable substitution that contributes to the activity of the 997-95 scaffold, the ring on the right side was first optimized. The synthetic pathways were the same as the procedures of forming 997-95, by choosing the appropriate aldehydes to yield the α,β,-unsaturated ketones (Scheme 13).

Scheme 13. Synthesis of compounds with the 997-95 scaffold

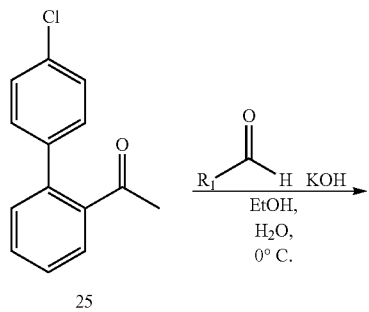

997-series

Compound 997-116 with a 4-fluorophenyl substitution on the right ring showed poor activity and selectivity at the GluN2C- and GluN2D-containing receptors. Replacing 4-chlorophenyl with 4-trifluoromethyloxyphenyl led to compound 997-117, which increased the potency at the GluN2D-containing receptor with an IC$_{50}$ value of 2.87 μM. However, the selectivity at the GluN2D subunit over the GluN2A- and GluN2B-containing receptors was poor as a single-digit fold. Similarly, compound 997-118 with a 2-chlorothiphene performed with an IC$_{50}$ value of 3.74 μM at the GluN2D subunit and showed poor selectivity over other subunits. Compounds 997-119 and 997-122 with a benzo[1,3]dioxole were inactive at all receptors (see Table 8).

TABLE 8

SAR study of compounds with right ring modification

| 997- | R$_1$ | R$_2$ | 2B IC$_{50}$ 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|
| 116 | 4-fluorophenyl | F | 3 | NE | 23.077 | 12.07 | 7.41 |
| 117 | 4-OCF$_3$-phenyl | F | 3 | 17.23 | 8.79 | 3.436 | 2.87 |
| 118 | 5-chlorothiophen-2-yl | F | 3 | 9.01 | 12.02 | 3.69 | 3.74 |

TABLE 8-continued

SAR study of compounds with right ring modification

| 997- | R$_1$ | R$_2$ | 2B IC$_{50}$ 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|
| 119 | benzodioxole | F | — | NE | NE | NE | NE |
| 122 | benzodioxole | H | — | NE | NE | NE | NE |

Data were from 4-13 oocytes between 1-2 frogs.
NE indicates less than 50% inhibition at 30 μM.

B-Phenyl Ring Modification

The top ring was also modified to improve the activity and selectivity. Starting with commercially available 2'-bromo-acetophenone and an appropriate phenylboronic acid, compounds 997-100, and 997-120 to 997-124 were synthesized (Scheme 14) via the same procedures described later.

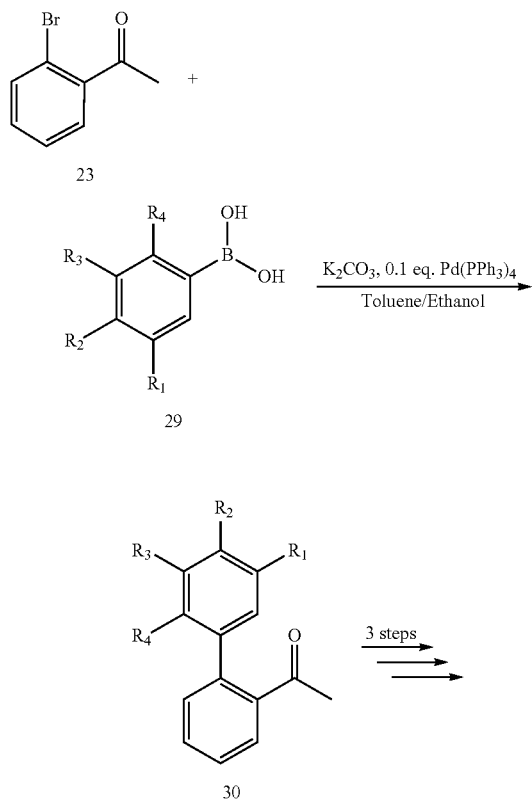

Scheme 14. Synthesis of compounds with the 997-95 scaffold

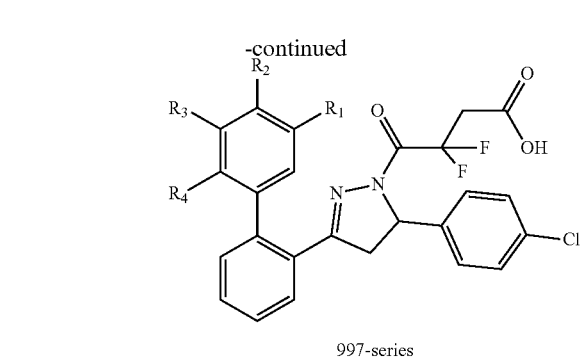

997-series

Compound 997-100 with a meta-fluoro substitution on the phenyl ring lost the activity at all receptors. Both 997-120 with 4-chloro-3-fluoro substitution and 997-123 with 3,5-dichloro substitution increased the potency at the GluN2D-containing receptor with IC$_{50}$ values of 3.359 μM and 4.67 μM, respectively (Table 9). The GluN2D selectivity of 997-120 over other subunits remained poor, while 997-123 slightly improved the selectivity. Compound 997-121 with a 2,4-difluoro substitution decreased the activity by 2-fold in comparison to 997-95. Notably, compound 997-124 with a 4-trifluoromethyl substitution on the top ring performed with an IC$_{50}$ value of 3.57 μM at the GluN2D-containing receptor and improved the selectivity over the GluN2A-containing receptor. Therefore, the 997-95 scaffold preferred a more hydrophobic and electron-withdrawing substitution on the top ring.

TABLE 9

SAR study of compounds with top ring modification

| 997- | R$_1$ | R$_2$ | R$_3$ | R$_4$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|---|
| 100 | H | H | F | H | NE | NE | NE | NE |
| 120 | H | F | Cl | H | 11 | 8.8 | 5.233 | 3.359 |
| 121 | H | F | H | F | NE | NE | 13.55 | 12.25 |

TABLE 9-continued

SAR study of compounds with top ring modification

| 997- | R$_1$ | R$_2$ | R$_3$ | R$_4$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|---|
| 123 | Cl | H | Cl | H | NE | 15.57 | 7.34 | 4.67 |
| 124 | H | CF$_3$ | H | H | NE | 14.75 | 3.63 | 3.57 |

Data were from 4-13 oocytes of 1-2 frogs.
NE indicated less than 50% inhibition at 30 μM.

Chemistry Experimental

All the commercially available chemicals were purchased from Sigma-Aldrich and Alfa Aesar and used without further purification. Reaction progress was monitored using thin layer chromatography (TLC) on pre-coated aluminum plates (silica gel 60 F254, 0.25 mm) and liquid chromatography-mass spectrometry (LCMS, Varian). Flash column chromatography using a Teledyne ISCO Combiflash Companion with Teledyne RediSep disposable normal phase silica columns is used to purify crude compounds. The purity of final compounds was evaluated in two solvents systems (MeOH/water and ACN/water) by HPLC (Varian). Proton, carbon and fluorine NMR spectra were recorded on Mercury 300 (300 MHz), VNMRS 400 (400 MHz), or INOVA 400 (400 MHz) instruments. Proton and carbon NMR spectra utilize the related solvent peak as references, while fluorine NMR spectra employ trifluoroacetic acid (TFA) residual peak as a reference. All chemical shifts and coupling constants were reported in parts per million and Hertz (Hz), respectively. The high-resolution mass spectrometry (IRMS) was evaluated from Emory University Mass Spectrometry Center on either a VG 70-S Nier Johnson or JEOL instrument

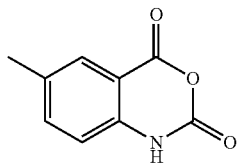

6-methyl-2H-benzo[d][1,3]oxazine-2,4(1H)-dione (1b). Triphosgene (0.34 equiv. WARNING, triphosgene is toxic and should be handled with care, refer to MSDS before handling) in THF (0.23 M) was added in a solution of 2-amino-5-methylbenzoic acid (1.0 equiv.) in THF using syringe pump at a flow rate of 25 ml/h. The mixture was refluxed at 70° C. for around two hours. The mixture was poured onto an ice bath, and the resultant solid was filtered and washed with MeOH to yield the desired products. Yield 75%.

General procedure A for the synthesis of 2-amino-N-methoxybenzamide (2). In a flame dried round-bottomed flask, triethylamine (1.5 equiv.) and NO-dimethylhydroxylamine hydrochloride (1.5 equiv.) in ethanol (2.5 M, 90%) were stirred for 10 minutes. Compound 1 (1.0 equiv.) was then added slowly. The mixture was heated to reflux for approximately two hours. Upon completion, the mixture was poured onto ice/saturated sodium bicarbonate. The ethanol was removed in vacuo, and the mixture was extracted with ethyl acetate. The organic layer was washed 3× with brine, dried over magnesium sulfate, concentrated in vacuo.

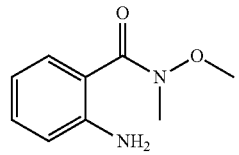

2-amino-N-methoxy-N-methylbenzamide (2a). Compound 2a was prepared via general procedure A using 1a. Purification with flash column chromatography using 20% EtOAc: Hexanes yielded the title compound 80% as a brown oil.

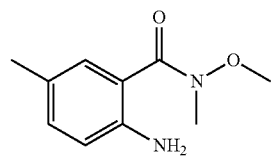

2-amino-N-methoxy-N,5-dimethylbenzamide (2b). Compound 2b was prepared via general procedure A using 1b. Purification with flash column chromatography using 20% EtOAc: Hexanes yielded the title compound 62% as a brown oil.

General procedure B for the synthesis of 2-aminobenzophenone intermediates. In a flame dried round-bottomed flask at −78° C., compound 2 (1 equiv.) and an appropriately substituted bromo-benzene (1 equiv.) in THF (0.17 M) were stirred under nitrogen. n-Butyllithium (2 equiv., 2.5 M in Hexanes) was added at a flow rate of 0.3 ml/min. Upon completion of the addition, 2 ml of 1N HCl per 1 ml of n-butyllithium was added while the temperature was still controlled at −78° C. The mixture was then warmed to room temperature with stirring, and the THF was removed in vacuo. The resultant mixture was extracted with ethyl acetate, washed with brine, dried over magnesium sulfate, and concentrated in vacuo. Purification with flash column chromatography (20% gradient) EtOAc: Hexanes gave the desired product.

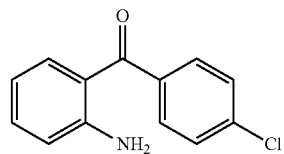

(2-aminophenyl)(4-chlorophenyl)methanone (3a). Compound 3a was prepared via general procedure B using 1-bromo-4-chlorobenzene (8.56 g, 44.7 mmol) and 2a (8.06 g, 44.7 mmol). Purification by flash chromatography using 20% isocratic EtOAc: Hexanes yielded the title compound as a yellow solid. Yield 6.58 g, 63.5%.

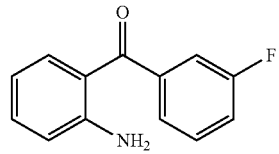 [SMILES: Nc1ccccc1C(=O)c1cccc(F)c1]

(2-aminophenyl)(3-fluorophenyl)methanone (3b). Compound 3b was prepared via general procedure B using 1-bromo-3-fluorobenzene (4.30 g, 24.57 mmol) and 2a (4.43 g, 24.57 mmol). Purification by flash chromatography using 20% isocratic EtOAc: Hexanes yielded the title compound as a yellow solid. Yield 2.7 g, 51%.

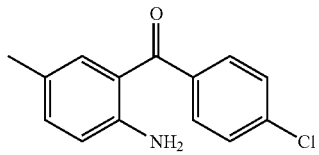 [SMILES: Cc1ccc(N)c(C(=O)c2ccc(Cl)cc2)c1]

(2-amino-5-methylphenyl)(4-chlorophenyl)methanone (3c). Compound 3c was prepared via general procedure B using 1-bromo-4-chlorobenzene and 2b. Purification by flash chromatography using 20% isocratic EtOAc: Hexanes yielded the title compound as a yellow solid. Yield 59%.

General procedure C for the synthesis of quinolin-2(1H)-one intermediates. An appropriate 2-aminobenzophenone (1.0 equiv.) and the ethyl acetoacetate (1.5 equiv.) were dissolved in DMF (1.4 M) in a microwaveable vessel and microwaved at 180° C. for 8 minutes in the presence of 4 Angstrom molecular sieves. The reaction was then vented of gas and re-submitted to the microwave irradiation at 180° C. for another 8 minutes. The resultant mixture was transferred to a round-bottomed flask, and the solvent DMF was removed in vacuo. Ethyl acetate was added to the flask, and the solid was filtered. The filtrate was then concentrated in vacuo, and ethyl acetate was added again, followed by filtration of the solid that retained. The solids were collected and determined to be the desired product. In a large scale, an appropriate 2-aminobenzophenone (1.0 equiv.) and the ethyl acetoacetate (1.5 equiv.) were dissolved in DMF (0.4 M) in the presence of 4 Angstrom molecular sieves and refluxed overnight. The molecular sieves were filtered out, and the filtrate was concentrated in vacuo. Ethyl acetate was added, and then the mixture was filtered, giving the product as solid. As the project moves, this procedure can be simplified. The resultant solids from filtration were directly used in the following step without further purification.

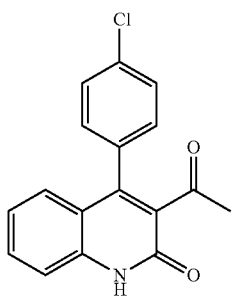 [SMILES: CC(=O)c1c(-c2ccc(Cl)cc2)c2ccccc2[nH]c1=O]

3-acetyl-4-(4-chlorophenyl)quinolin-2(1H)-one (4a). Compound 4a was prepared via procedure C with 3a. Yield 10.21 g, 122%.

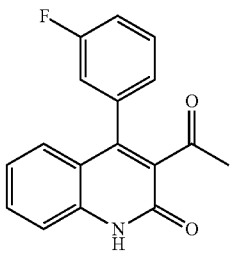 [SMILES: CC(=O)c1c(-c2cccc(F)c2)c2ccccc2[nH]c1=O]

3-acetyl-4-(3-fluorophenyl)quinolin-2(1H)-one (4b). Compound 4b was prepared via procedure C with 3b (1.5 g, 6.97 mmol). Yield 0.92 g, 46.9%.

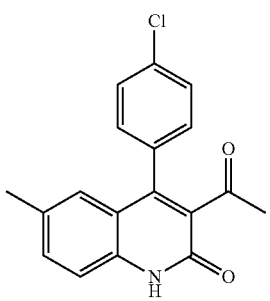 [SMILES: CC(=O)c1c(-c2ccc(Cl)cc2)c2cc(C)ccc2[nH]c1=O]

3-acetyl-4-(4-chlorophenyl)-6-methylquinolin-2(1H)-one (4c). Compound 4c was prepared via procedure C with 3c.

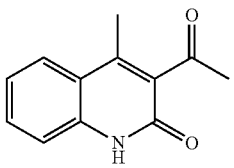

3-acetyl-4-methylquinolin-2(1H)-one (4d). The 2-acetylaniline (1 equiv.) and ethyl acetoacetate (1 equiv.) were mixed with cerium (III) chloride heptahydrate (0.2 equiv.). The mixture was introduced into a microwaved vessel and was microwaved at 160° C. for 6 minutes. After cooled to room temperature, water (5-10 ml) was then added to the reaction mixture, and the mixture was stirred for another 5 min. The solid was collected by Buchner filtration, washed with water and ethyl acetate/hexanes (1:4), and then air-dried to give the product as white powder.

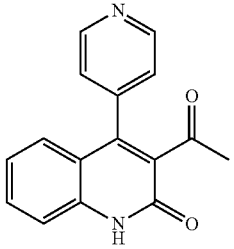 [SMILES: CC(=O)c1c(-c2ccncc2)c2ccccc2[nH]c1=O]

3-acetyl-4-(pyridin-4-yl)quinolin-2(1H)-one (4e). Compound 4e was prepared via procedure C with 3e.

General procedure D for the synthesis of quinolin-2(1H)-one acroyl intermediates. In a round-bottomed flask, the quinolin-2(1H)-one (1 equiv.) and potassium hydroxide (25 equiv.) were stirred in EtOH/H₂O (3:2, 0.05 M) at 0° C. for 45 minutes. 4-chlorobenzaldehyde or appropriate aldehyde (1 equiv.) was then added to the mixture. The reaction was stirred overnight. Upon completion, the reaction was quenched by slow addition of 2N hydrogen chloride (equal molar to KOH) and the resultant solid was filtered. The solid was then extracted from DCM and washed with brine, dried with magnesium sulfate and concentrated in vacuo. As the project moves, this procedure can be simplified. The resultant solids from filtration were directly used in the following step without further purification.

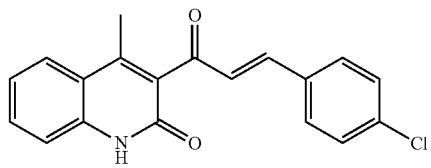

(E)-3-(3-(4-chlorophenyl)acryloyl)-4-methylquinolin-2(1H)-one (5d). Compound 5d was prepared via the general procedure D using 4d.

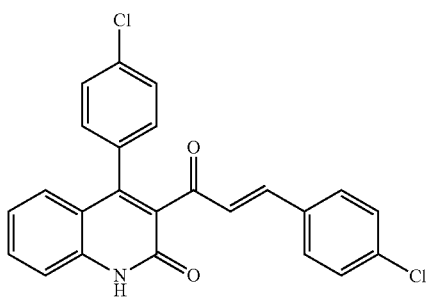 [SMILES: O=C(/C=C/c1ccc(Cl)cc1)c1c(-c2ccc(Cl)cc2)c2ccccc2[nH]c1=O]

(E)-4-(4-chlorophenyl)-3-[3-(4-chlorophenyl)acryloyl]quinolin-2(1H)-one (5a). Compound 5a was prepared via the general procedure D using 4a (2.5 g, 8.4 mmol) as a yellowish solid. Yield 1.96 g, 55.5%.

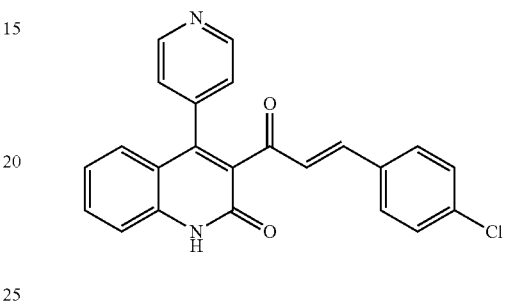

(E)-3-(3-(4-chlorophenyl)acryloyl)-4-(pyridin-4-yl)quinolin-2(1H)-one (5e). Compound 5e was prepared via the general procedure D using 4e.

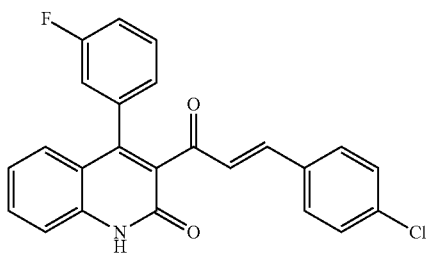 [SMILES: O=C(/C=C/c1ccc(Cl)cc1)c1c(-c2cccc(F)c2)c2ccccc2[nH]c1=O]

(E)-3-[3-(4-chlorophenyl)acryloyl]-4-(3-fluorophenyl)quinolin-2(1H)-one (5b/997-71). Compound 5b was prepared via the general procedure D using 4b (1.28 g, 4.55 mmol) as a yellowish solid. Yield 1.3 g, 70.7%.

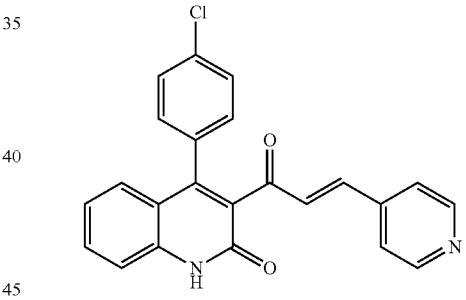

(E)-4-(4-chlorophenyl)-3-[3-(pyridin-4-yl)acryloyl]quinolin-2(1H)-one (11a). Compound 11a was prepared via the general procedure D using 4a and isonicotinaldehyde.

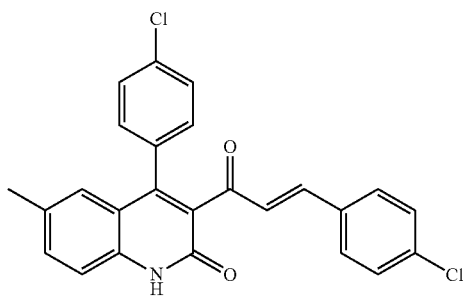 [SMILES: Cc1ccc2[nH]c(=O)c(C(=O)/C=C/c3ccc(Cl)cc3)c(-c3ccc(Cl)cc3)c2c1]

(E)-4-(4-chlorophenyl)-3-[3-(4-chlorophenyl)acryloyl]-6-methylquinolin-2(1H)-one (5c). Compound 5c was prepared via the general procedure D using 4c.

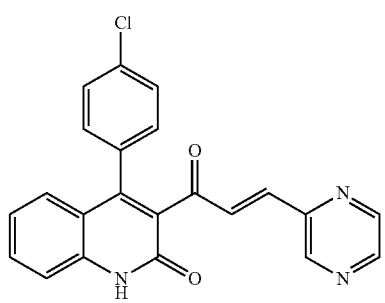 [SMILES: O=C(/C=C/c1cnccn1)c1c(-c2ccc(Cl)cc2)c2ccccc2[nH]c1=O]

(E)-4-(4-chlorophenyl)-3-[3-(pyrazin-2-yl)acryloyl]quinolin-2(1H)-one (11b). Compound 11b was prepared via the general procedure D using 4a and pyrazine-2-carbaldehyde.

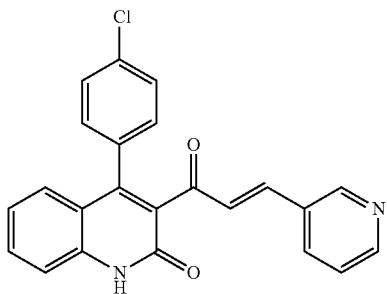 [SMILES: O=C(/C=C/c1cccnc1)c1c(-c2ccc(Cl)cc2)c2ccccc2[nH]c1=O]

(E)-4-(4-chlorophenyl)-3-[3-(pyridin-3-yl)acryloyl]quinolin-2(1H)-one (11c). Compound 11c was prepared via the general procedure D using 4a and nicotinaldehyde.

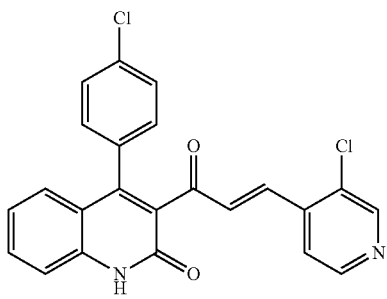 [SMILES: O=C(/C=C/c1ccncc1Cl)c1c(-c2ccc(Cl)cc2)c2ccccc2[nH]c1=O]

(E)-4-(4-chlorophenyl)-3-[3-(3-chloropyridin-4-yl)acryloyl]quinolin-2(1H)-one (11d). Compound 11d was prepared via the general procedure D using 4a and 3-choroisonicotinaldehyde.

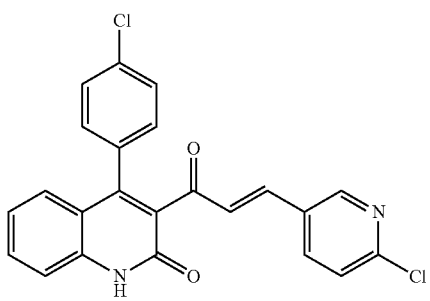 [SMILES: O=C(/C=C/c1ccc(Cl)nc1)c1c(-c2ccc(Cl)cc2)c2ccccc2[nH]c1=O]

(E)-4-(4-chlorophenyl)-3-[3-(6-chloropyridin-3-yl)acryloyl]quinolin-2(1H)-one (11e). Compound 11e was prepared via the general procedure D using 4a and 6-chloronicotinaldehyde. This compound was directly used in the following step without further purification.

General procedure E for the synthesis of pyrazol-3-yl-quinolin-2(1H)-one intermediates. In an appropriate microwaveable vessel, the quinolin-2(1H)-one acroyl intermediate (1 equiv.) was dissolved in EtOH (0.25 M, 190 proof or 200 proof) and hydrazine monohydrate (1.5 equiv.) was added. The mixture was microwaved for 20 minutes at 110° C. Solid that present in the reaction vial was filtered to yield the desired product without further purification.

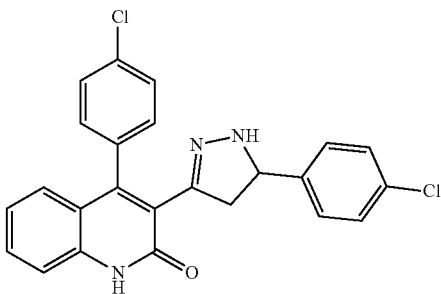 [SMILES: O=c1[nH]c2ccccc2c(-c2ccc(Cl)cc2)c1C1=NNC(c2ccc(Cl)cc2)C1]

4-(4-chlorophenyl)-3-[5-(4-chlorophenyl)-4,5-dihydro-1H-pyrazol-3-yl]quinolin-2(1H)-one (5a/997-70). Compound 997-70 was prepared via general procedure E using 5a (1.13 g, 2.69 mmol) as a yellowish solid. Yield 0.95 g, 81%.

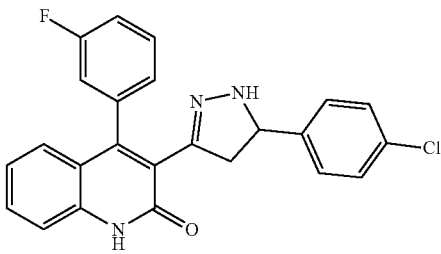 [SMILES: O=c1[nH]c2ccccc2c(-c2cccc(F)c2)c1C1=NNC(c2ccc(Cl)cc2)C1]

3-[5-(4-chlorophenyl)-4,5-dihydro-1H-pyrazol-3-yl]-4-(3-fluorophenyl)quinolin-2(1H)-one (6b). Compound 6b was prepared via general procedure E using 5b (1.15 g, 2.85 mmol) as a yellowish solid. Yield 0.80 g, 67.2%.

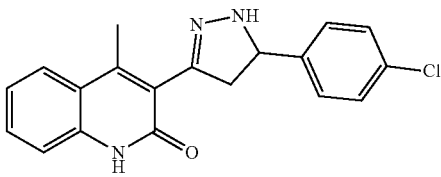 [SMILES: Cc1c(C2=NNC(c3ccc(Cl)cc3)C2)c(=O)[nH]c2ccccc12]

3-(5-(4-chlorophenyl)-4,5-dihydro-1H-pyrazol-3-yl)-4-methylquinolin-2(1H)-one (5d/997-77). Compound 997-77 was prepared via general procedure E using 5d.

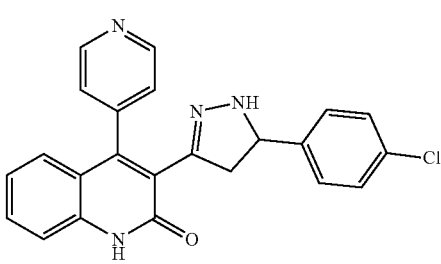 [SMILES: O=c1[nH]c2ccccc2c(-c2ccncc2)c1C1=NNC(c2ccc(Cl)cc2)C1]

3-(5-(4-chlorophenyl)-4,5-dihydro-1H-pyrazol-3-yl)-4-(pyridin-4-yl)quinolin-2(1H)-one (5e/997-81). Compound 997-81 was prepared via general procedure E using 5e.

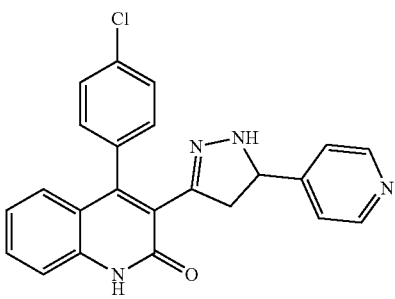 [SMILES: O=c1[nH]c2ccccc2c(-c2ccc(Cl)cc2)c1C1=NNC(c2ccncc2)C1]

4-(4-chlorophenyl)-3-[5-(pyridin-4-yl)-4,5-dihydro-1H-pyrazol-3-yl]quinolin-2(1H)-one (997-78). Compound 997-78 was prepared via general procedure E using 11a.

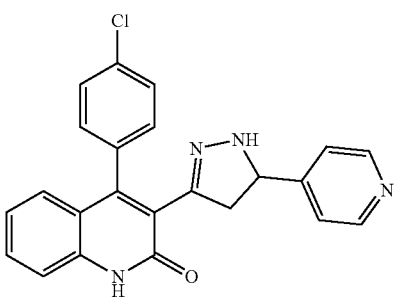 [SMILES: O=c1[nH]c2ccccc2c(-c2ccc(Cl)cc2)c1C1=NNC(c2ccncc2)C1]

4-(4-chlorophenyl)-3-[5-(pyrazin-2-yl)-4,5-dihydro-1H-pyrazol-3-yl]quinolin-2(1H)-one (12b). Compound 12b was prepared via general procedure E using 11b.

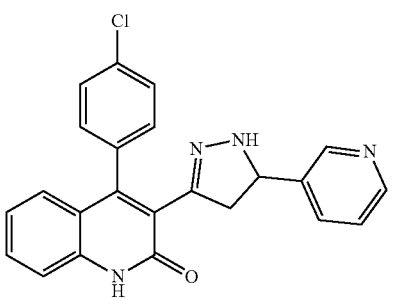 [SMILES: O=c1[nH]c2ccccc2c(-c2ccc(Cl)cc2)c1C1=NNC(c2cccnc2)C1]

4-(4-chlorophenyl)-3-[5-(pyridin-3-yl)-4,5-dihydro-1H-pyrazol-3-yl]quinolin-2(1H)-one (12c). Compound 12c was prepared via general procedure E using 11c.

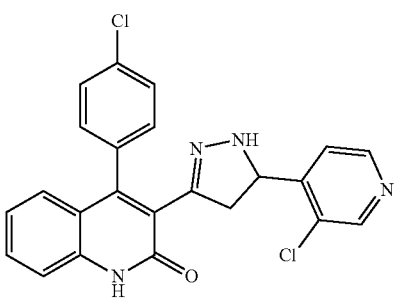 [SMILES: O=c1[nH]c2ccccc2c(-c2ccc(Cl)cc2)c1C1=NNC(c2ccncc2Cl)C1]

4-(4-chlorophenyl)-3-[5-(3-chloropyridin-4-yl)-4,5-dihydro-1H-pyrazol-3-1]quinolin-2(1H)-one (12d). Compound 12d was prepared via general procedure E using 11d.

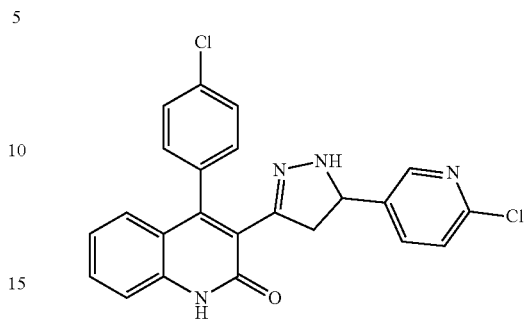

4-(4-chlorophenyl)-3-[5-(6-chloropyridin-3-yl)-4,5-dihydro-1H-pyrazol-3-1]quinolin-2(1H)-one (12e). Compound 12e was prepared via general procedure E using 11e.

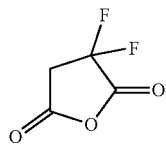

3,3-difluorodihydrofuran-2,5-dione (8). To a solution of 2,2-difluorosuccinic acid (1 equiv.) in i-PrOAc (0.5 M) was added trifluoroacetic anhydride (1.2 equiv.) in one portion at ambient temperature. The reaction solution was stirred at 50° C. for approximately 1.5 hours. The mixture was distilled at 140° C. (the vapor temperature was around 89-90° C.). The remaining liquid or solid was determined to be desired product.

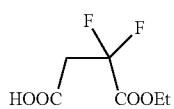

4-ethoxy-3,3-difluoro-4-oxobutanoic acid (9). Dry absolute ethanol (1.3 M) was added dropwise to 8 at 0° C. The mixture was then warmed to room temperature and was stirred for 18 hours. Then the mixture was evaporated in vacuo and extracted with DCM/0.1 N HCl, dried with magnesium sulfate and concentrated in vacuo.

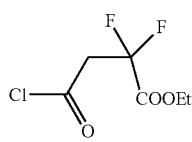

Ethyl 4-chloro-2,2-difluoro-4-oxobutanoate (10). In a round-bottomed flask, 9 (1 equiv.) was dissolved in DCM (0.3 M). Then oxalyl dichloride (2.5 equiv.) was added dropwise, followed by on drop of DMF. The reaction was stirred for approximately 40 minutes. The solvent and excess oxalyl dichloride was removed under vacuum and the product was obtained by Kugelrohr distillation at 98° C. with full vacuum. Used immediately.

General procedure F for the synthesis of acylated quinolone pyrazoline products. In an appropriate microwaveable vessel, the pyrazol-3-yl-quinolin-2(1H)-one (1 equiv.) and 10 (1 equiv.) were dissolved in anhydrous THF (0.151 M) with 4 Angstrom molecular sieves. The reaction was microwaved at 165° C. for 20 minutes. The THF was removed under vacuum and the mixture was extracted with DCM, washed 3× with acidified (1N HCl) brine, dried over magnesium sulfate, filtered, concentrated in vacuo, and subjected to flash column chromatography using a 0-10% MeOH/DCM gradient.

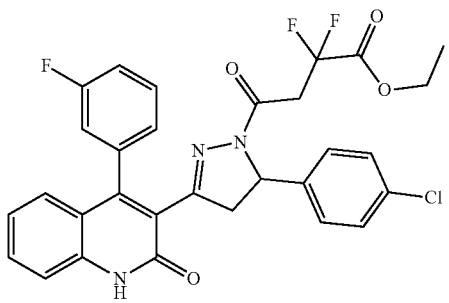 [SMILES: CCOC(=O)C(F)(F)CC(=O)N1N=C(c2c(-c3cccc(F)c3)c3ccccc3[nH]c2=O)CC1c1ccc(Cl)cc1]

Ethyl 4-{5-(4-chlorophenyl)-3-[4-(3-fluorophenyl)-2-oxo-1,2-dihydroquinolin-3-yl]-4,5-dihydro-1H-pyrazol-1-yl}-2,2-difluoro-4-oxobutanoate (997-65). Compound 997-65 was prepared via general procedure F using 6b (720 mg, 1.723 mmol). Yield 89 mg, 8.88%. $^1$H NMR (400 MHz, CDCl$_3$) δ 13.28 (s, 1H), 7.62-7.51 (m, 2H), 7.41 (d, J=8.1 Hz, 1H), 7.30-7.04 (m, 9H), 5.46 (dd, J=11.6, 3.4 Hz, 1H), 4.26 (qd, J=7.2, 2.5 Hz, 2H), 3.86-3.79 (m, 1H), 3.45-3.24 (m, 3H), 1.24 (td, J=7.2, 1.5 Hz, 3H).

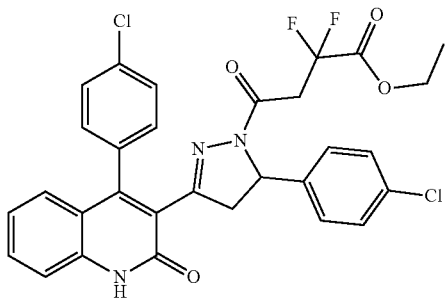 [SMILES: CCOC(=O)C(F)(F)CC(=O)N1N=C(c2c(-c3ccc(Cl)cc3)c3ccccc3[nH]c2=O)CC1c1ccc(Cl)cc1]

Ethyl 4-{5-(4-chlorophenyl)-3-[4-(4-chlorophenyl)-2-oxo-1,2-dihydroquinolin-3-yl]-4,5-dihydro-1H-pyrazol-1-yl}-2,2-difluoro-4-oxobutanoate (997-66). Compound 997-66 was prepared via general procedure F using 6a (850 mg, 1.957 mmol). Yield 118 mg, 10%. $^1$H NMR (400 MHz, CDCl$_3$) δ 13.19 (s, 1H), 7.62-7.58 (m, 1H), 7.54 (dd, J=8.3, 2.1 Hz, 1H), 7.50 (dd, J=8.0, 2.2 Hz, 1H), 7.41 (d, J=8.3 Hz, 1H), 7.32 (dd, J=8.1, 2.1 Hz, 1H), 7.30-7.22 (m, 5H), 7.01 (dt, J=8.3, 1.9 Hz, 2H), 5.44 (dd, J=11.6, 4 Hz, 1H), 4.27 (q, J=7.2 Hz, 2H), 3.74 (dd, J=18.4, 11.8 Hz, 1H), 3.47-3.30 (m, 2H), 3.18 (dd, J=18.3, 4 Hz, 1H), 1.25 (t, J=7.2 Hz, 3H).

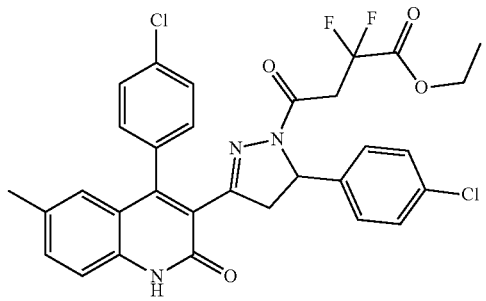 [SMILES: CCOC(=O)C(F)(F)CC(=O)N1N=C(c2c(-c3ccc(Cl)cc3)c3cc(C)ccc3[nH]c2=O)CC1c1ccc(Cl)cc1]

Ethyl 4-{5-(4-chlorophenyl)-3-[4-(4-chlorophenyl)-6-methyl-2-oxo-1,2-dihydroquinolin-3-yl]-4,5-dihydro-1H-pyrazol-1-yl}-2,2-difluoro-4-oxobutanoate (7c).

Compound 7c was prepared via general procedure F using 6c. The product was obtained after flash chromatography and using 1.3% MeOH/DCM. $^1$H NMR (400 MHz, DMSO-d6) δ 12.24 (s, 1H), 7.59 (ddd, J=14.4, 8.2, 2.4 Hz, 2H), 7.44-7.40 (m, 2H), 7.33 (t, J=8.0 Hz, 2H), 7.31 (dd, J=8.0, 2.5 Hz, 2H), 6.87 (d, J=8.6 Hz, 2H), 6.82 (s, 1H), 5.37 (dd, J=11.9, 4.1 Hz, 1H), 4.20-4.11 (m, 2H), 3.80 (dd, J=18.6, 12.0 Hz, 1H), 3.43-3.15 (m, 2H), 2.94 (dd, J=18.6, 4.5 Hz, 1H), 2.23 (s, 3H), 1.12 (t, J=7.2 Hz, 3H).

General procedure G for the synthesis of difluoro-substituted hydroxybutanoyl quinolone pyrazoline products. A solution of acylated quinolone pyrazoline product (1 equiv.) in absolute ethanol was added dropwise to stirred solution of sodium borohydride (0.5 equiv.) in absolute ethanol. (Overall 0.015 M EtOH). The mixture was cooled in an ice/salt bath and the temperature was kept at 16° C. by controlling the rate of addition. After the addition was completed, the mixture was stirred at room temperature for another 15 hours. The ethanol was evaporated and the residue was extracted with DCM and 4 N H$_2$SO$_4$. The aqueous phase was extracted twice with DCM. Then the organic phases were combined, washed twice with 2 N H$_2$SO$_4$, dried over magnesium sulfate, and evaporated in vacuo. Purification with flash column chromatography using 0-80% EtOAc:Hexanes.

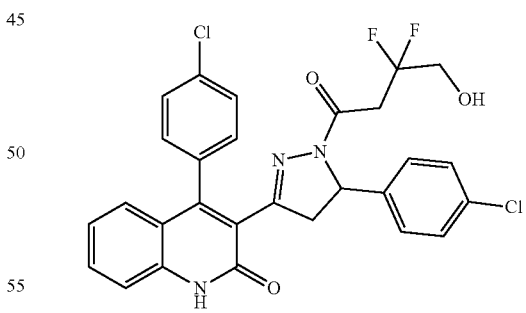

4-(4-chlorophenyl)-3-[5-(4-chlorophenyl)-1-(3,3-difluoro-4-hydroxybutanoyl)-4,5-dihydro-1H-pyrazol-3-yl]quinolin-2(1H)-one (997-67). Compound 997-67 was prepared via general procedure G using 997-66 (108 mg, 0.180 mmol). Yield 20 mg, 19.92%. $^1$H NMR (400 MHz, CDCl$_3$) δ 12.69 (s, 1H), 7.59 (quintet, J=4.2 Hz, 1H), 7.52 (dd, J=8.1, 2.1 Hz, 1H), 7.48 (dd, J=8.1, 2.1 Hz, 1H), 7.39 (d, J=8.3 Hz, 1H), 7.33 (dd, J=8.1, 2.2 Hz, 1H), 7.28 (d, J=8.3 Hz, 2H), 7.23 (d, J=2.2 Hz, 1H), 7.22 (d, J=4.5 Hz, 2H), 6.95 (d, J=8.6 Hz, 2H), 5.44 (dd, J=11.8, 4.1 Hz, 1H), 3.81

(sextet, J=12 Hz, 2H), 3.71 (dd, J=18.4, 11.8 Hz, 1H), 3.41-3.24 (m, 2H), 3.02 (dd, J=18.4, 4.1 Hz, 1H), 2.72 (broad s, 1H).

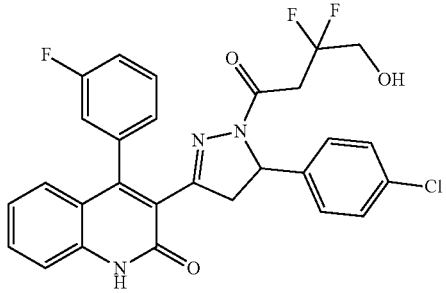 [SMILES: O=C(CC(F)(F)CO)N1N=C(c2c(-c3cccc(F)c3)c3ccccc3[nH]c2=O)CC1c1ccc(Cl)cc1]

3-[5-(4-chlorophenyl)-1-(3,3-difluoro-4-hydroxybutanoyl)-4,5-dihydro-1H-pyrazol-3-yl]-4-(3-fluorophenyl)quinolin-2(1H)-one (997-68). Compound 997-68 was prepared via general procedure G using 997-65 (200 mg, 0.344 mmol). Yield 35 mg, 18.86%. ¹H NMR (400 MHz, CDCl₃) δ 12.73 (d, J=16 Hz, 1H), 7.60-7.46 (m, 2H), 7.38 (dt, J=8.3, 0.8 Hz, 1H), 7.28-7.17 (m, 6H), 7.10 (td, J=8.4, 1.5 Hz, 1H), 7.03-6.97 (m, 2H), 5.45 (dd, J=11.8, 4.1 Hz, 1H), 3.86-3.69 (m, 3H), 3.33-3.20 (m, 2H), 3.09 (dt, J=18.4, 4.1 Hz, 1H), 2.72 (s, 1H).

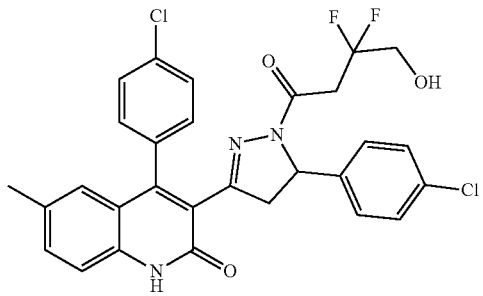 [SMILES: Cc1ccc2[nH]c(=O)c(C3=NN(C(=O)CC(F)(F)CO)C(c4ccc(Cl)cc4)C3)c(-c3ccc(Cl)cc3)c2c1]

4-(4-chlorophenyl)-3-[5-(4-chlorophenyl)-1-(3,3-difluoro-4-hydroxybutanoyl)-4,5-dihydro-1H-pyrazol-3-yl]-6-methylquinolin-2(1H)-one (997-91). Compound 997-91 was prepared via general procedure G using 7c. The product was obtained after flash chromatography and came out at 60-65% EtOAc: Hexanes. ¹H NMR (400 MHz, DMSO-d6) δ 12.23 (s, 1H), 7.59 (dd, J=8.2, 2.3 Hz, 1H), 7.53 (d, J=8.2 Hz, 1H), 7.43-7.27 (m, 6H), 6.82 (d, J=8.2 Hz, 3H), 5.48 (s, 1H), 5.38 (dd, J=12.0, 4.1 Hz, 1H), 3.76 (dd, J=18.4, 11.7 Hz, 1H), 3.62 (td, J=14.5, 5.9 Hz, 2H), 3.16-2.97 (m, 2H), 2.78 (dd, J=18.5, 4.1 Hz, 1H), 2.22 (s, 3H).

General procedure H for the synthesis of difluoro-substituted hydroxybutanoic acid quinolone pyrazoline products. Compound 8 (1 equiv.) was added in a solution of 6 (1 equiv.) in THF (0.045 molar) at room temperature. After around 24 hours, the crude was concentrated in vacuo, washed with ethyl acetate and 1 N HCl. The organic layer was dried over Mg₂SO₄, filtered and evaporated in vacuo. Finally, the crude compound was purified by flash chromatography using a 0-10% MeOH/DCM gradient to afford product.

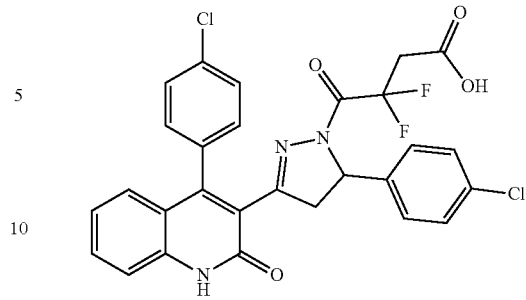

4-(5-(4-chlorophenyl)-3-(4-(4-chlorophenyl)-2-oxo-1,2-dihydroquinolin-3-yl)-4,5-dihydro-1H-pyrazol-1-yl)-3,3-difluoro-4-oxobutanoic acid (997-74). Compound 997-74 was prepared via general procedure H using 6a. ¹H NMR (400 MHz, CDCl₃) δ 12.15 (s, 1H), 7.56 (p, J=4.0 Hz, 1H), 7.50 (d, J=7.9 Hz, 1H), 7.45 (d, J=8.1 Hz, 1H), 7.33 (d, J=8.3 Hz, 1H), 7.28-7.26 (m, 2H), 7.20 (d, J=3.8 Hz, 2H), 7.17 (d, J=7.3 Hz, 2H), 7.15 (d, J=8.3 Hz, 1H), 6.88 (d, J=7.5 Hz, 2H), 5.46 (dd, J=11.5, 4.1 Hz, 1H), 3.68 (dd, J=18.2, 12.1 Hz, 1H), 3.50-3.36 (m, 2H), 2.76 (dd, J=18.3, 4.2 Hz, 1H).

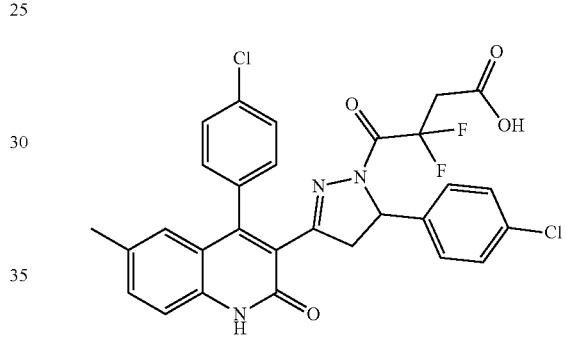

4-(5-(4-chlorophenyl)-3-(4-(4-chlorophenyl)-6-methyl-2-oxo-1,2-dihydroquinolin-3-yl)-4,5-dihydro-1H-pyrazol-1-yl)-3,3-difluoro-4-oxobutanoic acid (997-90). Compound 997-90 was prepared via general procedure H using 6c. ¹H NMR (400 MHz, DMSO-d6) δ 12.92 (s, 1H), 12.27 (s, 1H), 7.54 (dd, J=8.2, 1.9 Hz, 1H), 7.50 (dd, J=8.2, 2.3 Hz, 1H), 7.42 (td, J=7.8, 2.0 Hz, 2H), 7.34 (d, J=8.6 Hz, 1H), 7.30 (d, J=8.2 Hz, 2H), 7.25 (dd, J=8.0, 2.1 Hz, 1H), 6.85 (d, J=8.6 Hz, 2H), 6.79 (s, 1H), 5.50 (dd, J=11.8, 4.3 Hz, 1H), 3.82 (dd, J=18.8, 11.7 Hz, 1H), 3.32-3.20 (m, 2H), 2.71 (dd, J=18.7, 4.7 Hz, 1H), 2.22 (s, 3H).

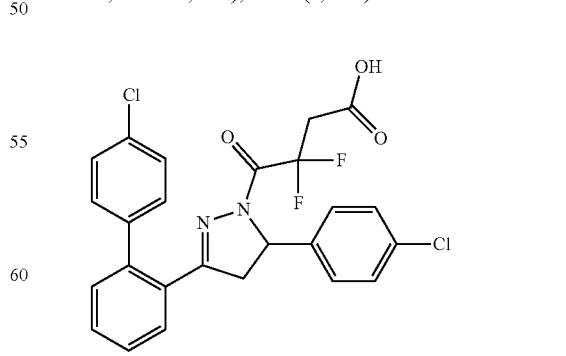

4-(3-(4'-chloro-[1,1'-biphenyl]-2-yl)-5-(4-chlorophenyl)-4,5-dihydro-1H-pyrazol-1-yl)-3,3-difluoro-4-oxobutanoic acid (997-95). Compound 997-95 was prepared via general procedure H. ¹H NMR (400 MHz, DMSO-d₆) δ 12.95 (s, 1H), 7.69 (dd, J=7.5, 1.6 Hz, 1H), 7.60-7.49 (m, 2H), 7.42-7.32 (m, 4H), 7.31-7.26 (m, 2H), 7.18-7.12 (m, 2H), 5.53 (dd, J=11.6, 4.4 Hz, 1H), 3.63 (dd, J=18.4, 11.7 Hz, 1H), 3.22-2.99 (m, 2H), 2.61 (dd, J=18.4, 4.5 Hz, 1H).

yl)-3,3-difluoro-4-oxobutanoic acid (997-102). Compound 997-102 was prepared via general procedure H. ¹H NMR (400 MHz, DMSO-d₆) δ 12.94 (s, 1H), 12.42 (s, 1H), 7.56-7.42 (m, 3H), 7.31 (tt, J=5.6, 2.8 Hz, 5H), 6.92 (dd, J=8.6, 2.8 Hz, 2H), 6.70 (dt, J=9.7, 2.9 Hz, 1H), 5.51 (dt, J=12.3, 3.8 Hz, 1H), 3.86 (ddd, J=18.8, 11.9, 2.7 Hz, 1H), 3.38-3.08 (m, 2H), 2.80 (dt, J=18.7, 3.8 Hz, 1H).

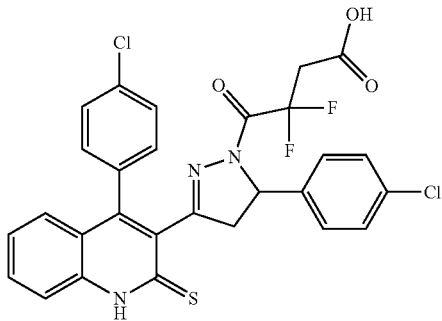 [SMILES: O=C(O)CC(F)(F)C(=O)N1N=C(c2c(-c3ccc(Cl)cc3)c3ccccc3[nH]c2=S)CC1c1ccc(Cl)cc1]

4-(5-(4-chlorophenyl)-3-(4-(4-chlorophenyl)-2-thioxo-1,2-dihydroquinolin-3-yl)-4,5-dihydro-1H-pyrazol-1-yl)-3,3-difluoro-4-oxobutanoic acid (997-98). Compound 997-98 was prepared via general procedure H. ¹H NMR (400 MHz, DMSO-d₆) δ 14.17 (s, 1H), 12.94 (s, 1H), 7.79-7.67 (m, 3H), 7.59 (dd, J=8.2, 2.3 Hz, 1H), 7.44 (dt, J=8.2, 1.9 Hz, 2H), 7.35-7.24 (m, 4H), 7.09-7.01 (m, 1H), 5.49 (dd, J=12.0, 5.1 Hz, 1H), 3.46 (q, J=16.8 Hz, 1H), 3.37-3.19 (m, 2H), 2.67 (s, 1H).

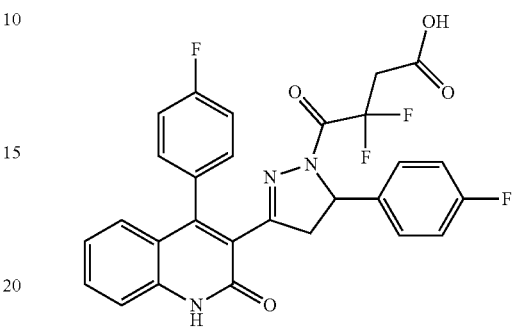

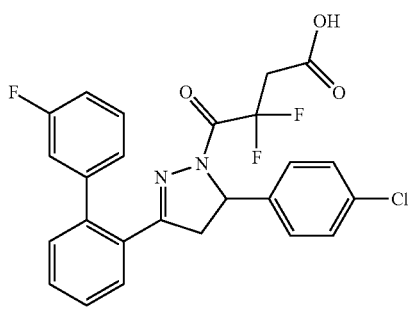 [SMILES: O=C(O)CC(F)(F)C(=O)N1N=C(c2ccccc2-c2cccc(F)c2)CC1c1ccc(Cl)cc1]

4-(5-(4-chlorophenyl)-3-(3'-fluoro-[1,1'-biphenyl]-2-yl)-4,5-dihydro-1H-pyrazol-1-yl)-3,3-difluoro-4-oxobutanoic acid (997-100). Compound 997-100 was prepared via general procedure H. HRMS (m/z): [M+H]⁺ calculated for C₂₅H₁₉O₃N₂ClF₃, 487.10308; found, 487.10335.

3,3-difluoro-4-(5-(4-fluorophenyl)-3-(4-(4-fluorophenyl)-2-oxo-1,2-dihydroquinolin-3-yl)-4,5-dihydro-1H-pyrazol-1-yl)-4-oxobutanoic acid (997-103). Compound 997-103 was prepared via general procedure H. ¹H NMR (400 MHz, DMSO-d₆) δ 12.31 (s, 1H), 7.59 (tt, J=7.0, 1.5 Hz, 1H), 7.48-7.39 (m, 2H), 7.34-7.25 (m, 3H), 7.19-7.11 (m, 1H), 7.10-7.00 (m, 3H), 6.95 (dt, J=7.7, 3.7 Hz, 2H), 5.50 (dd, J=11.9, 4.6 Hz, 1H), 3.90-3.71 (m, 1H), 3.44-3.30 (m, 2H), 2.79 (dt, J=18.6, 2.7 Hz, 1H).

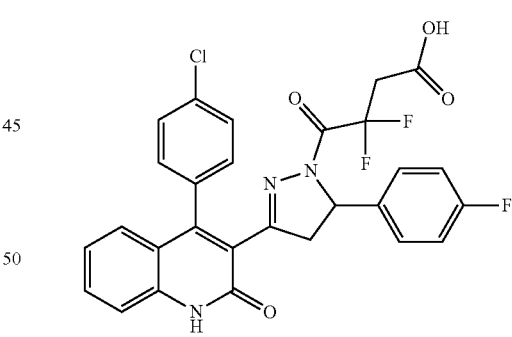

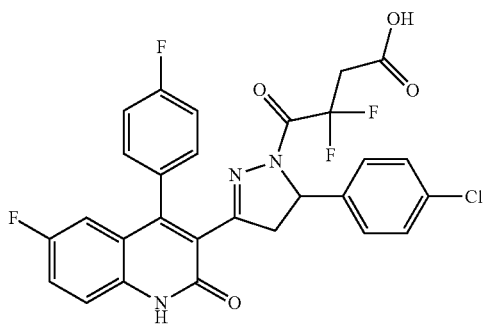 [SMILES: O=C(O)CC(F)(F)C(=O)N1N=C(c2c(-c3ccc(F)cc3)c3cc(F)ccc3[nH]c2=O)CC1c1ccc(Cl)cc1]

4-(5-(4-chlorophenyl)-3-(6-fluoro-4-(4-fluorophenyl)-2-oxo-1,2-dihydroquinolin-3-yl)-4,5-dihydro-1H-pyrazol-1-

4-(3-(4-(4-chlorophenyl)-2-oxo-1,2-dihydroquinolin-3-yl)-5-(4-fluorophenyl)-4,5-dihydro-1H-pyrazol-1-yl)-3,3-difluoro-4-oxobutanoic acid (997-104). Compound 997-104 was prepared via general procedure H. ¹H NMR (400 MHz, DMSO-d₆) δ 7.62-7.48 (m, 3H), 7.46-7.40 (m, 2H), 7.27 (dt, J=8.1, 1.9 Hz, 1H), 7.15 (dd, J=8.4, 6.9 Hz, 1H), 7.10-6.99 (m, 3H), 6.89 (ddd, J=8.9, 5.4, 1.8 Hz, 2H), 5.50 (dd, J=11.9, 4.6 Hz, 1H), 3.98-3.72 (m, 2H), 3.41-3.28 (m, 1H), 2.81-2.66 (m, 1H).

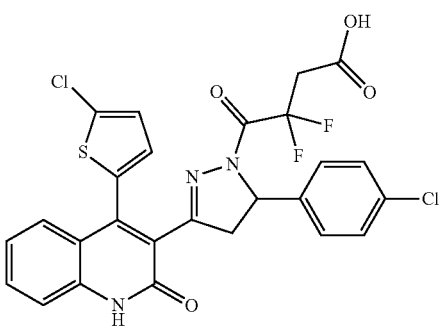 [SMILES: O=C(O)CC(F)(F)C(=O)N1N=C(c2c(-c3ccc(Cl)s3)c3ccccc3[nH]c2=O)CC1c1ccc(Cl)cc1]

4-(5-(4-chlorophenyl)-3-(4-(5-chlorothiophen-2-yl)-2-oxo-1,2-dihydroquinolin-3-yl)-4,5-dihydro-1H-pyrazol-1-yl)-3,3-difluoro-4-oxobutanoic acid (997-109). Compound 997-109 was prepared via general procedure H. $^1$H NMR (400 MHz, DMSO-d$_6$) δ 12.97 (s, 1H), 12.39 (s, 1H), 7.68-7.55 (m, 1H), 7.46-7.31 (m, 4H), 7.27-7.16 (m, 2H), 7.14-7.00 (m, 3H), 5.60 (dd, J=11.9, 4.7 Hz, 1H), 3.93-3.80 (m, 1H), 3.55-3.17 (m, 2H), 2.84 (dd, J=18.8, 4.9 Hz, 1H).

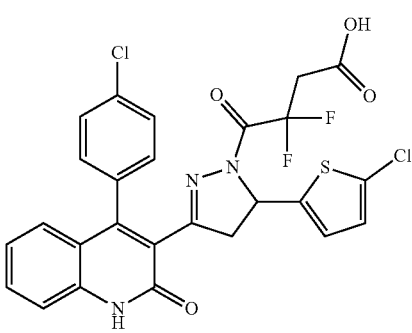 [SMILES: O=C(O)CC(F)(F)C(=O)N1N=C(c2c(-c3ccc(Cl)cc3)c3ccccc3[nH]c2=O)CC1c1ccc(Cl)s1]

4-(3-(4-(4-chlorophenyl)-2-oxo-1,2-dihydroquinolin-3-yl)-5-(5-chlorothiophen-2-yl)-4,5-dihydro-1H-pyrazol-1-yl)-3,3-difluoro-4-oxobutanoic acid(997-110). Compound 997-110 was prepared via general procedure H. $^1$H NMR (400 MHz, DMSO-d$_6$) δ 12.93 (s, 1H), 12.34 (s, 1H), 7.58 (t, J=7.7 Hz, 1H), 7.53-7.26 (m, 5H), 7.20-7.09 (m, 1H), 7.08-6.99 (m, 1H), 6.90 (t, J=3.6 Hz, 1H), 6.71 (dt, J=7.3, 4.1 Hz, 1H), 5.79-5.69 (m, 1H), 3.76 (td, J=11.6, 5.7 Hz, 1H), 3.33-3.02 (m, 3H).

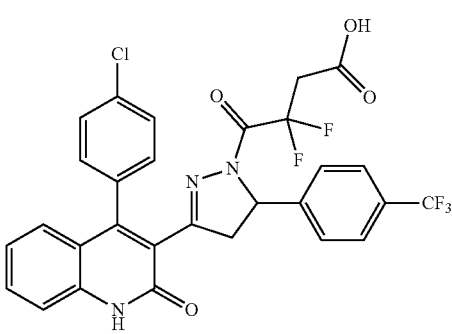 [SMILES: O=C(O)CC(F)(F)C(=O)N1N=C(c2c(-c3ccc(Cl)cc3)c3ccccc3[nH]c2=O)CC1c1ccc(C(F)(F)F)cc1]

4-(3-(4-(4-chlorophenyl)-2-oxo-1,2-dihydroquinolin-3-yl)-5-(4-(trifluoromethyl) phenyl)-4,5-dihydro-1H-pyrazol-1-yl)-3,3-difluoro-4-oxobutanoic acid (997-113). Compound 997-113 was prepared via general procedure H. $^1$H NMR (400 MHz, DMSO-d$_6$) δ 12.97 (s, 1H), 12.34 (s, 1H), 7.65-7.53 (m, 4H), 7.49-7.40 (m, 3H), 7.26 (dd, J=8.2, 2.2 Hz, 1H), 7.15 (ddd, J=8.2, 7.1, 1.2 Hz, 1H), 7.08-7.00 (m, 3H), 5.62 (dd, J=12.0, 4.6 Hz, 1H), 3.94-3.81 (m, 1H), 3.43-3.23 (m, 2H), 2.76 (dd, J=18.8, 4.6 Hz, 1H).

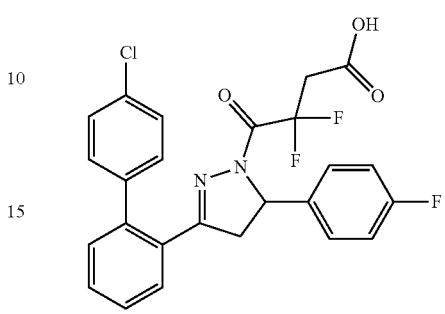

4-(3-(4'-chloro-[1,1'-biphenyl]-2-yl)-5-(4-fluorophenyl)-4,5-dihydro-1H-pyrazol-1-yl)-3,3-difluoro-4-oxobutanoic acid (997-116). Compound 997-116 was prepared via general procedure H. $^1$H NMR (400 MHz, DMSO-d$_6$) δ 12.93 (s, 1H), 7.69 (dd, J=7.5, 1.5 Hz, 1H), 7.60-7.49 (m, 2H), 7.40-7.33 (m, 3H), 7.31-7.27 (m, 2H), 7.17 (dd, J=7.2, 2.5 Hz, 4H), 5.53 (dd, J=11.6, 4.4 Hz, 1H), 3.62 (dd, J=18.4, 11.6 Hz, 1H), 3.20-3.03 (m, 2H), 2.61 (dd, J=18.4, 4.4 Hz, 1H).

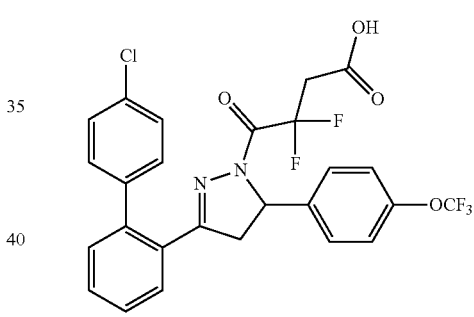

4-(3-(4'-chloro-[1,1'-biphenyl]-2-yl)-5-(4-(trifluoromethoxy)phenyl)-4,5-dihydro-1H-pyrazol-1-yl)-3,3-difluoro-4-oxobutanoic acid (997-117). Compound 997-117 was prepared via general procedure H. $^1$H NMR (400 MHz, DMSO-d$_6$) δ 7.70 (dd, J=7.6, 1.4 Hz, 1H), 7.60-7.49 (m, 2H), 7.40-7.36 (m, 1H), 7.35-7.31 (m, 4H), 7.31-7.25 (m, 4H), 5.57 (dd, J=11.7, 4.4 Hz, 1H), 3.62 (dd, J=18.4, 11.7 Hz, 1H), 3.32-3.04 (m, 2H), 2.61 (dd, J=18.4, 4.4 Hz, 1H).

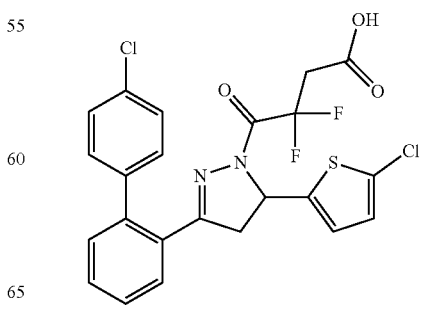

4-(3-(4'-chloro-[1,1'-biphenyl]-2-yl)-5-(5-chlorothiophen-2-yl)-4,5-dihydro-1H-pyrazol-1-yl)-3,3-difluoro-4-oxobutanoic acid (997-118). Compound 997-118 was prepared via general procedure H. $^1$H NMR (400 MHz, DMSO-$d_6$) δ 12.89 (s, 1H), 7.74-7.69 (m, 1H), 7.61-7.49 (m, 2H), 7.41-7.34 (m, 3H), 7.33-7.27 (m, 2H), 6.98-6.81 (m, 2H), 5.76 (dd, J=11.3, 3.8 Hz, 1H), 3.60 (dd, J=18.4, 11.3 Hz, 1H), 3.13-2.95 (m, 2H), 2.89 (dd, J=18.4, 3.9 Hz, 1H).

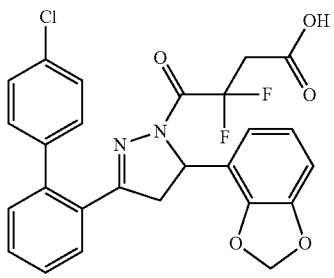 [SMILES: O=C(O)CC(F)(F)C(=O)N1N=C(c2ccccc2-c2ccc(Cl)cc2)CC1c1cccc2c1OCO2]

4-(5-(benzo[d][1,3]dioxol-4-yl)-3-(4'-chloro-[1,1'-biphenyl]-2-yl)-4,5-dihydro-1H-pyrazol-1-yl)-3,3-difluoro-4-oxobutanoic acid (997-119). Compound 997-119 was prepared via general procedure H. $^1$H NMR (400 MHz, DMSO-$d_6$) δ 7.72-7.68 (m, 1H), 7.59-7.46 (m, 2H), 7.40-7.26 (m, 5H), 6.88-6.77 (m, 2H), 6.70-6.60 (m, 1H), 5.99 (dd, J=47.4, 1.0 Hz, 2H), 5.48 (dd, J=11.7, 4.6 Hz, 1H), 3.71-3.57 (m, 1H), 3.42-3.31 (m, 1H), 3.11-2.99 (m, 1H), 2.73 (dd, J=18.2, 4.6 Hz, 1H).

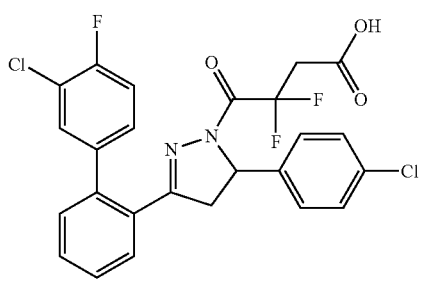 [SMILES: O=C(O)CC(F)(F)C(=O)N1N=C(c2ccccc2-c2ccc(F)c(Cl)c2)CC1c1ccc(Cl)cc1]

4-(3-(3'-chloro-4'-fluoro-[1,1'-biphenyl]-2-yl)-5-(4-chlorophenyl)-4,5-dihydro-1H-pyrazol-1-yl)-3,3-difluoro-4-oxobutanoic acid (997-120). Compound 997-120 was prepared via general procedure H. $^1$H NMR (400 MHz, DMSO-$d_6$) δ 12.78 (s, 1H), 7.74-7.66 (m, 1H), 7.60-7.48 (m, 3H), 7.43-7.34 (m, 4H), 7.31 (ddd, J=8.5, 4.8, 2.2 Hz, 1H), 7.23-7.16 (m, 2H), 5.54 (dd, J=11.7, 4.7 Hz, 1H), 3.90-3.77 (m, 1H), 3.09-2.81 (m, 3H).

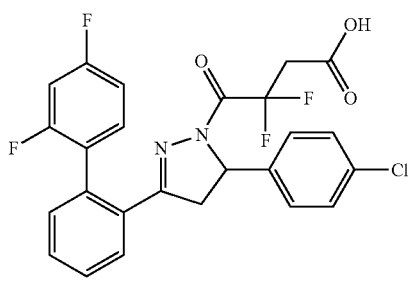 [SMILES: O=C(O)CC(F)(F)C(=O)N1N=C(c2ccccc2-c2ccc(F)cc2F)CC1c1ccc(Cl)cc1]

4-(5-(4-chlorophenyl)-3-(2',4'-difluoro-[1,1'-biphenyl]-2-yl)-4,5-dihydro-1H-pyrazol-1-yl)-3,3-difluoro-4-oxobutanoic acid (997-121). Compound 997-121 was prepared via general procedure H. $^1$H NMR (400 MHz, DMSO-$d_6$) δ 12.74 (s, 1H), 7.75-7.68 (m, 1H), 7.68-7.55 (m, 1H), 7.56 (dt, J=4.8, 2.0 Hz, 1H), 7.57-7.44 (m, 1H), 7.48-7.33 (m, 4H), 7.27-7.09 (m, 4H), 5.56 (dd, J=11.7, 4.7 Hz, 1H), 3.82 (d, J=13.4 Hz, 1H), 3.42-3.20 (m, 2H), 3.00-2.85 (m, 1H).

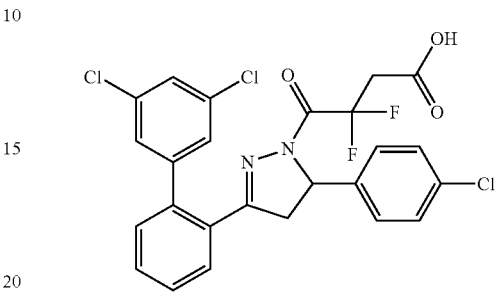

4-(5-(4-chlorophenyl)-3-(3',5'-dichloro-[1,1'-biphenyl]-2-yl)-4,5-dihydro-1H-pyrazol-1-yl)-3,3-difluoro-4-oxobutanoic acid (997-123). Compound 997-123 was prepared via general procedure H. $^{13}$C NMR (100 MHz, DMSO-$d_6$) δ 166.47, 157.23, 144.72, 139.75, 138.30, 137.81, 134.20, 134.13, 131.15, 130.37, 129.52, 129.31, 128.75, 128.62, 127.83, 127.56, 127.51, 127.41, 127.05, 126.88, 126.88, 59.87, 43.42, 24.82, 19.56. HRMS (m/z): [M+H]* calculated for $C_{25}H_{18}O_3N_2Cl_3F_2$, 537.03566; found, 537.03572.

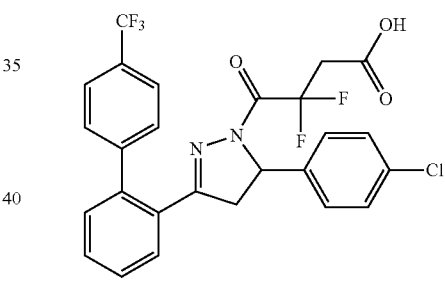

4-(5-(4-chlorophenyl)-3-(4'-(trifluoromethyl)-[1,1'-biphenyl]-2-yl)-4,5-dihydro-1H-pyrazol-1-yl)-3,3-difluoro-4-oxobutanoic acid (997-124). Compound 997-124 was prepared via general procedure H. $^1$H NMR (400 MHz, DMSO-$d_6$) δ 12.82 (s, 1H), 7.80-7.29 (m, 10H), 7.20-7.06 (m, 2H), 5.53 (dd, J=11.6, 4.4 Hz, 1H), 3.86-3.27 (m, 2H), 3.09-2.87 (m, 1H), 2.66 (dd, J=18.4, 4.4 Hz, 1H).

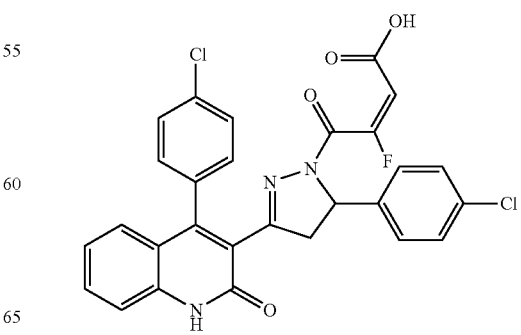

(E)-4-(5-(4-chlorophenyl)-3-(4-(4-chlorophenyl)-2-oxo-1,2-dihydroquinolin-3-yl)-4,5-dihydro-1H-pyrazol-1-yl)-3-fluoro-4-oxobut-2-enoic acid (997-101). 3-fluorofuran-2,5-dione (1 equiv.) was added in a solution of 6 (1 equiv.) in THF (0.045 molar) at room temperature. After around 24 hours, the crude was concentrated in vacuo, washed with ethyl acetate and 1 N HCl. The organic layer was dried over $Mg_2SO_4$, filtered and evaporated in vacuo. Finally, the crude compound was purified by flash chromatography using a 0-10% MeOH/DCM gradient to afford product. $^1$H NMR (400 MHz, DMSO-$d_6$) δ 12.33 (s, 1H), 7.64-7.55 (m, 2H), 7.51 (dd, J=8.2, 2.1 Hz, 1H), 7.46-7.37 (m, 2H), 7.35-7.26 (m, 3H), 7.13 (tt, J=7.0, 1.2 Hz, 1H), 7.06-6.99 (m, 1H), 6.84 (d, J=7.9 Hz, 2H), 6.71-6.59 (m, 1H), 5.42 (dd, J=11.8, 4.5 Hz, 1H), 3.71 (dd, J=18.6, 11.9 Hz, 1H), 2.77 (dd, J=18.6, 4.5 Hz, 1H).

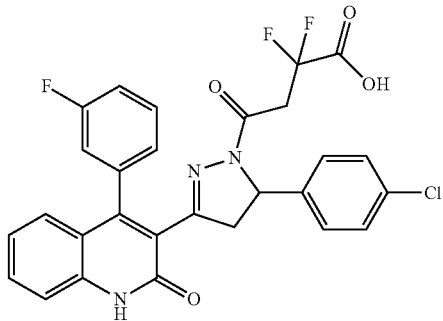

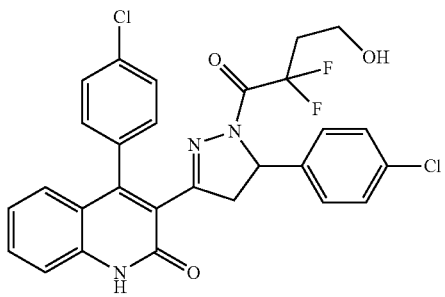 [SMILES: O=C(N1N=C(c2c(-c3ccc(Cl)cc3)c3ccccc3[nH]c2=O)CC1c1ccc(Cl)cc1)C(F)(F)CCO]

4-(4-chlorophenyl)-3-[5-(4-chlorophenyl)-1-(2,2-difluoro-4-hydroxybutanoyl)-4,5-dihydro-1H-pyrazol-3-yl]quinolin-2(1H)-one (997-75). Compound 997-74 (1 equiv.) was dissolved in Tetrahydrofuran (0.03 M) and cooled to 0° C. prior to the borane dimethyl sulfide (1.5 equiv.) was added dropwise under nitrogen. The reaction mixture was stirred at 0° C. for 15 min and then at room temperature overnight. After the mixture was cooling again in an ice bath, methanol was added dropwise until effervescence ceased, and then the mixture was stirred at room temperature for another several minutes. The solvent was then evaporated in vacuo, and the crude was purified by column chromatography. $^1$H NMR (400 MHz, CD$_3$OD) δ 7.62-7.56 (m, 2H), 7.48 (dd, J=8.2, 2.3 Hz, 1H), 7.43 (d, J=7.3 Hz, 1H), 7.42 (dd, J=8.3, 2.1 Hz, 1H), 7.26-7.22 (m, 3H), 7.19 (dd, J=6.8, 1.0 Hz, 1H), 7.16 (dd, J=8.2, 1.8 Hz, 1H), 6.84 (dd, J=9.1, 4.4 Hz, 1H), 6.83 (d, J=8.6 Hz, 1H), 5.44 (dd, J=11.5, 4.4 Hz, 1H), 3.76 (dd, J=18.6, 11.8 Hz, 1H), 3.64 (t, J=6.3 Hz, 2H), 2.72 (dd, J=18.6, 4.3 Hz, 1H), 2.48-2.24 (m, 3H).

General procedure I for the synthesis of difluoro-substituted hydroxybutanoic acid quinolone pyrazoline products. To a solution of acylated quinolone pyrazoline product (1 equiv.) in 1,2-dichloroethane (4.89 mM), trimethyltin hydroxide (5 equiv.) was added in one portion. The mixture was heated at 80° C. and TLC was used to monitor the completion of reaction (1-2 hours). After the reaction was completed, the mixture was evaporated in vacuo, and the residue was taken up in ethyl acetate. The organic layer was washed with aqueous 2 N HCl and then washed with brine, dried over magnesium sulfate and concentrated in vacuo.

4-{5-(4-chlorophenyl)-3-[4-(3-fluorophenyl)-2-oxo-1,2-dihydroquinolin-3-yl]-4,5-dihydro-1H-pyrazol-1-yl}-2,2-difluoro-4-oxobutanoic acid (997-69). Compound 997-69 was prepared via general procedure I using 997-65. $^1$H NMR (400 MHz, CDCl$_3$) δ 12.22 (s, 1H), 7.84 (broad s, 1), 7.58-7.46 (m, 2H), 7.32 (d, J=8.1 Hz, 1H), 7.29-7.13 (m, 6H), 6.98 (dd, J=31.2, 8.4 Hz, 1H), 6.84 (d, J=7.9 Hz, 2H), 5.40 (dd, J=12.0, 3.9 Hz, 1H), 3.90-3.74 (m, 1H), 3.43-3.32 (m, 2H), 2.95 (dd, J=18.5, 3.3 Hz, 1H).

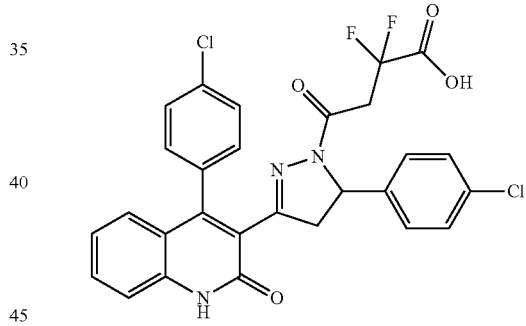

4-(5-(4-chlorophenyl)-3-(4-(4-chlorophenyl)-2-oxo-1,2-dihydroquinolin-3-yl)-4,5-dihydro-1H-pyrazol-1-yl)-2,2-difluoro-4-oxobutanoic acid (997-114). Compound 997-114 was prepared via general procedure I using 997-66. $^1$H NMR (400 MHz, Chloroform-d) δ 12.20 (s, 1H), 11.03 (s, 1H), 7.49 (ddd, J=11.5, 8.3, 3.3 Hz, 2H), 7.43 (dd, J=8.2, 2.2 Hz, 1H), 7.34-7.26 (m, 2H), 7.19-7.08 (m, 5H), 6.75 (d, J=8.1 Hz, 2H), 5.39 (dd, J=11.7, 4.4 Hz, 1H), 3.71 (dd, J=18.5, 11.7 Hz, 1H), 3.43 (td, J=13.1, 4.9 Hz, 2H), 2.80 (dd, J=18.4, 4.3 Hz, 1H).

General procedure J for the synthesis of acylated quinolone pyrazoline products. In a microwaveable vial, compound 12 (1 equiv.) and succinic anhydride were dissolved in Tetrahydrofuran (0.15 M) with molecular sieves. The mixture was microwaved to 165° C. for 20 minutes, checked by LC-MS. The THF was evaporated in vacuo and the resultant residue was washed with DCM and brine. Product was obtained after column chromatography using a flash chromatography system with a 2-10% gradient, using MeOH in DCM.

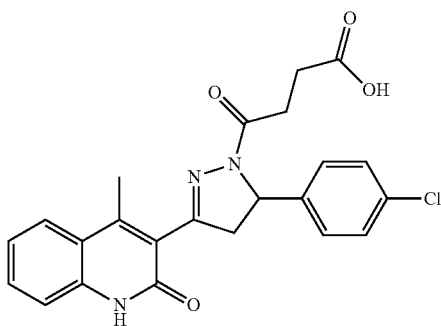 [SMILES: Cc1c(C2=NN(C(=O)CCC(=O)O)C(c3ccc(Cl)cc3)C2)c(=O)[nH]c2ccccc12]

4-(5-(4-chlorophenyl)-3-(4-methyl-2-oxo-1,2-dihydroquinolin-3-yl)-4,5-dihydro-1H-pyrazol-1-yl)-4-oxobutanoic acid (997-76). Compound 997-76 was prepared via general procedure J using 997-77. $^1$H NMR (400 MHz, CD$_3$OD) δ 7.91 (d, J=8.0 Hz, 1H), 7.57 (t, J=7.7 Hz, 1H), 7.37-7.30 (m, 6H), 5.56 (dd, J=11.8, 4.6 Hz, 1H), 3.82 (dd, J=18.5, 11.8 Hz, 1H), 3.24 (dd, J=18.6, 4.3 Hz, 1H), 3.09-2.95 (m, 2H), 2.63 (s, 3H), 2.60 (t, J=6.8 Hz, 2H).

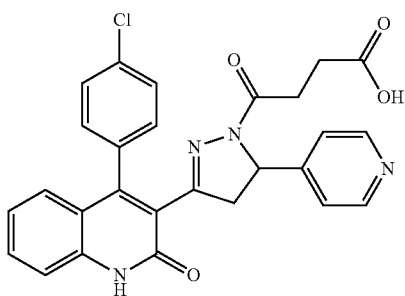 [SMILES: O=C(O)CCC(=O)N1N=C(c2c(-c3ccc(Cl)cc3)c3ccccc3[nH]c2=O)CC1c1ccncc1]

4-(3-(4-(4-chlorophenyl)-2-oxo-1,2-dihydroquinolin-3-yl)-5-(pyridin-4-yl)-4,5-dihydro-1H-pyrazol-1-yl)-4-oxobutanoic acid (997-79). Compound 997-79 was prepared via general procedure J using 12a. $^1$H NMR (400 MHz, CD$_3$OD) δ 8.38 (d, J=3.6 Hz, 2H), 7.56 (dd, J=7.6, 1.2 Hz, 2H), 7.43-7.38 (m, 3H), 7.20-7.12 (m, 3H), 6.94 (d, J=5.1 Hz, 2H), 5.41 (dd, J=12.0, 4.3 Hz, 1H), 3.79 (dd, J=18.6, 12.1 Hz, 1H), 2.92-2.84 (m, 1H), 2.81 (dd, J=18.4, 4.3 Hz, 1H), 2.67-2.44 (m, 3H).

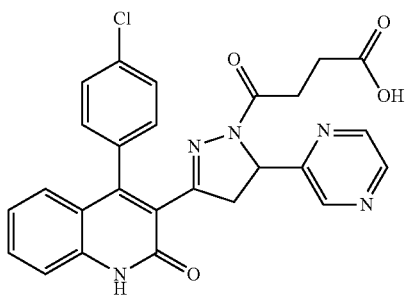 [SMILES: O=C(O)CCC(=O)N1N=C(c2c(-c3ccc(Cl)cc3)c3ccccc3[nH]c2=O)CC1c1cnccn1]

4-(3-(4-(4-chlorophenyl)-2-oxo-1,2-dihydroquinolin-3-yl)-5-(pyrazin-2-yl)-4,5-dihydro-1H-pyrazol-1-yl)-4-oxobutanoic acid (997-80). Compound 997-80 was prepared via general procedure J using 12b. $^1$H NMR (400 MHz, CD$_3$OD) δ 8.51 (d, J=1.1 Hz, 1H), 8.46 (d, J=2.4 Hz, 1H), 8.39 (s, 1H), 7.57 (p, J=4.3 Hz, 1H), 7.45 (td, J=8.8, 2.3 Hz, 2H), 7.40 (d, J=8.5 Hz, 1H), 7.31 (dd, J=7.9, 2.1 Hz, 1H), 7.24 (dd, J=8.1, 2.1 Hz, 1H), 7.17 (d, J=3.9 Hz, 2H), 5.52 (dd, J=11.8, 5.1 Hz, 1H), 3.79 (dd, J=18.2, 12.0 Hz, 1H), 3.15 (dd, J=18.4, 4.9 Hz, 1H), 2.69-2.56 (m, 2H), 2.47-2.43 (m, 2H).

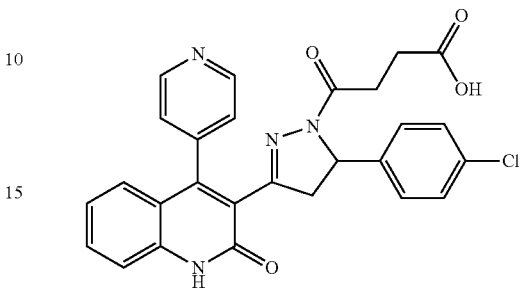

4-(5-(4-chlorophenyl)-3-(2-oxo-4-(pyridin-4-yl)-1,2-dihydroquinolin-3-yl)-4,5-dihydro-1H-pyrazol-1-yl)-4-oxobutanoic acid (997-82). Compound 997-82 was prepared via general procedure J using 997-81. $^1$H NMR (400 MHz, DMSO-d6) δ 12.34 (s, 1H), 12.07 (s, 1H), 8.72 (dd, J=17.8, 5.0 Hz, 2H), 7.60 (t, J=7.1 Hz, 1H), 7.45 (s, 1H), 7.44 (d, J=12.8 Hz, 1H), 7.34 (d, J=4.7 Hz, 1H), 7.30 (d, J=8.5 Hz, 2H), 7.16 (t, J=7.7 Hz, 1H), 6.98 (d, J=7.9 Hz, 1H), 6.86 (d, J=8.6 Hz, 2H), 5.35 (dd, J=11.9, 4.3 Hz, 1H), 3.81 (dd, J=18.4, 12.0 Hz, 1H), 2.92 (dd, J=18.4, 4.6 Hz, 1H), 2.44-2.27 (m, 4H).

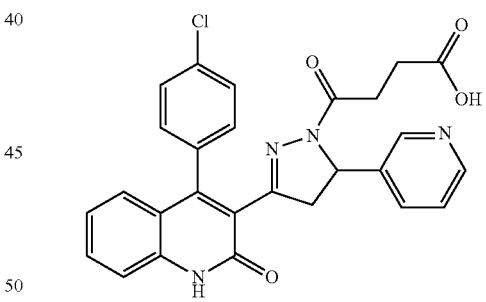

4-(3-(4-(4-chlorophenyl)-2-oxo-1,2-dihydroquinolin-3-yl)-5-(pyridin-3-yl)-4,5-dihydro-1H-pyrazol-1-yl)-4-oxobutanoic acid (997-83). Compound 997-83 was prepared via general procedure J using 12c. $^1$H NMR (400 MHz, CD$_3$OD) δ 8.40 (d, J=3.1 Hz, 1H), 8.35 (s, 1H), 7.61-7.54 (m, 2H), 7.48 (ddd, J=8.2, 3.5, 2.3 Hz, 1H), 7.43-7.36 (m, 2H), 7.35-7.31 (m, 1H), 7.29-7.25 (m, 2H), 7.21-7.15 (m, 2H), 5.47 (dd, J=12.3, 4.1 Hz, 1H), 3.78 (ddd, J=18.5, 11.9, 3.7 Hz, 1H), 3.33 (dd, J=12.0, 3.9 Hz, 1H), 2.96 (dt, J=18.4, 4.1 Hz, 1H), 2.84-2.76 (m, 1H), 2.66-2.58 (m, 1H), 2.50-2.43 (m, 2H).

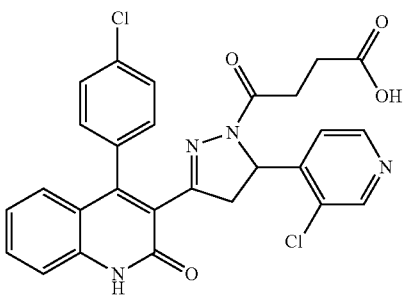 [SMILES: O=C(O)CCC(=O)N1N=C(c2c(-c3ccc(Cl)cc3)c3ccccc3[nH]c2=O)CC1c1ccncc1Cl]

4-(3-(4-(4-chlorophenyl)-2-oxo-1,2-dihydroquinolin-3-yl)-5-(3-chloropyridin-4-yl)-4,5-dihydro-1H-pyrazol-1-yl)-4-oxobutanoic acid (997-88). Compound 997-88 was prepared via general procedure J using 12d. $^1$H NMR (400 MHz, CD$_3$OD) δ 8.50 (s, 1H), 8.34 (d, J=4.7 Hz, 1H), 7.60 (dd, J=8.2, 1.9 Hz, 1H), 7.58 (dd, J=8.2, 1.6 Hz, 1H), 7.56 (dd, J=8.2, 2.3 Hz, 1H), 7.43-7.37 (m, 4H), 7.20-7.14 (m, 3H), 6.67 (d, J=5.1 Hz, 1H), 5.68 (dd, J=12.0, 4.5 Hz, 1H), 3.92 (dd, J=18.4, 12.1 Hz, 1H), 3.01-2.95 (m, 1H), 2.75 (dd, J=18.3, 4.7 Hz, 1H), 2.66-2.48 (m, 3H).

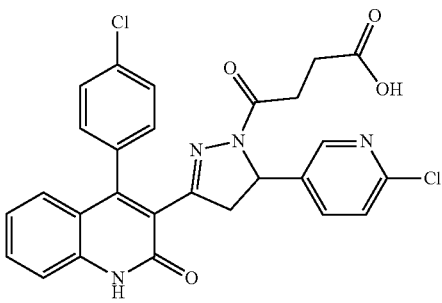 [SMILES: O=C(O)CCC(=O)N1N=C(c2c(-c3ccc(Cl)cc3)c3ccccc3[nH]c2=O)CC1c1ccc(Cl)nc1]

4-(3-(4-(4-chlorophenyl)-2-oxo-1,2-dihydroquinolin-3-yl)-5-(6-chloropyridin-3-yl)-4,5-dihydro-1H-pyrazol-1-yl)-4-oxobutanoic acid (997-92). Compound 997-92 was prepared via general procedure J using 12e. $^1$H NMR (400 MHz, DMSO-d6) δ 12.30 (s, 1H), 12.16 (s, 1H), 8.12 (d, J=2.7 Hz, 1H), 7.57 (d, J=7.8 Hz, 2H), 7.51 (dd, J=8.2, 2.3 Hz, 1H), 7.41 (dd, J=17.8, 8.4 Hz, 3H), 7.32 (dd, J=8.2, 1.9 Hz, 1H), 7.21 (dd, J=8.4, 2.6 Hz, 1H), 7.15 (t, J=7.6 Hz, 1H), 7.04 (d, J=8.2 Hz, 1H), 5.44 (dd, J=11.7, 4.3 Hz, 1H), 3.72 (dd, J=18.5, 12.3 Hz, 1H), 2.93 (dd, J=18.5, 4.1 Hz, 1H), 2.41 (s, 2H). 2.33 (d, J=5.4 Hz, 2H).

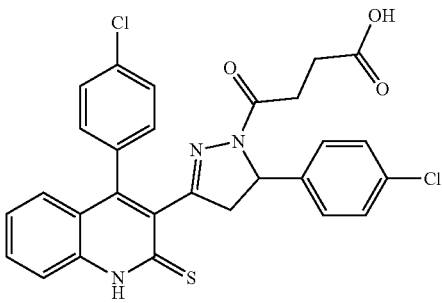 [SMILES: O=C(O)CCC(=O)N1N=C(c2c(-c3ccc(Cl)cc3)c3ccccc3[nH]c2=S)CC1c1ccc(Cl)cc1]

4-(5-(4-chlorophenyl)-3-(4-(4-chlorophenyl)-2-thioxo-1,2-dihydroquinolin-3-yl)-4,5-dihydro-1H-pyrazol-1-yl)-4-oxobutanoic acid (997-97). Compound 997-97 was prepared via general procedure J. $^1$H NMR (400 MHz, DMSO-d$_6$) δ 14.13 (s, 1H), 7.78-7.67 (m, 2H), 7.65 (dd, J=8.2, 2.3 Hz, 1H), 7.46 (ddd, J=12.2, 8.3, 2.2 Hz, 2H), 7.34-7.28 (m, 2H), 7.28-7.22 (m, 2H), 7.07 (dd, J=8.1, 1.2 Hz, 1H), 6.80 (d, J=8.1 Hz, 2H), 5.33 (dd, J=12.1, 5.0 Hz, 1H), 3.91-3.78 (m, 1H), 2.73 (dt, J=17.2, 6.8 Hz, 2H), 2.59 (dt, J=17.1, 6.6 Hz, 1H), 2.36 (t, J=7.1

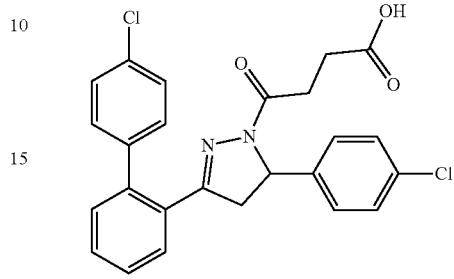

4-(3-(4'-chloro-[1,1'-biphenyl]-2-yl)-5-(4-chlorophenyl)-4,5-dihydro-1H-pyrazol-1-yl)-4-oxobutanoic acid (997-99). Compound 997-99 was prepared via general procedure J. $^1$H NMR (400 MHz, Chloroform-d) δ 7.66 (dd, J=7.4, 1.7 Hz, 1H), 7.50-7.40 (m, 2H), 7.31 (dd, J=7.2, 1.7 Hz, 1H), 7.27-7.20 (m, 4H), 7.19-7.13 (m, 2H), 7.00-6.94 (m, 2H), 5.37 (dd, J=11.6, 4.2 Hz, 1H), 3.20 (dd, J=17.9, 11.6 Hz, 1H), 3.01-2.79 (m, 2H), 2.67 (t, J=6.3 Hz, 2H), 2.45 (dd, J=17.9, 4.2 Hz, 1H).

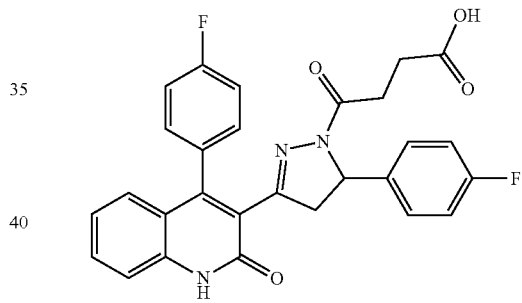

4-(5-(4-fluorophenyl)-3-(4-(4-fluorophenyl)-2-oxo-1,2-dihydroquinolin-3-yl)-4,5-dihydro-1H-pyrazol-1-yl)-4-oxobutanoic acid (997-105). Compound 997-105 was prepared via general procedure J. $^1$H NMR (400 MHz, Methanol-d$_4$) δ 7.64-7.51 (m, 1H), 7.41 (dd, J=9.5, 5.0 Hz, 2H), 7.33-7.13 (m, 8H), 6.95-6.87 (m, 3H), 5.35 (dd, J=11.8, 4.4 Hz, 1H), 3.80-3.59 (m, 2H), 2.89-2.61 (m, 2H), 2.55-2.39 (m, 2H).

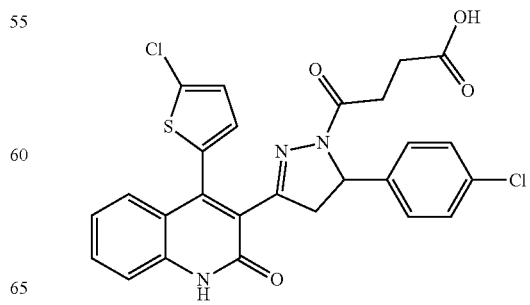

4-(5-(4-chlorophenyl)-3-(4-(5-chlorothiophen-2-yl)-2-oxo-1,2-dihydroquinolin-3-yl)-4,5-dihydro-1H-pyrazol-1-yl)-4-oxobutanoic acid (997-108). Compound 997-108 was prepared via general procedure J. $^1$H NMR (400 MHz, DMSO-d$_6$) δ 12.34 (s, 1H), 12.08 (s, 1H), 7.59 (ddt, J=8.4, 7.1, 1.7 Hz, 1H), 7.39 (ddt, J=14.6, 8.3, 1.7 Hz, 2H), 7.32 (dd, J=8.9, 2.2 Hz, 2H), 7.25 (t, J=3.4 Hz, 1H), 7.20 (ddt, J=8.2, 7.1, 1.6 Hz, 1H), 7.07 (t, J=3.2 Hz, 1H), 7.03-6.95 (m, 2H), 5.44 (dt, J=12.0, 3.6 Hz, 1H), 3.77 (ddd, J=18.3, 12.0, 2.4 Hz, 1H), 2.85 (dt, J=18.4, 3.6 Hz, 1H), 2.77-2.54 (m, 2H), 39 (ddd, J 14.3, 6.8, 1.9 Hz, 2H).

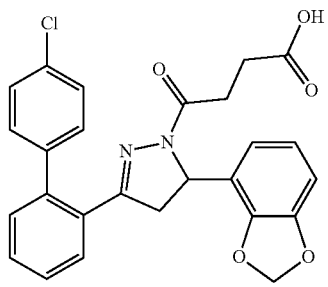

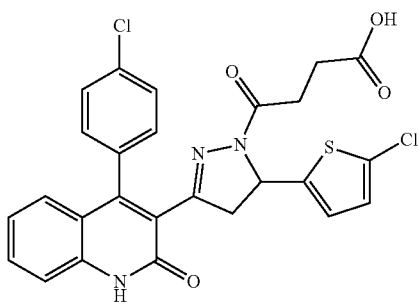 [SMILES: O=C(O)CCC(=O)N1N=C(c2c(-c3ccc(Cl)cc3)c3ccccc3[nH]c2=O)CC1c1ccc(Cl)s1]

4-(3-(4-(4-chlorophenyl)-2-oxo-1,2-dihydroquinolin-3-yl)-5-(5-chlorothiophen-2-yl)-4,5-dihydro-1H-pyrazol-1-yl)-4-oxobutanoic acid (997-111). Compound 997-111 was prepared via general procedure J. $^1$H NMR (400 MHz, DMSO-d$_6$) δ 12.40 (s, 1H), 12.22 (s, 1H), 7.73-7.61 (m, 2H), 7.51 (dddd, J=44.8, 15.2, 6.5, 2.4 Hz, 4H), 7.26 (q, J=8.7, 7.6 Hz, 1H), 7.15 (d, J=8.2 Hz, 1H), 7.00 (dt, J=6.2, 3.0 Hz, 1H), 6.79 (q, J=4.1, 3.4 Hz, 1H), 5.67 (dt, J=11.3, 3.1 Hz, 1H), 3.76 (ddd, J=18.2, 11.4, 2.0 Hz, 1H), 3.26 (dt, J=18.2, 3.0 Hz, 1H), 2.70-2.42 (m, 4H).

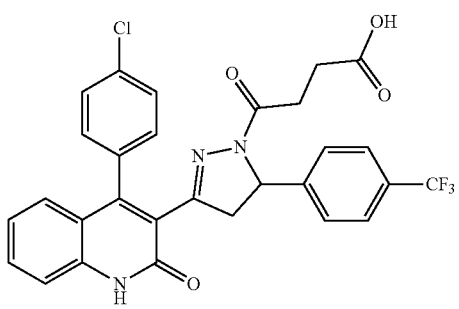 [SMILES: O=C(O)CCC(=O)N1N=C(c2c(-c3ccc(Cl)cc3)c3ccccc3[nH]c2=O)CC1c1ccc(C(F)(F)F)cc1]

4-(3-(4-(4-chlorophenyl)-2-oxo-1,2-dihydroquinolin-3-yl)-5-(4-(trifluoromethyl) phenyl)-4,5-dihydro-1H-pyrazol-1-yl)-4-oxobutanoic acid (997-112). Compound 997-112 was prepared via general procedure J. $^1$H NMR (400 MHz, DMSO-d$_6$) δ 7.63-7.54 (m, 4H), 7.47 (dd, J=8.2, 2.3 Hz, 1H), 7.43 (dd, J=8.2, 2.0 Hz, 2H), 7.27 (dd, J=8.2, 2.2 Hz, 1H), 7.14 (ddd, J=8.3, 7.1, 1.2 Hz, 1H), 7.05-6.98 (m, 3H), 5.45 (dd, J=12.1, 4.5 Hz, 1H), 3.77 (dd, J=18.5, 12.1 Hz, 1H), 2.76 (dd, J=18.5, 4.5 Hz, 1H), 2.68-2.44 (m, 2H), 2.33 (t, J=7.1 Hz, 2H).

4-(5-(benzo[d][1,3]dioxol-4-yl)-3-(4'-chloro-[1,1'-biphenyl]-2-yl)-4,5-dihydro-1H-pyrazol-1-yl)-4-oxobutanoic acid (997-122). Compound 997-122 was prepared via general procedure J. $^1$H NMR (400 MHz, DMSO-d$_6$) δ 12.19 (s, 1H), 7.72 (dd, J=7.6, 1.5 Hz, 1H), 7.54 (dtd, J=18.2, 7.4, 1.5 Hz, 2H), 7.43-7.36 (m, 1H), 7.34-7.24 (m, 4H), 6.90-6.76 (m, 2H), 6.52 (dd, J=7.9, 1.2 Hz, 1H), 5.98 (dd, J=33.7, 1.0 Hz, 2H), 5.39 (dd, J=11.7, 4.3 Hz, 1H), 3.42 (dd, J=17.9, 11.8 Hz, 1H), 2.72-2.56 (m, 2H), 2.55-2.51 (m, 1H), 2.40 (t, J=6.7 Hz, 2H).

General procedure K for the synthesis of difluoro-4-oxobutanamide. In a round-bottomed flask, difluoro-substituted carboxylic acid (1 equiv.) was dissolved in DCM (0.3 M). Then oxalyl dichloride (2.5 equiv.) was added dropwise, followed by on drop of DMF. The reaction was stirred for approximately 40 minutes. The solvent and excess oxalyl dichloride was removed under vacuum and the product was obtained by Kugelrohr distillation at 98° C. with full vacuum. Used immediately. Then a solution of resultant compound in DCM was added slowly to excess ammonia solution (0.5 M in dioxane) under nitrogen. The mixture was stirred at room temperature overnight. The completion of the reaction was monitored by LC-MS. The solvent was evaporated in vacuo, and the crude was purified by amine column chromatography using 0-10% MeOH/DCM gradient.

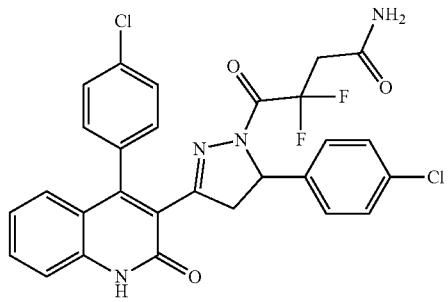 [SMILES: NC(=O)CC(F)(F)C(=O)N1N=C(c2c(-c3ccc(Cl)cc3)c3ccccc3[nH]c2=O)CC1c1ccc(Cl)cc1]

4-(5-(4-chlorophenyl)-3-(4-(4-chlorophenyl)-2-oxo-1,2-dihydroquinolin-3-yl)-4,5-dihydro-1H-pyrazol-1-yl)-3,3-difluoro-4-oxobutanamide (997-96). Compound 997-96 was prepared via general procedure K using 997-74. $^1$H NMR (400 MHz, DMSO-d$_6$) δ 12.31 (s, 1H), 7.62-7.46 (m, 3H), 7.42 (dtd, J=8.3, 4.2, 2.5 Hz, 2H), 7.34-7.21 (m, 3H), 7.19-7.10 (m, 2H), 7.06-6.99 (m, 1H), 6.95-6.90 (m, 1H), 5.53-5.42 (m, 1H), 3.85-3.72 (m, 1H), 3.26-3.00 (m, 2H), 2.70 (ddd, J=18.5, 4.6, 1.5 Hz, 1H).

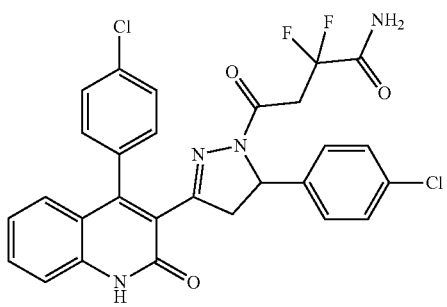 [SMILES: NC(=O)C(F)(F)CC(=O)N1N=C(c2c(-c3ccc(Cl)cc3)c3ccccc3[nH]c2=O)CC1c1ccc(Cl)cc1]

4-(5-(4-chlorophenyl)-3-(4-(4-chlorophenyl)-2-oxo-1,2-dihydroquinolin-3-yl)-4,5-dihydro-1H-pyrazol-1-yl)-2,2-difluoro-4-oxobutanamide (997-115). Compound 997-115 was prepared via general procedure K using 997-114. $^1$H NMR (400 MHz, DMSO-$d_6$) δ 12.31 (s, 1H), 7.87 (d, J=79.1 Hz, 2H), 7.64-7.51 (m, 3H), 7.43 (dt, J=8.3, 1.9 Hz, 2H), 7.30 (dq, J=9.3, 2.4 Hz, 3H), 7.15 (ddd, J=8.2, 7.0, 1.2 Hz, 1H), 7.03 (dd, J=8.2, 1.4 Hz, 1H), 6.88-6.82 (m, 2H), 5.37 (dd, J=11.9, 4.4 Hz, 1H), 3.82-3.70 (m, 1H), 3.37-3.09 (m, 2H), 2.85 (dd, J=18.6, 4.4 Hz, 1H).

Evaluation of Enantiomers

Reverse phase chiral chromatography was used to separate racemic compounds by using a ChiralPak OD-RH column (30 mm×250 mm, 5 μM). The racemic compound was dissolved in methanol and diluted with a solvent of 60% ACN (0.1% Formic acid): 40% $H_2O$ (0.1% Formic acid). The system was pre-flashed with 60% ACN (0.1% Formic acid): 40% $H_2O$ (0.1% Formic acid) and then the sample was injected into the system (4-6 ml per injection with 2-3 mg/ml compound) with flow rate of 10 ml/min. One enantiomer came out around 17-18 minutes, while the other enantiomer came out around 21 minutes. Optical rotation values of the enantiomers were evaluated via a Perkin-Elmer 314 instrument.

X-Ray Crystallography

Single colorless plate-shaped crystals (+) 997-74 were recrystallized by methanol and ethyl acetate. A suitable crystal (0.50*0.40*0.18) was selected and mounted on a loop with paratone oil on a Bruker APEX-II CCD diffractometer. The crystal was cooled to T=100(2) K operated by an Oxford Cryosystems low-temperature apparatus during the data collection. The structure was solved using Olex2 (Dolomanov et al., 2009) as the graphical interface for the crystallographic calculation and with Superflip (L. palatinus & G. Chapuis, 2007) via the Charge Flipping solution method. The model was refined with ShelXL-97 (Sheldrick, 2008) by using Least Squares minimization. Crystal Data: $C_{30}H_{25}Cl_2F_2N_3O_5$, $M_r$=616.43, monoclinic, P2$_1$ (No. 4), a=8.2731(9) Å, b=9.5335(10) Å, c=18.434(2) Å, β=94.719(2)°, α=γ=90°, V=1449.0(3) Å$^3$, T=100(2) K, Z=2, Z'=1, μ(MoK$_α$)=0.282, 18906 reflections measured, 8732 unique ($R_{int}$=0.0223) which were used in all calculations. The final wR$_2$ was 0.0856 (all data) and R$_1$ was 0.0335 (I>2(I)). Crystal was selected and solved by Marika Wieliczko and John Bacsa, Ph.D. at the Emory X-crystallography core facility.

Two-Electrode Voltage-Clamp Recording

Two-electrode voltage-clamp recordings were performed in Xenopus laevis oocytes that were injected with mRNA to express recombinant rat GluN1/GluN2A, GluN1/GluN2B, GluN1/GluN2C, and GluN1/GluN2D. The recordings using unfertilized oocytes from Xenopus laevis were permitted by Emory University Institutional Animal Care and Use Committee (IACUC). An automatic injector (Nanoject II, Drummond Scientific) was used for cRNA injection using the pipettes filled with mineral oil. The cRNA that transcribed in vitro via the mMessage Machine kit (Ambion) was diluted with nuclease-free water, and then injected at GluN1/GluN2 with a ratio of 1:2. The oocytes were stored in Barth's solution that contained 88 mM NaCl, 5.0 mM Tris-HCl, 2.4 mM NaHCO$_3$, 1.0 mM KCl, 0.84 mM MgSO$_4$, 0.41 mM CaCl$_2$), 0.33 mM Ca(NO$_3$)$_2$, 0.1 mg/ml gentamycin sulfate, 1.0 U/ml penicillin, and 1 μg/ml streptomycin at a pH of 7.4 and temperatures of 15-17° C. for two to five days before the two-electrode voltage-clamp recordings. When recording, the oocytes were placed in a perfusion chamber and continually washed with the recording solution comprised of 90 mM NaCl, 1.0 mM KCl, 0.50 mM BaCl$_2$, 0.005 mM EDTA, and 10 mM HEPES at a pH of 7.4 and a temperature of 23° C. Glass electrodes with a tip resistance of 0.5 to 2.5 MΩ were obtained from thin-walled glass capillary tubes. Voltage electrodes and current electrodes were filled with 0.3 M and 3.0 M KC, respectively. The recordings were executed with the oocytes membrane potential holding at −40 mV by an OC-725 amplifier (Warner Instrument Co). All compounds were dissolved in dimethyl sulfoxide (DMSO) as 20 mM stock solutions and future diluted to reach the desired concentration (0.05-0.5% (vol/vol) DMSO) in recording solution comprised of 30 μM glycine and 100 μM glutamate. Each compound was recorded 3-7 times in the least 4 oocytes from at least 2 different Xenopus laevis.

Data Analysis

To evaluate the inhibition of compounds, the concentration-response curve was fitted with the average two-electrode voltage-clamp recording results with the equation $$\text{response}=100/\{1+[(\text{inhibitor concentration})/IC_{50}]^N\}$$

where IC$_{50}$ is the concentration of compounds that inhibit half maximal of the current response and N is the Hill slope. Compounds with less than 30% inhibition at 30 μM will display NE (not effective) in the figures.

Figure 2:
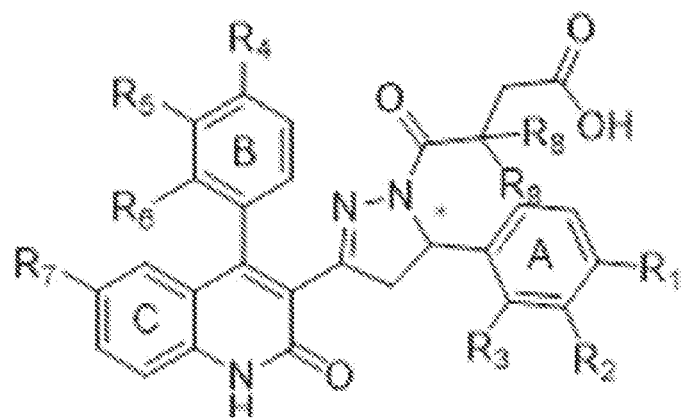
FIG. 2 shows the proposed pharmacophore features that contribute to the GluN2D inhibition as found from an SAR study of the 997 series. The (S)-enantiomer is preferred. Halogen groups on $R_1$ are preferred (R1=Cl is most active). Thiophene ring is more selective. Halogen groups on $R_4$ and $R_5$ are tolerated, $R_4$=Cl is most active. Functional groups are tolerated but not preferred on $R_7$. Quinolone is more active than phenyl group. Both O/S are tolerated, O is more active. $R_8$=F is much more active than $R_8$=H. Both carboxylic acid and amide are tolerated, and the acid is more active in vitro.

This disclosure describes a series of optimization of GluN2D-selective antagonists of the NMDA receptors with DQP scaffold. Among compounds in 997-series, compound (S)-997-74 is the most potent antagonist of the GluN2D-containing receptors with an IC$_{50}$ value of 46 nM. In addition, compound 997-110 is 625-fold more selective at the GluN2D subunits than that at the GluN2B subunits. From the SAR study of 997-series, the proposed pharmacophore features that contribute to the GluN2D inhibition are shown in FIG. 2.

The halogen groups are preferred on the A- and B-rings. Compounds with an electronegative chlorine substitution at the para-position on both rings are always more active than those with other substitutions. Replacing the phenyl A-ring by thiophene improves the selectivity at GuN2D subunits over GluN2B subunits. More potent compounds prefer a quinolone ring on the bottom with no substitution rather than phenyl group. Furthermore, compounds with difluoro-substitution are invariably more potent than the related compounds without difluoro-substitution at the GuN2D-containing receptors. Although the carboxylic acid and amide groups are tolerated on the terminal of acyl chain, compounds with carboxylic acid present the better-inhibited activity at the GuN2D subunits in vitro. According to the enantiomer separation and the absolute stereochemistry determination, the(S)-enantiomers are always more potent than their racemic compounds, while the (R)-enantiomers significantly decrease the activity at the GuN2D subunits.

With the optimization of GluN2C and GluN2D-selective antagonists, number of neurological diseases could be prevented or treated. For example, the GluN2C-selective antagonists are hypothesized to participate in emotional learning and schizophrenia. Additionally, the GluN21D-selective antagonists may decrease $Ca^{2+}$ influx into dopaminergic neurons and rectify circuit imbalance due to the dopamine depletion of Parkinson's disease. Therefore, an improvement of GluN2C/D-selective antagonists would have a significant role in the brain. We have leveraged the 997-project to the next stage with many years' efforts.

Concentration-response data for 997-enantiomers at ionotropic glutamate receptors.

| 997- | $I_{3 \mu M}/I_{control}$ (mean ± SEM, %) | | | | Avg. GluN2C $IC_{50}$ (μM) (95% CI) | Avg. GluN2D $IC_{50}$ (μM) (95% CI) |
|---|---|---|---|---|---|---|
| | GluN2A | GluN2B | GluN2C | GluN2D | | |
| (−)-67 | 100 ± 0.89 | 95 ± 2.2 | 42 ± 2.8 | 26 ± 3.2 | 2.71 (1.93-3.82) | 0.97 (0.68-1.40) |
| (+)-67 | 98 ± 2.1 | 87 ± 2.8 | 74 ± 2.1 | 57 ± 3.5 | ND | 7.02 (4.44-11.10) |
| (−)-74 | 67 ± 3.9 | 73 ± 4.8 | 9.3 ± 1.8 | 3.5 ± 1.0 | 0.11 (0.10-0.14) | 0.055 (0.048-0.06) |
| (+)-74 | 95 ± 0.47 | 87 ± 1.4 | 56 ± 3.8 | 55 ± 2.7 | 3.10 (1.14-8.44) | 2.24 (1.20-4.18) |
| (−)-90 | 33 ± 4.5 | 34 ± 5.0 | 7.0 ± 2.2 | 3.4 ± 1.2 | 0.21 (0.18-0.25) | 0.13 (0.11-0.15) |
| (+)-90 | 72 ± 2.9 | 53 ± 3.6 | 36 ± 3.0 | 31 ± 9.8** | 2.10 (1.73-2.55) | 0.66 (0.37-1.19) |

Data show the current response of co-application of 3 μM of each compound with 100 μM glutamate and 30 μM glycine.
The current response of control is set as 1.
Data with ** show the current response of co-application of 1 μM of each compound with 100 μM glutamate and 30 μM glycine.
Data are from between 2 and 15 oocytes from 1 to 4 frogs for each compound and receptor tested.
The last column shows the mean $IC_{50}$ values of each compound with bottom and top 95% confidence interval.
ND (not determined) indicates that the initial values generated a curve that didn't come close to the points.

REFERENCES

[1] Traynelis, S. F., et al., Pharmacological reviews, 2010. 62(3): p. 405-496.
[2] Acker, T. M., et al., Molecular pharmacology, 2011. 80(5): p. 782-795.
[8] Yuan, H., et al., Molecular pharmacology, 2015. 88(1): p. 203-217.
[9] Karakas, E. and H. Furukawa, Science, 2014. 344(6187): p. 992-997.
[10] Gielen, M., et al., Nature, 2009. 459(7247): p. 703.
[11] Vance, K. M., et al., Nature communications, 2011. 2: p. 294.
[12] Yuan, H., et al., Journal of Neuroscience, 2009. 29(39): p. 12045-12058.
[13] Karakas, E., N. Simorowski, and H. Furukawa, Nature, 2011. 475(7355): p. 249.
[14] Furukawa, H. and E. Gouaux, The EMBO journal, 2003. 22(12): p. 2873-2885.
[15] Rachline, J., et al., Journal of Neuroscience, 2005. 25(2): p. 308-317.
[16] Hansen, K. B. et al., Molecular pharmacology, 2010. 78(4): p. 535-549.
[17] Hansen, et al., Journal of Neuroscience, 2012. 32(18): p. 6197-6208.
[18] Furukawa, H., et al., Nature, 2005. 438(7065): p. 185.
[19] Santangelo, R. M., et al., Expert opinion on therapeutic patents, 2012. 22(11): p. 1337-1352.
[20] Akazawa, C., et al., Journal of Comparative Neurology, 1994. 347(1): p. 150-160.
[21] Paoletti, P., European Journal of Neuroscience, 2011. 33(8): p. 1351-1365.
[22] Nicholls, D. G., Journal of Neurochemistry, 1989. 52(2): p. 331-341.
[23] Errico, F., et al., Journal of Neuroscience, 2008. 28(41): p. 10404-10414.
[24] Fleck, M., et al., Journal of Neuroscience, 1993. 13(9): p. 3944-3955.
[25] Yao, Y. and M. L. Mayer, Journal of Neuroscience, 2006. 26(17): p. 4559-4566.
[26] Kemp, J., et al., PNAS, 1988. 85(17): p. 6547-6550.
[27] McNamara, D., et al., Neuroscience letters, 1990. 120(1): p. 17-20.
[28] Kinarsky, L., et al., J. Pharmacol. Exp. Therap., 2005. 313(3): p. 1066-1074.
[29] Parsons, C., W. Danysz, and G. Quack, Neuropharmacology, 1999. 38(6): p. 735-767.
[30] Blanpied, T. A., et al., Journal of Neurophysiology, 1997. 77(1): p. 309-323.
[31] Huettner, J. E. and B. P. Bean, PNAS, 1988. 85(4): p. 1307-1311.
[32] Strong, K. L., et al., Expert opinion on therapeutic patents, 2014. 24(12): p. 1349-1366.
[33] Chen, H. S. V and S. A. Lipton, Journal of neurochemistry, 2006. 97(6): p. 1611-1626.
[34] Church, J., D. Lodge, and S. C. Berry,. Eur. J. Pharmacol., 1985. 111(2): p. 185-190.
[35] Franklin, P. H. and T. F. Murray, Molecular pharmacology, 1992. 41(1): p. 134-146.
[36] Wong, E., et al., PNAS, 1986. 83(18): p. 7104-7108.
[37] WW Hasselmann, H., Current neuropharmacology, 2014. 12(1): p. 57-70.
[38] Jentsch, J. D. and R. H. Roth, Neuropsychopharmacology, 1999. 20(3): p. 201-225.
[39] Parsons, C., et al., Neuropharmacology, 1995. 34(10): p. 1239-1258.
[40] Williams, K., Molecular pharmacology, 1993. 44(4): p. 851-859.
[41] Chenard, B., et al., Journal of medicinal chemistry, 1995. 38(16): p. 3138-3145.
[42] Fischer, G., et al., J. Pharmacol. Exp. Therap., 1997. 283(3): p. 1285-1292.
[43] Hansen, K. B. and S.F. Traynelis, Journal of Neuroscience, 2011. 31(10): p. 3650-3661.
[44] Edman, S., et al., Neuropharmacology, 2012. 63(3): p. 441-449.
[45] Irvine, M. W., et al., Neurochemistry international, 2012. 61(4): p. 593-600.
[46] Monaghan, D. T., et al., Neurochemistry international, 2012. 61(4): p. 581-592.
[47] Costa, B. M., et al., J. Pharmacol. Exp. Therap., 2010. 335(3): p. 614-621.

[48] Santangelo Freel, R. M., et al., J. Med. Chem., 2014. 57(11): p. 4975-4975.
[49] Santangelo Freel, R. M., et al., J. Med. Chem., 2013. 56(13): p. 5351-5381.
[50] Ogden, K.K. and S.F. Traynelis, Molecular pharmacology, 2013. 83(5): p. 1045-1056.
[51] Mullasseril, P., et al., Nature communications, 2010. 1: p. 90.
[52] Zimmerman, S. S., et al., J. Med. Chem., 2014. 57(6): p. 2334-2356.
[53] Khatri, A., et al., Molecular pharmacology, 2014. 86(5): p. 548-560.
[54] Barbeau, A., Canadian Medical Association Journal, 1969. 101(13): p. 59.
[55] Crosby, N.J., et al., Amantadine in Parkinson's disease. The Cochrane Library, 2003.
[56] Crosby, N.J., et al., Amantadine for dyskinesia in Parkinson's. The Cochrane Library, 2003.
[57] Bravo, S. A., et al., A Synopsis of Parkinson's Disease. 2014, InTech.
[58] Pantcheva, P., et al., Expert review of neurotherapeutics, 2015. 15(10): p. 1231-1240.
[59] Savitt, J. M., et al., The Journal of Clinical investigation, 2006. 116(7): p. 1744-1754.
[60] Standaert, D. G., et al., Journal of Comparative Neurology, 1994. 343(1): p. 1-16.
[61] Wenzel, A., et al., Journal of neurochemistry, 1996. 66(3): p. 1240-1248.
[62] Swanger, S. A., et al., Journal of Neuroscience, 2015. 35(48): p. 15971-15983.
[63] Monyer, H., et al., Neuron, 1994. 12(3): p. 529-540.
[64] Lanciego, J. L., eta., Cold Spring Harbor perspectives in medicine, 2012. 2(12): p. a009621.
[65] Nelson, A. B. and A. C. Kreitzer, Annual review of neuroscience, 2014. 37: p. 117-135.
[66] Ikemoto, S., C. Yang, and A. Tan, Behavioural brain research, 2015. 290: p. 17-31.
[67] DeLong, M. and T. Wichmann, Clinical EEG and neuroscience, 2010. 41(2): p. 61-67.
[68] Alexander, G. E., Dialogues in clinical neuroscience, 2004. 6(3): p. 259.
[69] Gardoni, F. and C. Bellone, Frontiers in cellular neuroscience, 2015. 9: p. 25.
[70] Olivares, D., et al., Current Alzheimer Research, 2012. 9(6): p. 746-758.
[71] More, S. V. and D.-K. Choi, Molecular neurodegeneration, 2015. 10(1): p. 17.
[72] Hallett, P. J. and D. G. Standaert, Pharmacology & therapeutics, 2004. 102(2): p. 155-174.
[73] Johnson, K. A., et al., CNS & Neurological Disorders-Drug Targets, 2009. 8(6): p. 475-491.
[74] Caligiore, D., et al., NPJ Parkinson's disease, 2016. 2: p. 16025.
[75] Mosley, C. A., et al., Journal of medicinal chemistry, 2010. 53(15): p. 5476-5490.
[76] Hansen, K. B., et al., J. Pharmacol. Exp. Therap., 2010. 333(3): p. 650-662.
[77] Acker, T. M., et al., J. Med. Chem, 2013. 56(16): p. 6434-6456.
[78] Wang, Q., et al., International journal of pharmaceutics, 2005. 288(2): p. 349-359.
[79] Frye, S. V., et al., The Journal of Organic Chemistry, 1991. 56(11): p. 3750-3752.
[80] Jia, C.-S., et al., Tetrahedron, 2007. 63(4): p. 892-897.
[81] Draper, J. M., et al., Molecular cancer therapeutics, 2011. 10(11): p. 2052-2061.
[82] Xu, F., et al., The Journal of organic chemistry, 2005. 70(15): p. 6105-6107.
[83] Partridge, J. J., S.-J. Shiuey, and M. R. Uskokovic, U.S. Pat. No. 4,421,690A.
[84] Abell, A. D., et al., The Journal of Organic Chemistry, 1990. 55(18): p. 5217-5221.
[85] Kendrick, D. A., et al., Journal of medicinal chemistry, 1989. 32(1): p. 170-173.
[86] Nicolaou, K., et al., Angewandte Chemie International Edition, 2005. 44(9): p. 1378-1382.

What is claimed is:

1. A compound of Formula (I) or a salt thereof,

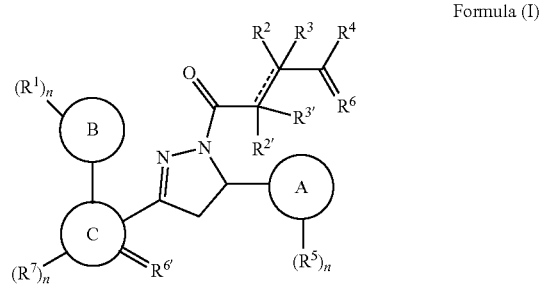

Formula (I)

wherein $R^1$ and $R^5$, in each occurrence, are individually and independently a halogen;
wherein $R^7$, in each occurrence, is individually and independently a C1 to C3 alkyl, alkoxy, halogen or trifluoroalkyl;
wherein $R^2$, $R^3$, $R^{2'}$ and $R^{3'}$ are individually and independently H or a halogen;
wherein $R^4$ is an amino, hydroxyl or C1 to C3 alkoxy;
wherein $R^6$ and $R^{6'}$ are individually and independently S, O or absent;
wherein $R^6$ is absent, the carbon connected to $R^6$ is —CH$_2$—;
wherein Ring B is a 5 or 6 membered aryl or heteroaryl;
wherein Ring A is thiophene or furan;
wherein Ring C is a monocyclic or bicyclic aryl or heteroaryl ring;
wherein the dashed bond represented by ==== is a single bond or a double bond;
wherein when the dashed bond represented by ==== is a double bond, $R^3$ and $R^{3'}$ are absent;
wherein, for Ring A and Ring B, n, in each occurrence, is individually and dependently 1, 2 or 3;
wherein, for Ring C, n is 0, 1, 2 or 3; and
wherein $R^2$, $R^3$, $R^{2'}$, $R^{3'}$, $R^4$, and $R^7$ are, individually and independently, optionally substituted with $R^{10}$, which is a halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein $R^4$ is NH$_2$, OH, OMe or OEt.

3. The compound of claim 1, wherein $R^{6'}$ is a S or O when Ring C is a bicyclic aryl or heteroaryl ring or is absent when Ring C is a monocyclic aryl or heteroaryl ring.

4. The compound of claim 1, wherein $R^1$ and $R^5$, in each occurrence, are individually and independently chloro or fluoro.

5. The compound of claim 1, wherein each of $R^2$ and $R^3$ is a fluoro when each of $R^{2'}$ and $R^{3'}$ is H or wherein each of $R^2$ and $R^3$ is a H when each of $R^{2'}$ and $R^{3'}$ is fluoro.

6. The compound of claim 1, wherein Ring B is a phenyl, pyridine, pyrazine or thiophene and Ring C is a phenyl or a quinolinone or quinolinethione ring system.

7. The compound of claim 1, wherein Ring B, when considered together with its $R^1$ substitutent(s), is:

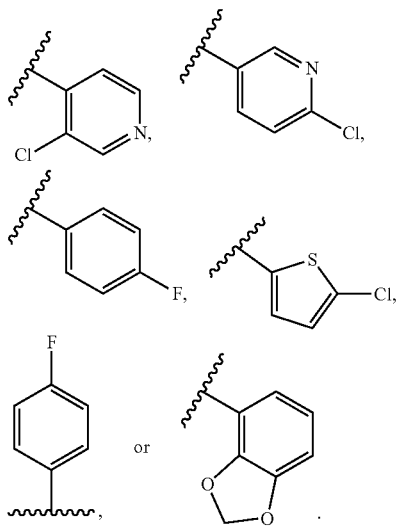

8. The compound of claim 1, which is a compound of Formula (IC) or (ID), or a salt thereof:

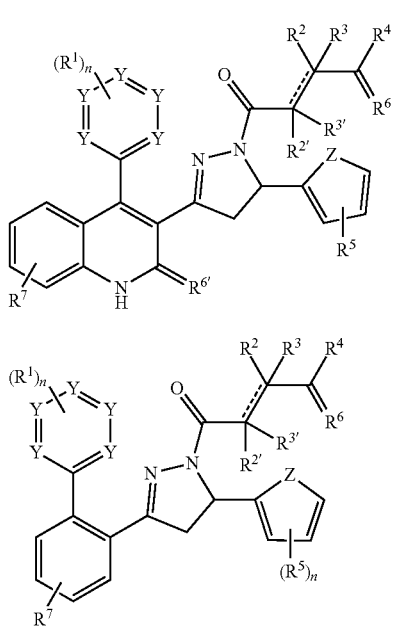

Formula (IC)

Formula (ID)

wherein $R^1$, $R^2$, $R^3$, $R^{2'}$, $R^{3'}$, $R^4$, $R^5$, $R^6$, $R^{6'}$, $R^7$, and n are as defined in claim 1;

wherein Y, in each occurrence, is independently N or CH; and wherein Z is S or O.

9. The compound of claim 1, which is:

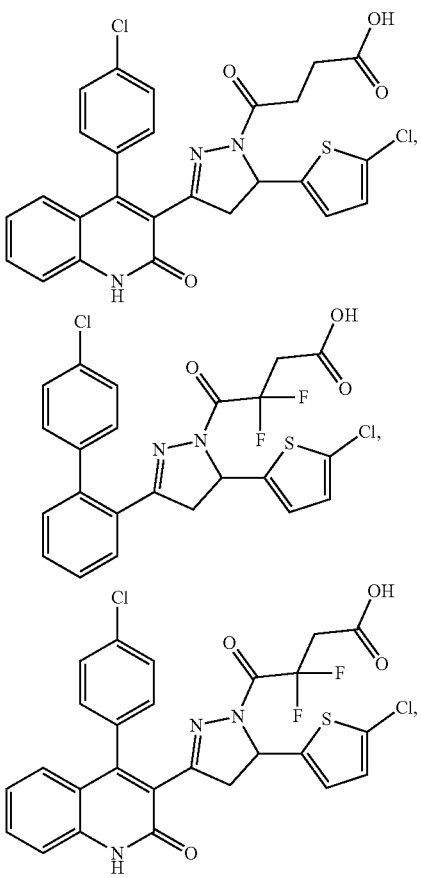

or a salt thereof.

10. A method of treating a neurological disorder in a subject in need thereof, the method comprising administering an effective amount of the compound of claim 1 to the subject.

11. The method of claim 10, wherein the treating of the neurological disorder comprises providing neuroprotection, preventing neurodegeneration, treating neuropathic pain or treating schizophrenia, psychoses or depression.

12. A pharmaceutical composition comprising the compound of claim 1 and a pharmaceutically acceptable excipient, wherein the pharmaceutical composition is in the form of tablets, capsules, pills, gels, granules, aerosols, aqueous buffers, nanoparticle formulations, emulsions or liposomes.

13. The pharmaceutical composition of claim 12, further comprising one or more further active agents.

14. The method of claim 10, wherein the compound is administered in combination with one or more further active agents.

15. The compound of claim 1, wherein Ring C is a monocyclic aryl or heteroaryl ring.

16. The compound of claim 1, wherein $R^{6'}$ is O.

17. The compound of claim 1, wherein the dashed bond represented by ----- is a single bond.

18. The compound of claim 7, wherein Ring A, when considered together with its $R^5$ substitutent(s), is
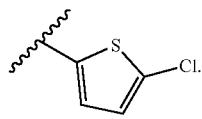 [SMILES: *c1ccc(Cl)s1]
19. The compound of claim 18, wherein the compound has the following structure of a salt thereof:
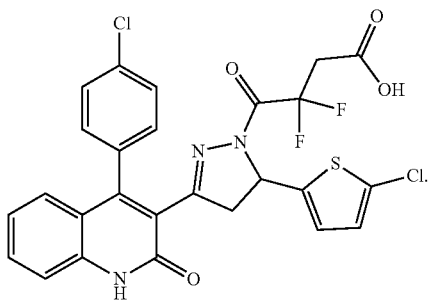 [SMILES: O=C(O)CC(F)(F)C(=O)N1N=C(c2c(-c3ccc(Cl)cc3)c3ccccc3[nH]c2=O)CC1c1ccc(Cl)s1]
20. The composition comprising a compound of claim 1, wherein the compound is a purified S enantiomer of Formula (I) as shown below:
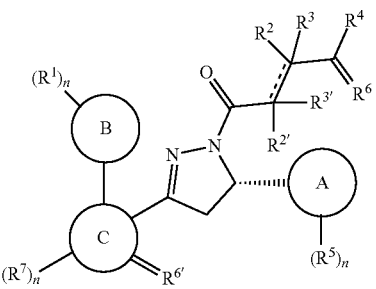
or a salt thereof.
* * * * *